(12) United States Patent
Grant et al.

(10) Patent No.: US 7,935,921 B2
(45) Date of Patent: May 3, 2011

(54) METHODS AND SYSTEMS FOR THE QUANTITATIVE ANALYSIS OF BIOMARKERS

(75) Inventors: Russell Philip Grant, Chapel Hill, NC (US); Andrew Dennis Wagner, New Haven, CT (US); Mary Katherine Morr, Thousand Oaks, CA (US); Milan Rameshkumar Patel, West Hills, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 478 days.

(21) Appl. No.: 11/805,985

(22) Filed: May 25, 2007

(65) Prior Publication Data
US 2008/0128606 A1 Jun. 5, 2008

Related U.S. Application Data

(60) Provisional application No. 60/808,812, filed on May 26, 2006.

(51) Int. Cl.
*G01N 30/72* (2006.01)
(52) U.S. Cl. .......................... 250/288; 250/282
(58) Field of Classification Search .................. 435/7.1, 435/7.2, 7.91, 7.92, 6; 436/56, 131; 250/288, 250/282, 281
See application file for complete search history.

(56) References Cited

U.S. PATENT DOCUMENTS

| | | | |
|---|---|---|---|
| 5,447,553 A | 9/1995 | Apffel, Jr. et al. | |
| 5,772,874 A | 6/1998 | Quinn et al. | |
| 5,795,469 A | 8/1998 | Quinn et al. | |
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,339,218 B1 | 1/2002 | Kato et al. | |
| 6,410,913 B1 | 6/2002 | Brekenfeld et al. | |
| 6,437,327 B2 | 8/2002 | Takada et al. | |
| 6,541,263 B2 | 4/2003 | Gao | |
| 6,635,173 B2 | 10/2003 | Brann | |
| 6,808,635 B2 | 10/2004 | Brann | |
| 7,452,678 B2 * | 11/2008 | Durham et al. ................ | 435/7.1 |
| 2002/0084222 A1 | 7/2002 | Brann | |
| 2003/0015019 A1 | 1/2003 | O'Brien | |

(Continued)

FOREIGN PATENT DOCUMENTS

WO WO 03/089921 A1 10/2003

(Continued)

OTHER PUBLICATIONS

Anari, M. et al., Derivation of ethinylestradiol with dansyl chloride to enhance electrospray ionization: application in trace analysis of ethinylestradiol in rhesus monkey plasma, Anal. Chem., vol. 74, No. 16, pp. 4136-4144, 2002.

(Continued)

*Primary Examiner* — Kiet T Nguyen
(74) *Attorney, Agent, or Firm* — Kilpatrick Townsend & Stockton LLP

(57) ABSTRACT

Disclosed are methods and systems using liquid chromatography/tandem mass spectrometry (LC-MS/MS and 2D-LC-MS/MS) for the analysis of endogenous biomarkers, including steroid hormones, such as estrone and estradiol, thyroid hormones, such as free thyroxine, and metabolites, such as 25-hydroxyvitamin D2 and 25-hydroxyvitamin D3, in biological samples.

8 Claims, 36 Drawing Sheets

U.S. PATENT DOCUMENTS

2004/0235188 A1  11/2004  Soldin
2004/0235193 A1  11/2004  Soldin
2005/0161399 A1   7/2005  Dillon et al.

FOREIGN PATENT DOCUMENTS

WO  WO 2004/090525 A1  10/2004
WO  WO 2004/090553 A1  10/2004

OTHER PUBLICATIONS

Budzinski, H. et al., Analysis of hormonal steroids in fish plasma and bile by coupling solid-phase extraction to gc/ms, Anal. Bioanal. Chem., vol. 386, pp. 1429-1439, 2006.
Draisci, R. et al., Quantification of 17 β-estradiol residues n bovine serum by liquid chromatography-tandem mass spectrometry with atmospheric pressure chemical ionization, p. 2605-2609, 1998.
Dugo, P. et al., Comprehensive Tow Dimensional Normal Phase (Adsorption)-Reversed-Phase Liquid Chromatography, Anal. Chem., vol. 76, No. 9, pp. 2525-2530, 2004.
Fedeniuk, R. et al., Validaiotn of a gas chromatography mass spectrometry method for the determination of pg/ml levels of 17 β-estradiol and 17 β-trenbolone in bovine serum, J. Chromatogr B. Analyt Technol Biomed Life Sci., vol. 802, No. 2, pp. 307-315, 2004.
Ferretti, G. et al., Simultaneous analysis of 17 α-estradiol and 17β-estradiol in bovine serum by liquid chromatography-tandem mass spectrometry, Journal of Chromatography B, vol. 871, pp. 135-140, 2008.
Guo, T. et al., Steroid profiles using liquid chromatography-tandem mass spectrometry with atmospheric pressure photoionization source, Arch. Pathol. Lab. Med., vol. 128, No. 4, pp. 469-475, 2004.
Higashi, T. et al., Procedure for increasing the detection responses of estrogens in lc-ms based on introduction of a nitrobenzene moiety followed by electron capture atmospheric pressure chemical ionization, Anal. Bioanal. Chem., vol. 386, pp. 658-665, 2006.
Jandera, P. et al., Two-dimensional liquid chromatography normal-phase and reversed-phase separation of (co)oligomers, Journal of Chromatography A, vol. 1119, pp. 3-10, 2006.
Kawaguchi, M. et al., Dual derivatization-stir bar sorptive extraction-thermal desorption-gas chromatography-mass spectrometry for determination of 17β-estradiol in water sample, Journal of Chromatography A, vol. 1105, pp. 140-147, 2006.
Nelson, R. et al., Liquid chromatography-tandem mass spectrometry assay for simultaneous measurement of estradiol and estrone in human plasma, Clinical Chemistry, vol. 50, No. 2, pp. 373-384, 2004.
Tai, S. et al., Development and evaluation of a reference measurement procedure for the determination of estradiol-17β in human serum using isotope-dilution liquid chromatography-tandem mass spectrometry, Anal. Chem., vol. 77, No. 19, pp. 6359-6363, 2005.
Xu, X. et al., Measuring fifteen endogenous estrogens simultaneously in human urine by high-performance liquid chromatography-mass spectrometry, Anal. Chem., vol. 77, No. 20, pp. 6646-6654, 2005.
Zacharia, L. et al., A gas chromatography/mass spectrometry assay to measure estradiol, catecholestradiols, and methoxyestradiols in plasma, Steroids, vol. 69, pp. 255-261, 2004.
Zhang, H. et al., Quantitative and qualitative determination of estrogen sulfates in human urine by liquid chromatography/tandem mass spectrometry using 96-well technology, Anal. Chem., vol. 71, No. 18, pp. 3955-3964, 1999.
Lagana et al., "Liquid chromatography tandem mass spectrometry applied to the analysis of natural and synthetic steroids in environmental waters," *Analytical Letters*, 2001, 34(6): 913-926.
Monnoyer et al., "Development of a high-performance liquid chromatography-tandem mass spectrometry method for the determination of flurogestone acetate in ovine plasma," *Journal of Chromatography B: Biomedicial Sciences & Applications*, 2005, 819(2): 245-251.
Robb et al., "Atmospheric pressure photoionization: an ionization method for liquid chromatography-mass spectrometry," *Anal. Chem.*, 2000, 72(15): 3653-3659.
Zimmer et al., "Comparison of turbulent-flow chromatography with automated solid-phase extraction in 96-well plates and liquid-liquid extraction used as plasma sample preparation techniques for liquid chromatography-tandem mass spectrometry," *J. Chromatogr. A.*, 1999, 854: 23-35.
Yost, *Tandem Mass Spectrometry*, Chapter 8, Ed. McLafferty, John Wiley and Sons: 1983, 175-195.
International Search Report for Patent Cooperation Treaty Application Serial No. PCT/US2007/012525 mailed Jul. 2, 2008.
Written Opinion of the International Searching Authority for Patent Cooperation Treaty Application Serial No. PCT/US2007/012525 mailed Jul. 2, 2008.
de Alda, M. et al., Liquid chromatography-(tandem) mass spectrometry of selected emerging pollutants (steroid sex hormones, drugs and alkylphenolic surfactants) in the aquatic environment, Journal of Chromatography A, vol. 1000, pp. 503-526, 2003.
Antignac, J. et al., Collision-induced dissociation of corticosteroids in electrospray tandem mass spectometry and development of a screening method by high performance liquid chromatography/tandem mass spectrometry, Rapid communications in Mass Spectrometry, vol. 14, pp. 33-39, 2000.
Asperger, A. et al., Trace determination of priority pesticides in water by means of high-speed on-line solid-phase extraction-liquid chromatography-tandem mass spectrometry using turbulent-flow chromatography colums for enrichment and a short monolithic column for fast liquid chromatographic separation, Journal of Chromatography A, vol. 960, pp. 109-119, 2002.
Ayrton, J. et al., Ultra-high flow rate capillary liquid chromatography with Mass Spectrometric detection for the direct analysis of pharmaceuticals in plasma at sub-nanogram per millilitre concentrations, Rapid Communications in Mass Spectrometry, vol. 13, pp. 1657-1662, 1999.
Carignan, G. et al., High-performance liquid chromatographic analysis of estradiol valerate-testosterone enanthate in oily formulations, Journal of Chromatography, vol. 301, pp. 292-296, 1984.
Chang, Y. et al., Quantitative measurement of male steroid hormones using automated on-line solid phase extraction-liquid chromatography-tandem mass spectrometry and comparison with radioimmunoassay, Analyst, vol. 128, pp. 363-368, 2003.
Choi, M. et al., Rapid HPLC-electrospray tadem mass spectrometric assay for urinary testosterone and dihydrotestosterone glucuronides from patients with benign prostate hyperplasia, Clinical Chemistry, vol. 49, No. 2, pp. 322-325, 2003.
Choi, M. et al., Determination of four anabolic steroid metabolites by gas chromatography/mass spectrometry with negative ion chemical ionization and tandem mass spectrometry, Rapid Communications in Mass Spectrometry, vol. 12, pp. 1949-1755, 1998.
Dorgan, J. et al., Measurement of steroid sex hormones in serum, a comparison of radioimmunoassay and mass spectrometry, Steroids, vol. 67, pp. 151-158, 2002.
Draisci, R. et al., Quantitation of anabolic hormones and their metabolites in bovine serum and urine by liquid chromatography-tandem mass spectrometry, Journal of Chromatography A, Vo.. 870, pp. 511-522, 2000.
Friedrich, G. et al., Determination of testosterone metabolites in human hepatocytes I. development of an in-line sample preparation liquid chromatography technique and mass spectroscopic detection of 6β-hydroxytestosterone, Journal of Chromatography A, vol. 784, pp. 49-61, 2003.
Furuta, T. et al., Simultaneous measurements of endogenous and deuterium-labelled tracer variants of androstenedione and teststerone by capillary gas chromatography-mass spectrometry, Journal of Chromatography, vol. 525, pp. 15-23, 1990.
Giraudi, G. et al., Effect of tracer binding to serum proteins in the reliability of a direct free testosterone assay, Steroids, vol. 52, No. 4, pp. 423-424, 1988.
Grant, R. et al., Generic serial and parallel on-line direct-injection using turbulent flow liquid chromatography/tandem mass spectrometry, Rapid Communications in Mass Spectrometry, vol. 1, pp. 1785-1792, 2003.
Griffiths, W. et al., Derivatisation for the characterisation of neutral oxosteroids by electrospray and matrix-assisted laser desorption/ionisation tandem mass spectrometry: the Girard P derivative, Rapid Communications in Mass Spectrometry, vol. 17, pp. 924-935, 2003.

Jemal, M. et al., Comparison of plasma sample purification by manual liquid-liquid extraction and automated 96-well solid-phase extraction for analysis by high-performance liquid chromatography with tandem mass spectrometry, Journal of Chromatography B, vol. 732, pp. 501-508, 1999.

Kim, J. et al., Measurement of 19-nortestosterone and its esters in equine plasma by high-performance liquid chromatography with tandem mass spectrometry, Rapid Communications in Mass Spectrometry, vol. 14, pp. 1835-1840, 2000.

Lewis, R. et al., A novel method for the determination of sildenafil (viagra) and its metabolite (uk-103,320) in postmortem specimens using lc/ms/ms and lc/ms/ms/ms, Office of Aviation Medicine, Washington, D.C., May 2000.

Li, H. et al., A high-performance-liquid-chromatography-based method for the determination of hydroxylated testosterone metabolites formed in vitro liver microsomes from gray seal (*Halichoerus grypus*), Journal of Chromatographic Science, vol. 40, pp. 397-402, 2002.I.

Merchant, M. et al., Recent advancements in surface-enhanced laser desorption/ionization-time of flight-mass spectrometry, Electrophoresis, vol. 21, pp. 1164-1167, 2000.

ropero-Miller, J. et al., Simultaneous quantitation of opioids in blood by gc-ei-ms analysis following deproteination, detautomerization of keto analytes, solid-phase extraction, and trimethylsilyl derivatization, Journal of Analytical Toxicology, vol. 26, pp. 524-528, 2002.

Navajas, R. et al., Determination of epitestosterone and testosterone in urine by high performance liquid chromatography, Journal of Chromatography B, vol. 673, pp. 159-164, 1995.

Ng, B. et al, Determination of plasma testosterone using a simple liquid chromatographic method, Journal of Chromatography B, vol. 793, pp. 421-426, 2003.

Oka, K. et al., Combined use of rapid flow fractionation and high-performance liquid chromatography for the determination of serum testosterone and application to study of stress response to physical exercise, Journal of Chromatography, vol. 423, pp. 285-291, 1987.

Starcevic, B. et al., Liquid chromatography-tandem mass spectrometry assay for human serum testosterone and trideuterated testosterone, Journal of Chromatography B, vol. 792, pp. 197-204, 2003.

Tachibana, S. et al., Simultaneous determination of testosterone metabolites in liver microsomes using column-switching semi-microcolumn high performance liquid chromatography, Analytical Biochemistry, vol. 295, pp. 248-256, 2001.

Tiller, P. et al., Drug quantitation on a benchtop liquid chromatography-tandem mass spectrometry system, Journal of Chromatography A, vol. 771, pp. 119-125, 1997.

Wang, D. et al., Rapid quantitation of testosterone hydroxyl metabolites by ultra-performance liquid chromatography and mass spectrometry, Journal of Chromatography B, vol. 855, pp. 290-294, 2007.

Wright, G. et al., Proteinchip surface enhanced laser desorption/ionization (seldi) mass spectrometry: a novel protein biochip technology for detection of prostate cancer biomarkers in complex protein mixtures, Prostate Cancer and Prostate Disease, vol. 2, pp. 264-276, 1999.

Williams, T. et al., Electrospray collision-induced dissociation of testosterone and testosterone hydroxy analogs, Journal of Mass Spectrometry, vol. 34, pp. 206-216, 1999.

Xia, Y. et al., Ternary-column system for high-throughput direct-injection bioanalysis by liquid chromatography/tandem mass spectrometry, Rapid Communications in Mass Spectrometry, vol. 14, pp. 105-111, 2000.

Patent Cooperation Treaty, International Search Report, International Application No. PCT/US2008/006908, mailed Sep. 12, 2008.

Office Action mailed Aug. 30, 2010 corresponding to Canadian Patent Application No. 2,654,319.

* cited by examiner

Estrone Sulfate
LOQ (100 pg/mL)

Estrone
ULOQ (500 pg/mL)

Free Thyroxine

25-Hydroxyvitamin D2

Total 25-Hydroxyvitamin D (25-Hydroxyvitamin D2+D3)

METHODS AND SYSTEMS FOR THE QUANTITATIVE ANALYSIS OF BIOMARKERS

PRIORITY CLAIM TO RELATED APPLICATIONS

This application claims priority to U.S. provisional patent application Ser. No. 60/808,812, filed May 26, 2006. The disclosure of U.S. provisional patent application Ser. No. 60/808,812 is incorporated by reference in its entirety herein.

FIELD OF INVENTION

The presently disclosed subject matter relates to methods and systems for the analysis of biomarkers. In certain embodiments, the biomarkers are endogenous to human subjects such that the measurement may be used for clinical diagnosis.

BACKGROUND

Biomarkers, such as hormones, vitamins, metabolites, can be used for the clinical diagnosis of multiple disorders and as endogenous biomarkers in endocrinology. For example, the measurement of estrogen compounds, such as estrone and estradiol can be used to evaluate ovarian function and to evaluate excess or diminished estrogen levels in a patient. Also, measurement of thyroxine can be used to quantify thyroid function.

Requirements for the clinical diagnostic testing of endogenous biomarkers in endocrinology may include highly sensitive and specific assays, the ability to analyze small sample volumes (e.g., pediatric sample volumes can be limited to less than about 200 µL), and the ability to screen for multiple analytes to accurately diagnose a disease state, e.g., an endocrine disorder. Historically, radioimmunoassay (RIA) and enzyme-linked immunoassay (ELISA) methods have been used in such clinical diagnostic testing. Immunoassay methods (IA), such as RIA and EIA, however, may suffer from low throughput, antibody cross-reactivity, which can require extra preparation for specificity, and poor scalability. Also, the analysis of endogenous biomarkers by RIA may require multiple serial dilutions for the analysis of each individual marker, which can lead to the need to make multiple adjustments to normalize sample volumes and/or the need for multiple separate tests. Also, immunoassay tesing is not particularly conducive to the analysis of multiple biomarkers in each sample. The analysis for multiple analytes in a single assay can allow for using samples of reduced size which results in assays of increased sensitivity and efficiency per sample.

An important class of hormones are the steroid hormones, such as testosterone and estrogens. Testosterone develops and maintains the male secondary sex characteristics, and promotes growth and development of sperm. Estrogen is the term used for a group of hormones of which there are three principle forms, estrone, estradiol, and estriol.

For example, relatively small variations in estrogen levels may be clinically significant. Generally, the level of estrogen in post-menopausal women, adult males, and prepubescent children is $\leq$10 pg/mL. Elevated estrogen levels in children may lead to precocious puberty (and short stature). In post-menopausal women, low estrogen levels may require replacement, whereas levels greater than 5 pg/mL may be prognostic for certain cancers. In adult males, elevated estrogen levels may be indicative of certain disease states (testicular cancer). In adult females, reduced or elevated levels may also be indicative of certain cancers (e.g., ovarian cancer). A level of serum estrogen of 15 pg/mL is clinically different from 10 pg/mL and thus, measurement of estrogen compounds (e.g., estradiol and estrone) requires an LLOQ of 1-5 pg/mL irrespective of sample type, patient age, gender and diet.

Another important class of hormones are the thyroid hormones. Thyroxine (T4) and triiodothyronine (T3) are examples of thyroid hormones. T4 and T3 enter cells and bind to intracellular receptors. T4 and T3 are important in regulation of a number of factors including growth and development, carbohydrate metabolism, oxygen consumption, and protein synthesis. T4 acts as a prohormone, as the bulk of T3 present in blood is produced by monodeiodination of T4 by intracellular enzymes. Thyroid hormone concentrations in blood are essential tests for the assessment of thyroid function.

Thus, there is a need to develop analytical techniques that can be used for the measurement of endogenous biomarkers, and for methods that provide more sensitivity and higher throughput than RIA. Until recently, however, only GC-MS or LC-MS/MS with derivatization has been successful for small sample volumes. Thus, there is a need in the art for LC-MS/MS techniques for the analysis of endogenous biomarkers for clinical diagnosis in endocrinology capable of providing detection limits at acceptable levels, without the need for the cumbersome derivatization processes.

SUMMARY

In some embodiments, the presently disclosed subject matter provides methods and systems for the quantitative analysis of endocrine biomarkers in a test sample. The quantification of such markers may, in certain embodiments, be used for clinical diagnosis in endocrinology. For example, in some embodiments, the methods and systems of the present invention may be used for the quantitative analysis of total levels of certain hormones, including steroid hormones, such as estrone and estradiol, and their metabolites, such as estrone sulfate. In other embodiments, the methods and systems of the present invention provide for the quantitative analysis of biomarkers that can be difficult to detect in their active state. For example, the systems and methods of the present invention may be used to quantify free (i.e., not bound to protein) serum hormones, such as free thyroxine (T4) in biological samples. Or, in other embodiments, the systems and methods of the present invention may be used to quantify free triiodothyronine (T3) or testosterone. In an embodiment, the methods and systems of the present invention allow for measurement of such hormones without the need for derivatation processes.

In some embodiments, the biomarkers of interest are estradiol and/or estrone. Thus, in one embodiment, the present invention comprises a method for determining the presence or amount of estradiol in a sample by tandem mass spectrometry, comprising: (a) generating a dehydrated precursor ion of the estradiol; (b) generating one or more fragment ions of the precursor ion; and (c) detecting the presence or amount of one or more of the ions generated in step (a) or (b) or both, and relating the detected ions to the presence or amount of the estradiol in the sample. In an embodiment, the sample comprises a mixture of estradiol and estrone.

In other embodiments, the biomarker comprises free thyroxine (T4) or triiodothyronine (T3). In certain embodiments, the present invention provides a high-throughput assay for free thyroxine (T4). Thus, in one embodiment, the present invention comprises a method for determining the presence or amount of free thyroxine in a plurality of samples by tandem mass spectrometry, comprising: (a) dialyzing the plurality of samples to separate the free thyroxine from the protein-bound thyroxine in the samples; (b) generating a precursor ion of the thyroxine; (b) generating one or more fragment ions of the thyroxine; and (c) detecting the presence or amount of one or more of the ions generated in step (b) or (c) or both, and relating the detected ions to the presence or amount of the free thyroxine in the plurality of samples.

In some embodiments, the methods and systems of the present invention comprise liquid chromatography (LC) methods in combination with other analytical techniques as a means to measure such biomarkers with high sensitivity and high throughput. In certain embodiments, the present invention comprises quantitative liquid chromatography tandem mass spectrometry (LC-MS/MS) analysis of endocrine biomarkers in a test sample. In some embodiments, two-dimensional or tandem LC is used. The method may include, in alternate embodiments, liquid-liquid extractions, dialysis, sample dilution, and/or sample dehydration steps prior to analysis by tandem mass spectrometry.

Accordingly, embodiments of the present invention may provide methods for the quantitative LC-MS/MS and 2D-LC-MS/MS analysis of hormones, including steroid hormones, such as estrone and estradiol. Additionally or alternatively, embodiments of the present invention may provide methods for the quantitative determination of a free (i.e., non-protein bound) hormone or metabolite using dialysis in combination with LC-MS/MS analysis for hormones that in biological samples, may be predominantly protein-bound. Such hormones may include free thyroxine (T4), free triiodothyronine (3), or free testosterone. Certain objects of the present invention, having been stated hereinabove, will become further evident as the description proceeds when taken in connection with the accompanying figures and examples as described herein below.

BRIEF DESCRIPTION OF THE DRAWINGS

Having thus described the invention in general terms, reference will now be made to the accompanying drawings, which are not necessarily drawn to scale.

Figure 1:
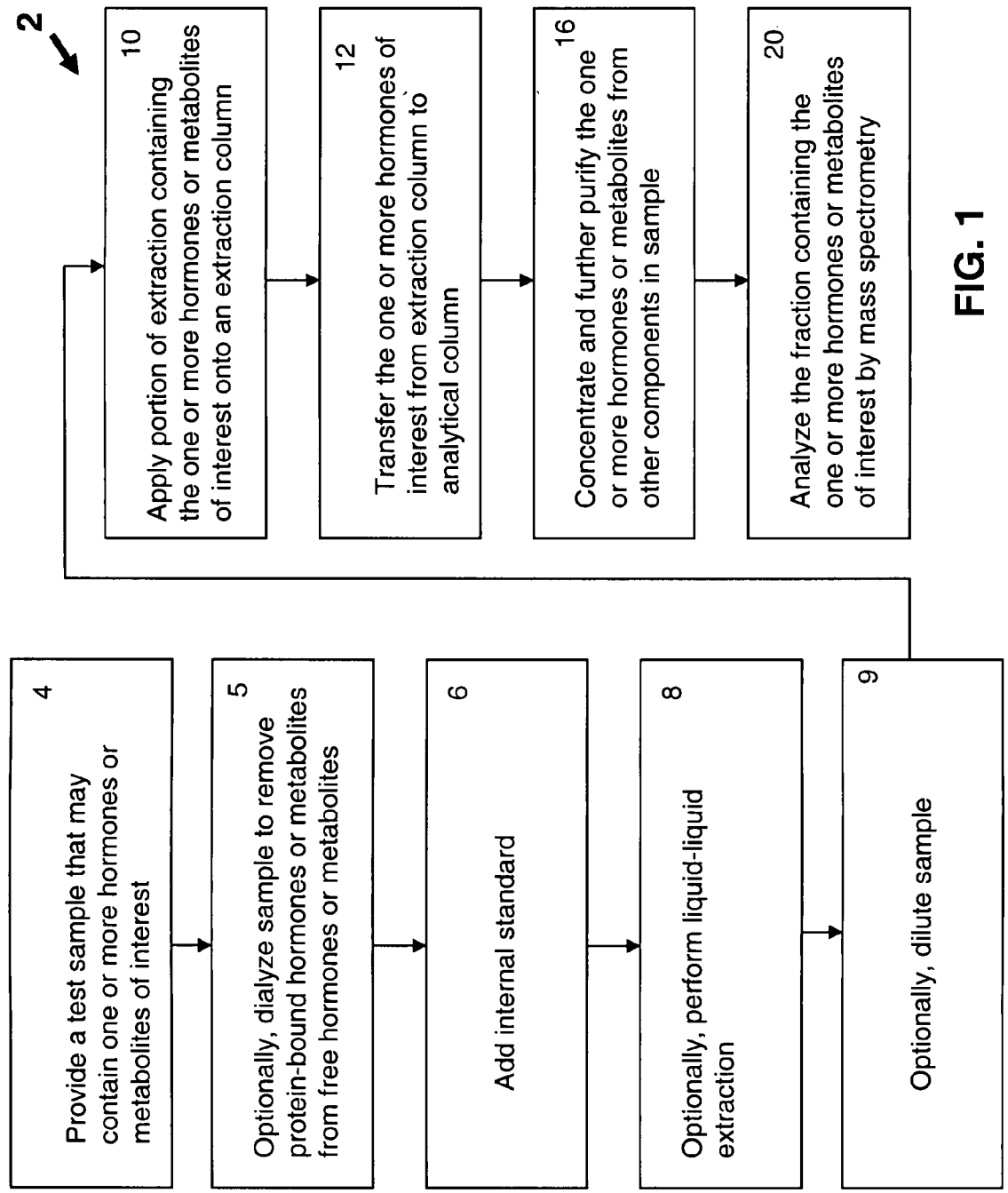
Figure 2A:
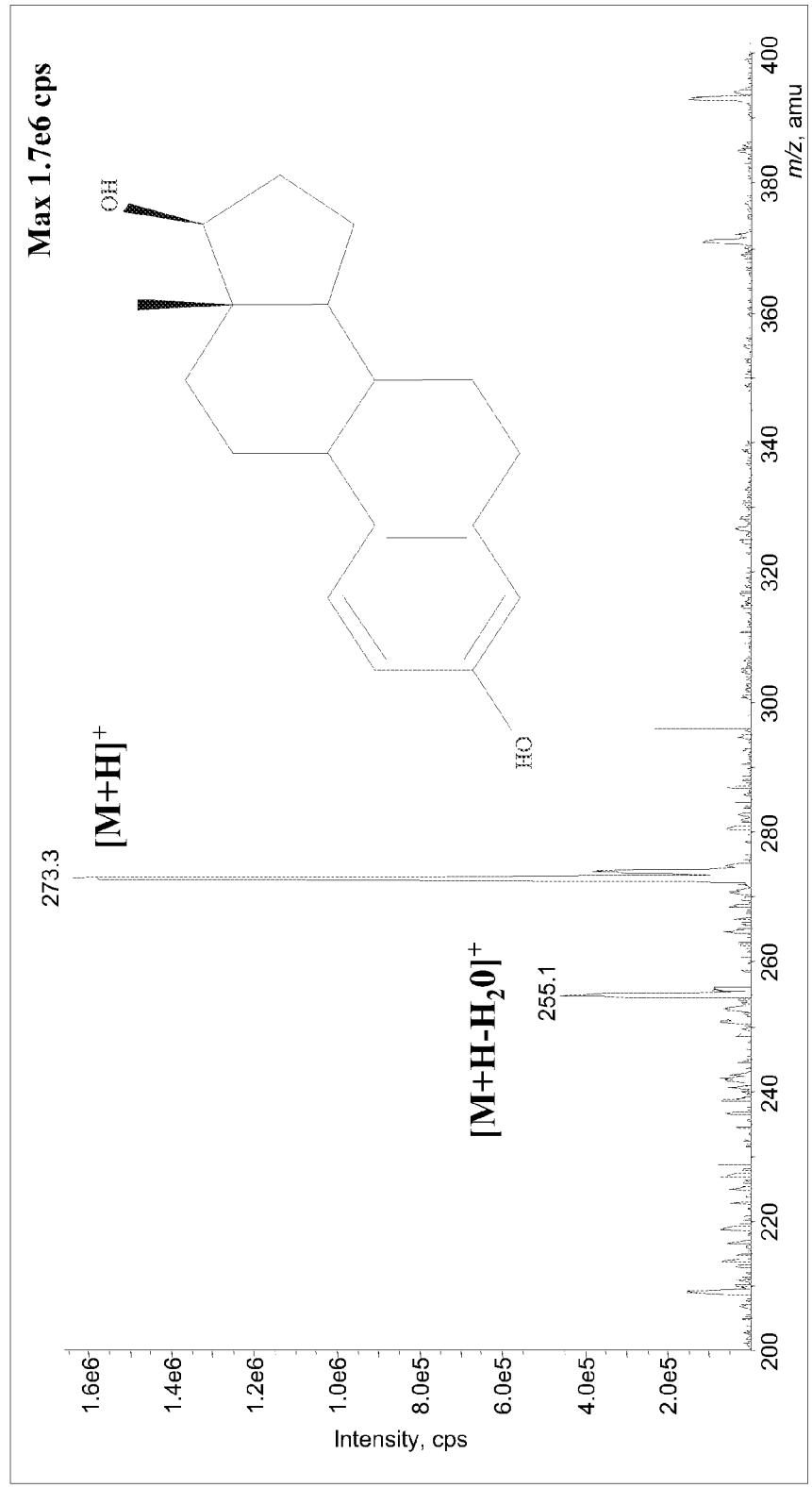
Figure 2B:
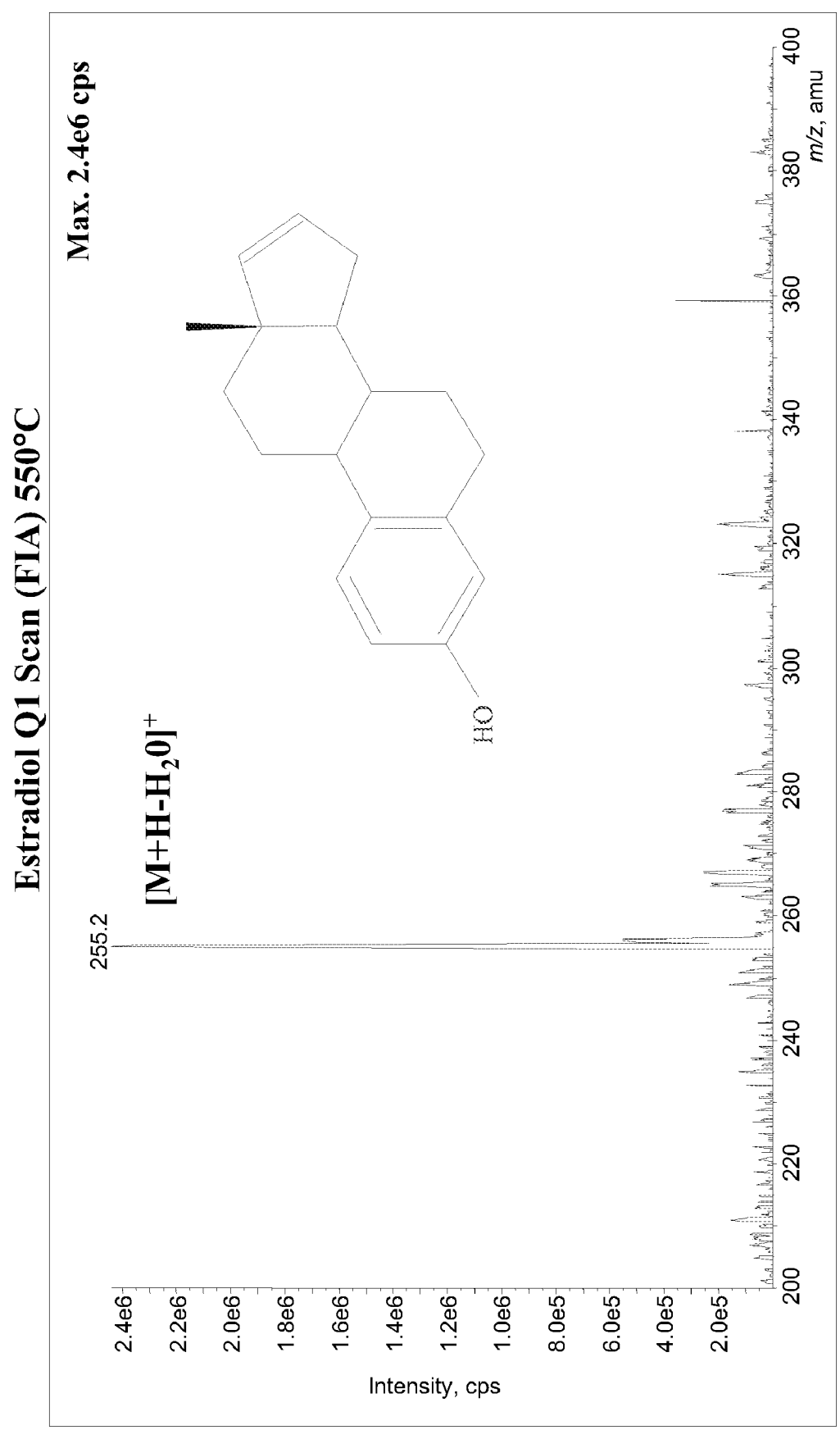
Figure 2C:
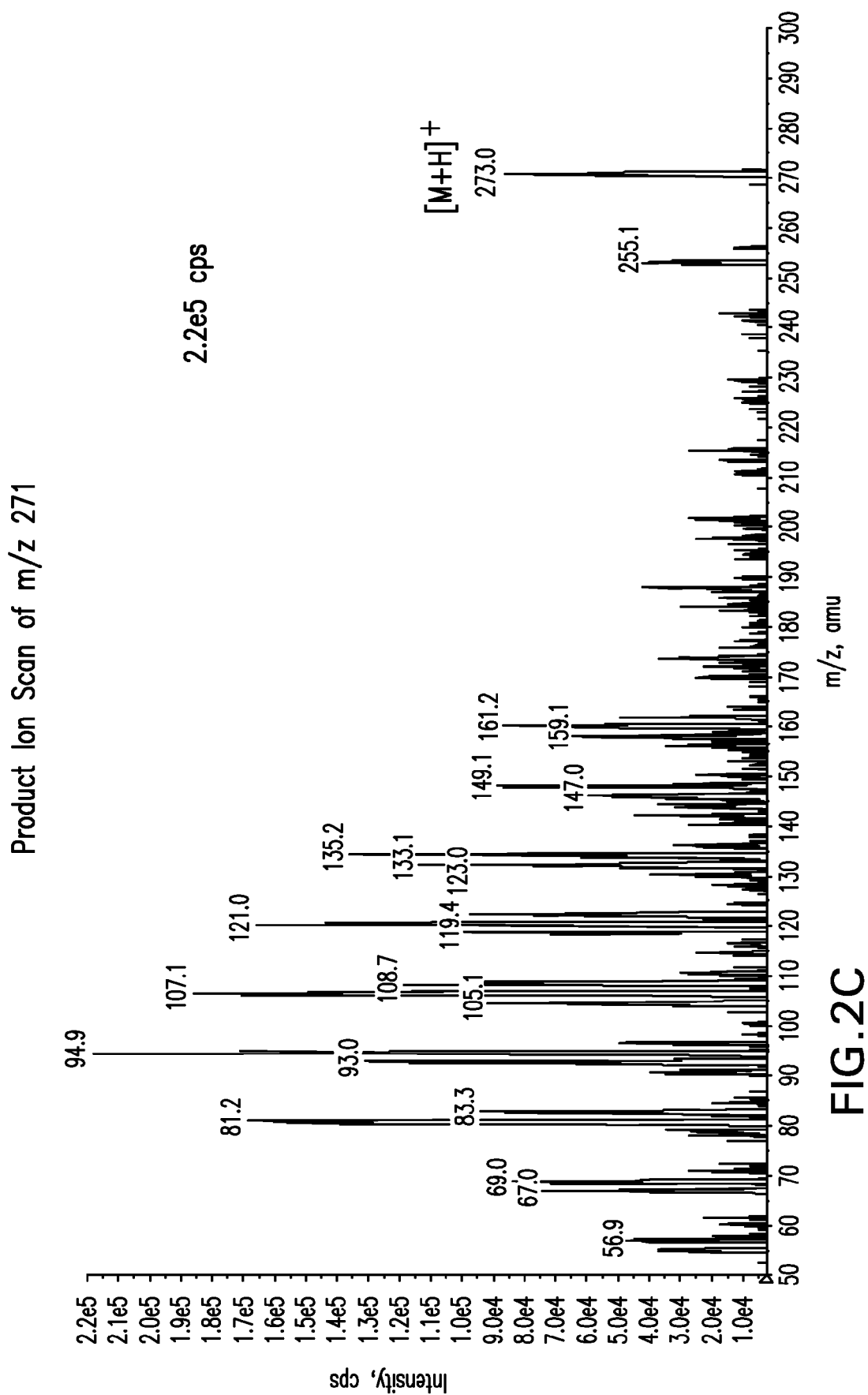
Figure 2D:
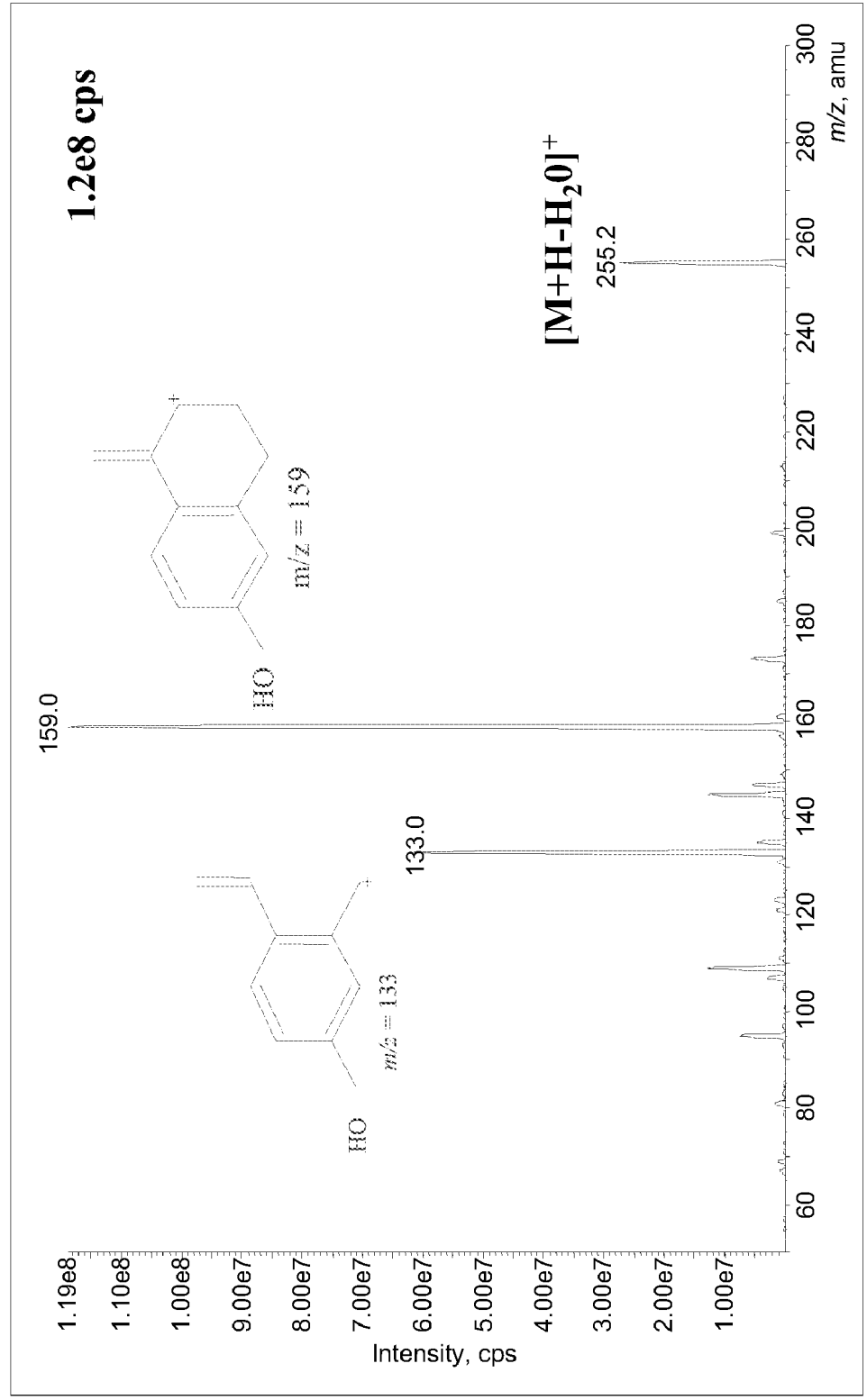

FIG. 1 shows a flow chart of a method for quantitative analysis of a biomarker of interest in accordance with one embodiment of the present invention.

FIG. 2 shows dehydration of estradiol and the effect on mass spectrometry (MS) analysis in accordance with an embodiment of the present invention.

Figure 3:
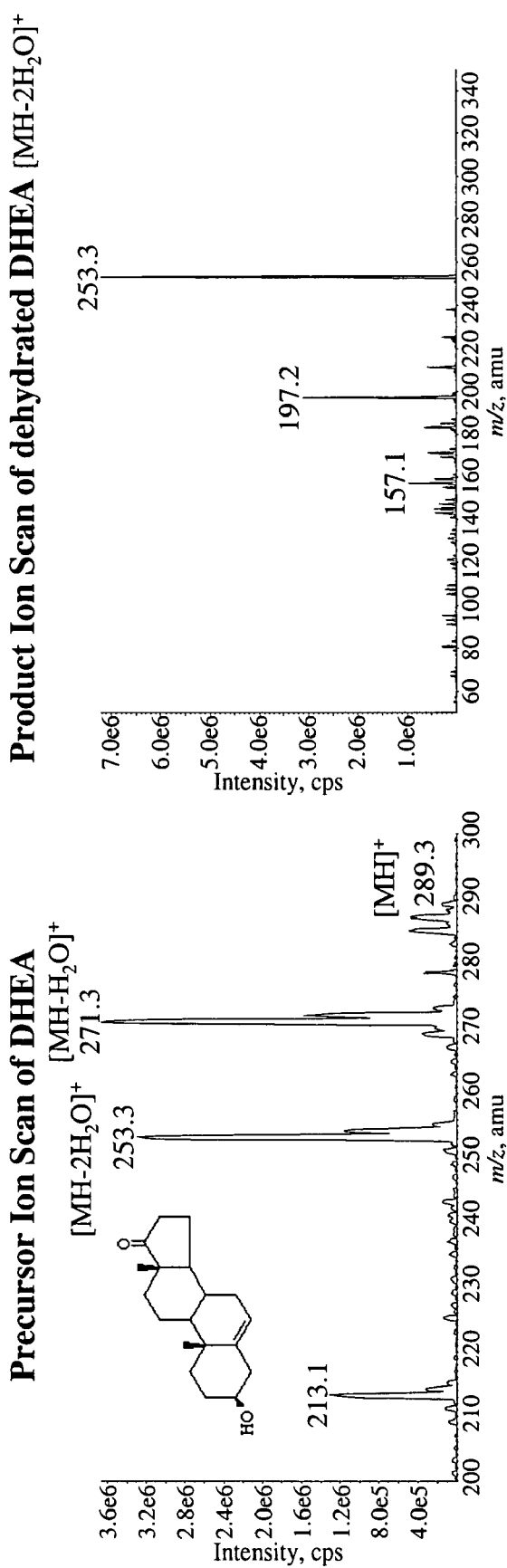

FIG. 3 shows potential isobaric interferences for measurement of estrone and estradiol due to dehydration of dehydroepiandrosterone (DHEA) in accordance with one embodiment of the present invention.

Figure 4:
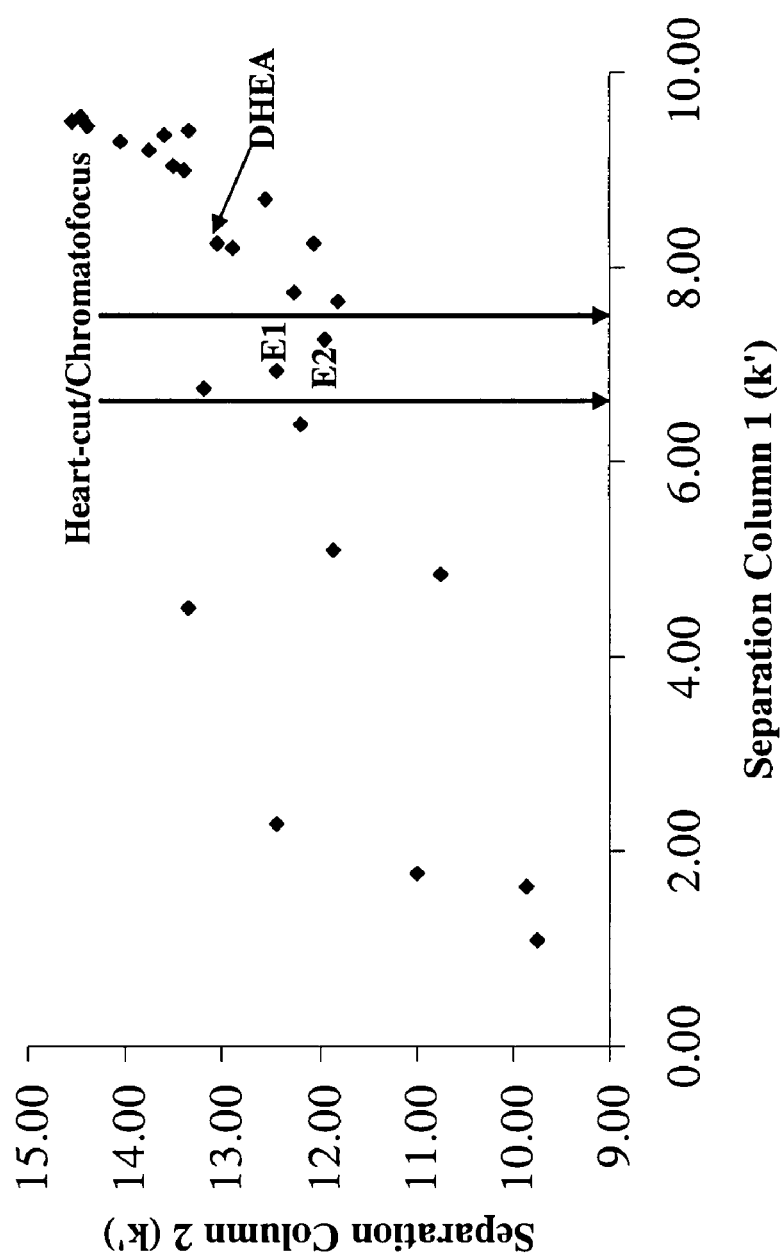

FIG. 4 shows an example of heart-cutting from a primary separation gradient to remove compounds that comprise isobaric interference in the analysis of estrone and estradiol in accordance with one embodiment of the present invention.

Figure 5:
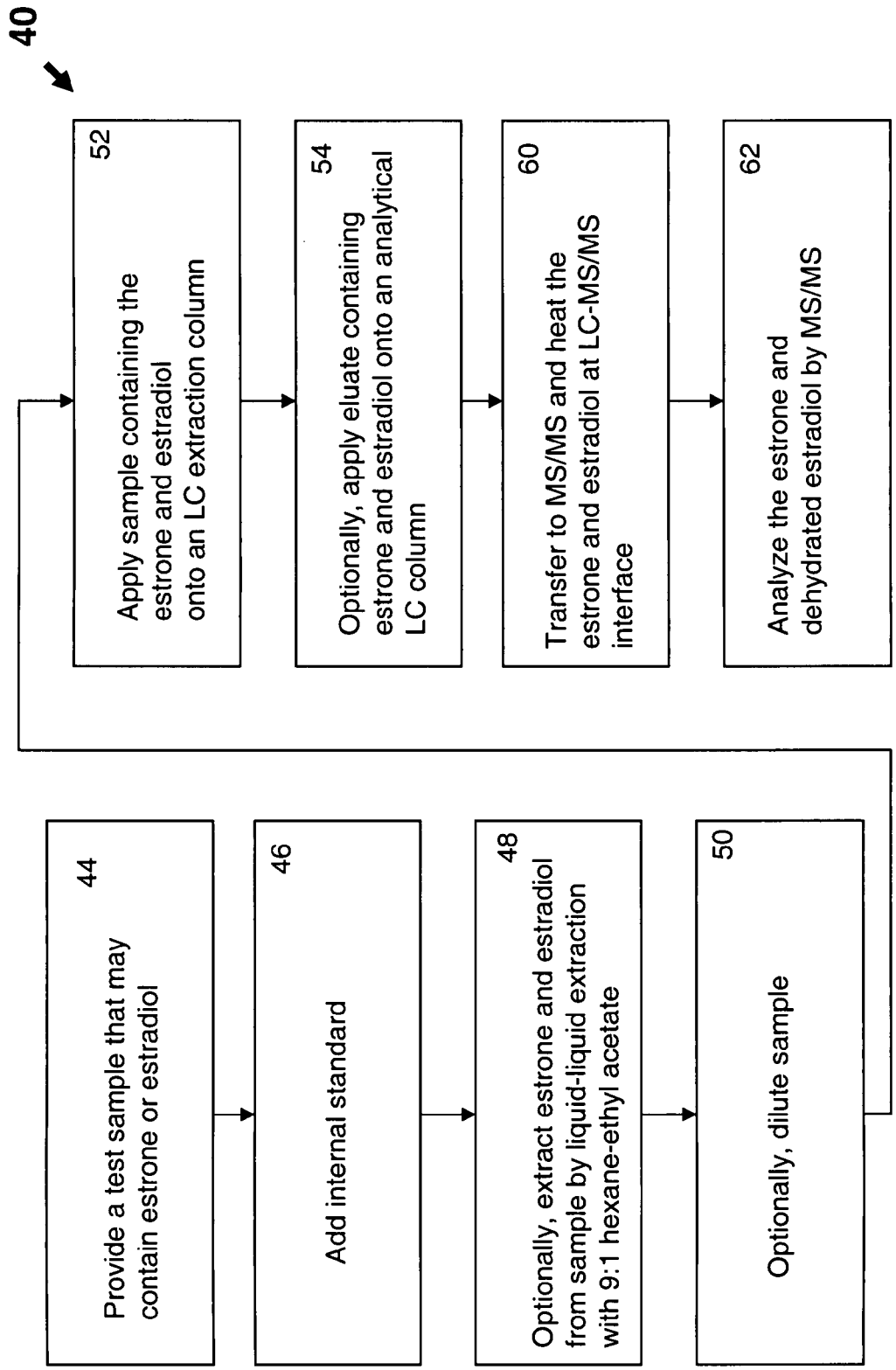

FIG. 5 shows a method for the quantification of estrone and estradiol in accordance with an embodiment of the present invention.

Figure 6:
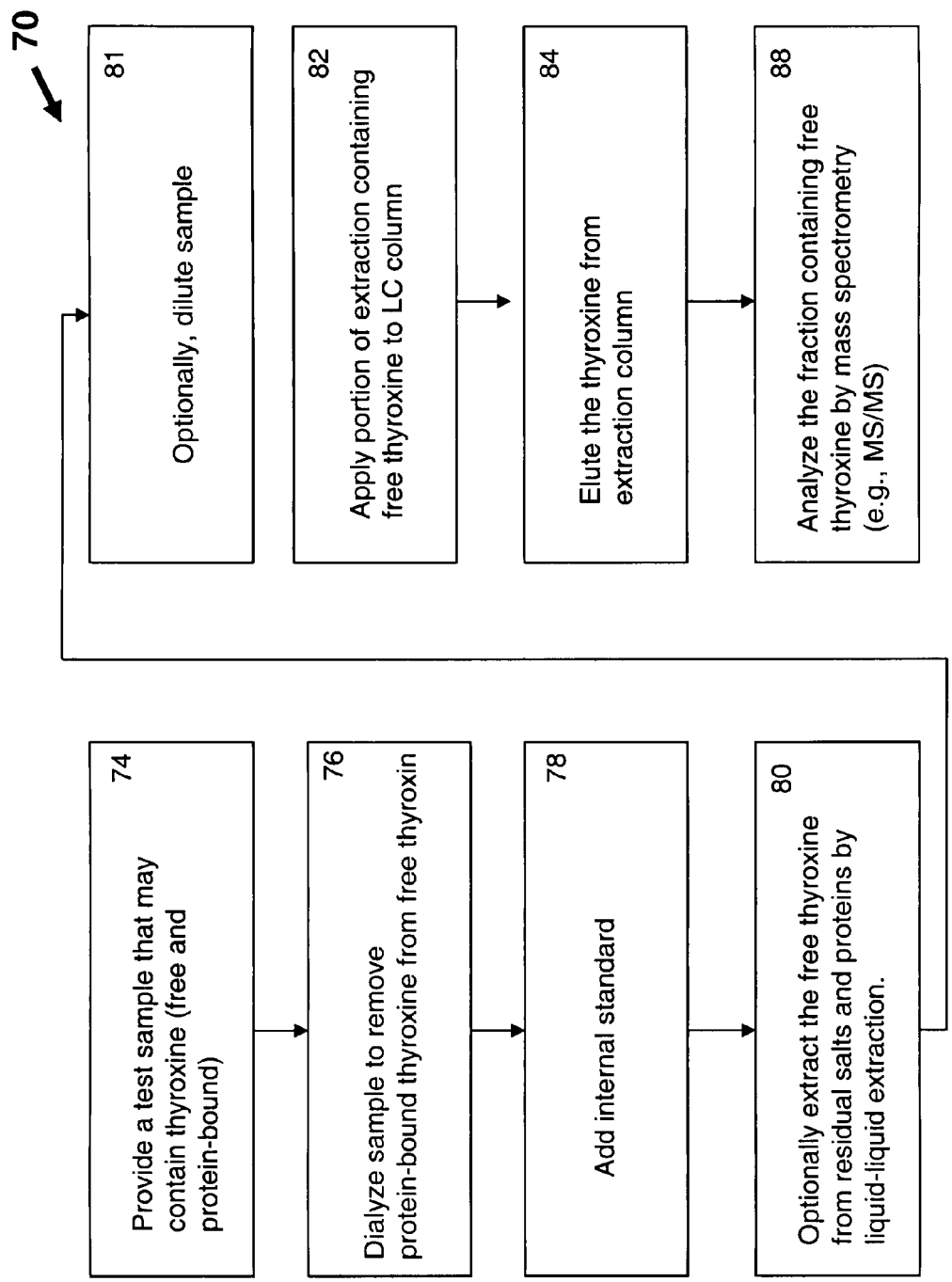

FIG. 6 shows a method for the quantification of free thyroxine (T4) in accordance with an embodiment of the present invention.

FIG. 7 shows a system for quantitative analysis of a metabolite in accordance with one embodiment of the present invention (Panel A), and a system for multiplex analysis (Panel B) in accordance with alternate embodiments of the present invention.

Figure 8:
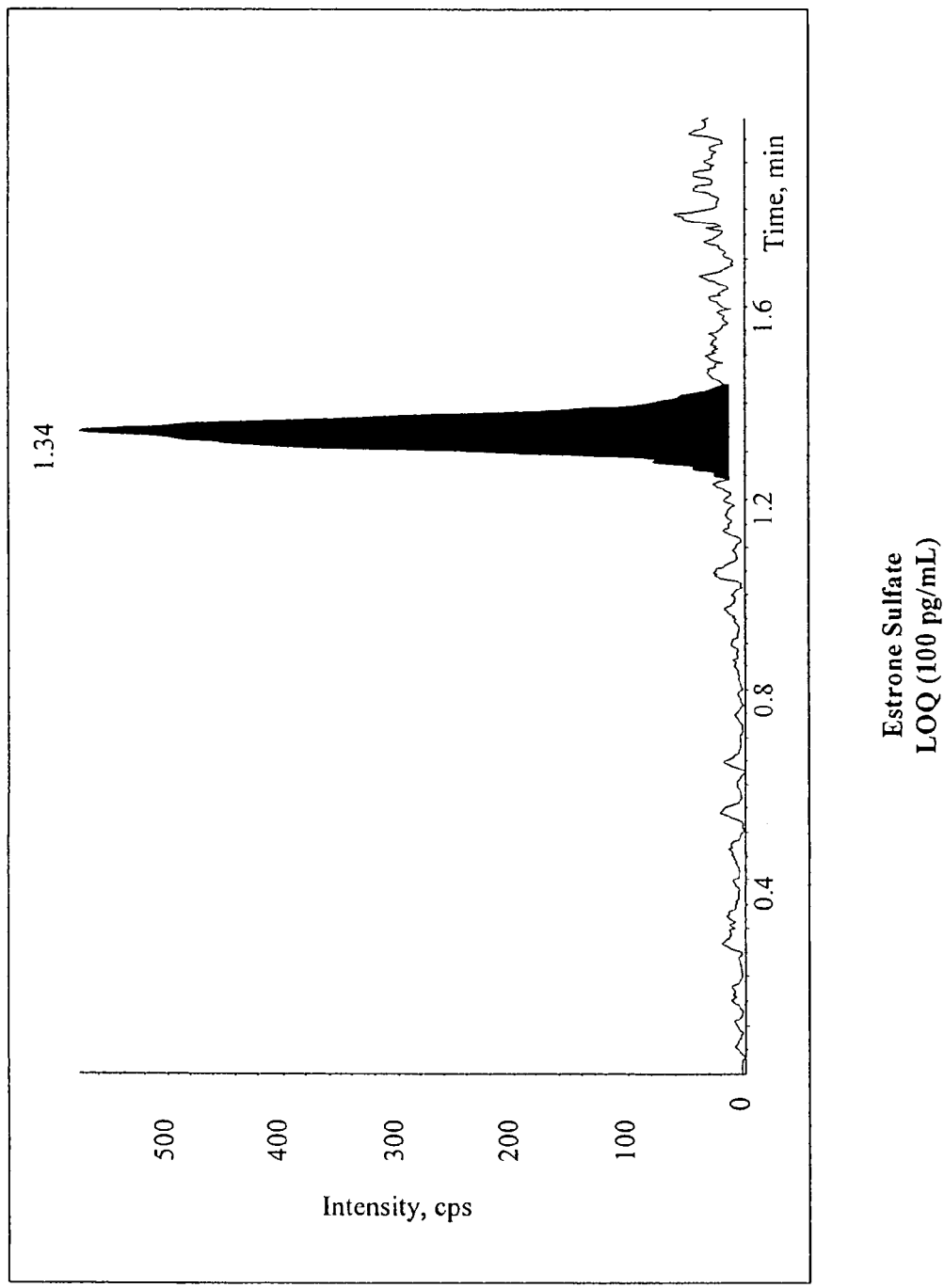

FIG. 8 shows a LC-MS/MS chromatogram of estrone sulfate at a limit of quantification of 100 pg/mL in accordance with one embodiment of the present invention.

Figure 9:
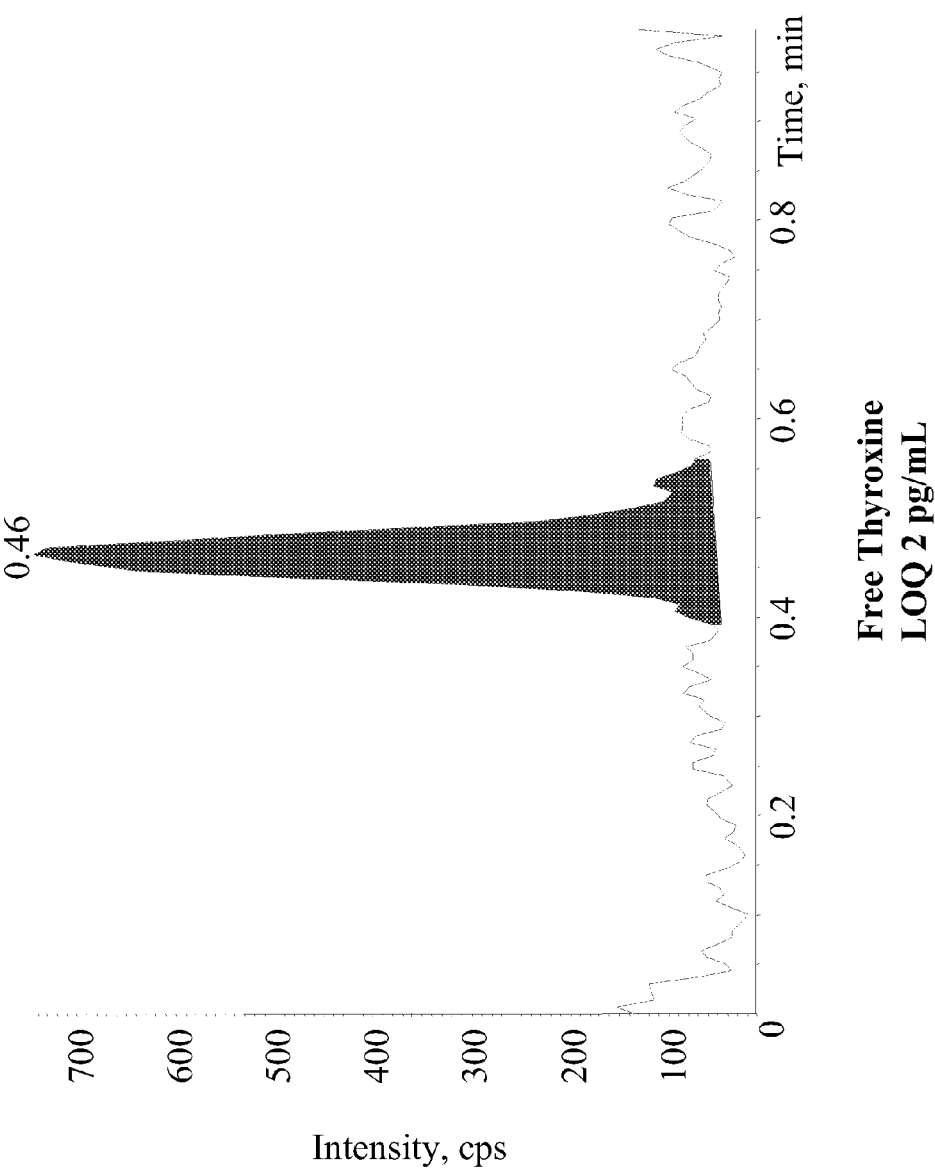

FIG. 9 shows a LC-MS/MS chromatogram of free thyroxine at a limit of quantification of 2 pg/mL in accordance with one embodiment of the present invention.

Figure 10:
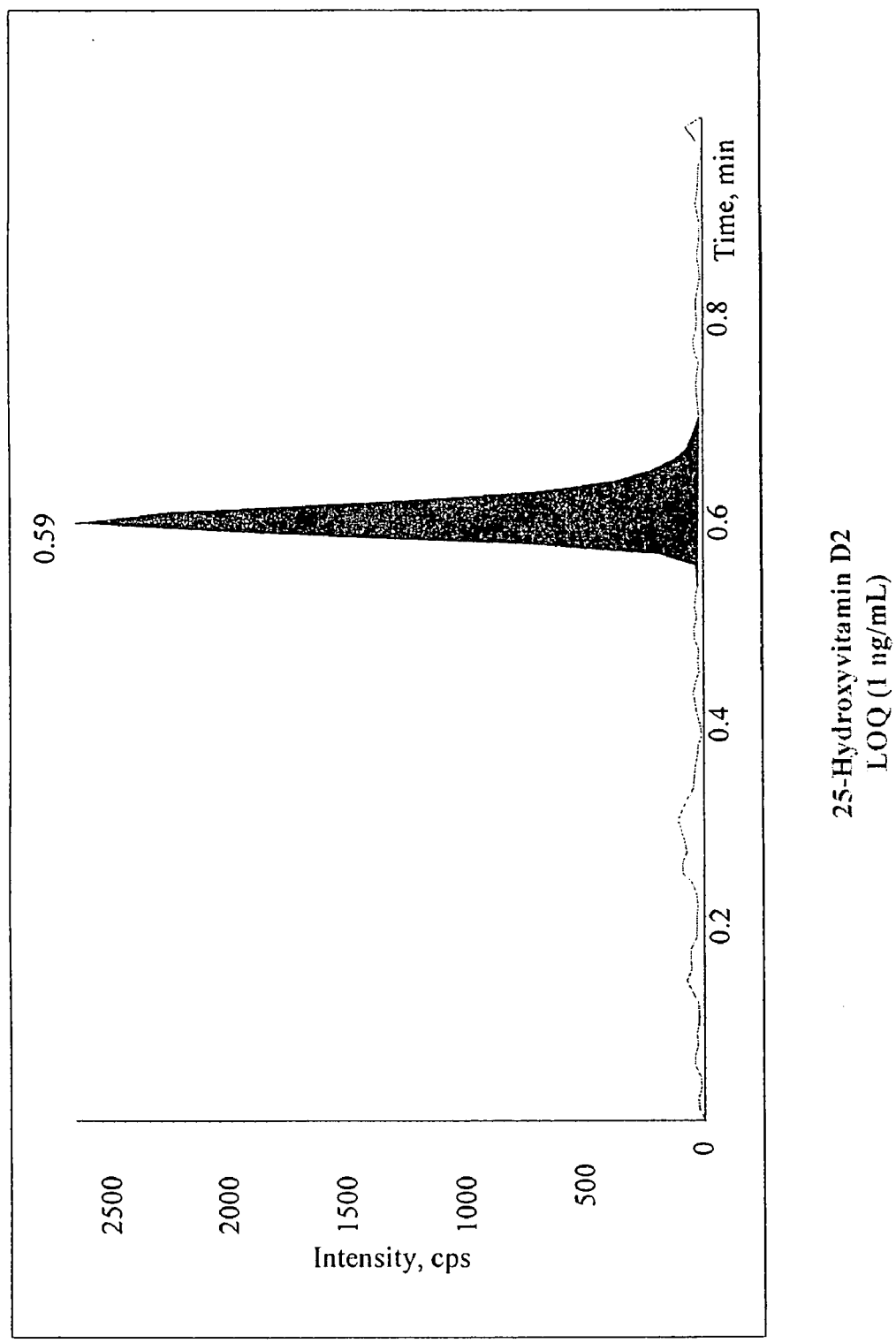

FIG. 10 shows a 2D-LC-MS/MS chromatogram of 25-hydroxyvitamin D2 at a limit of quantification of 1 ng/mL in accordance with one embodiment of the present invention.

Figure 11:
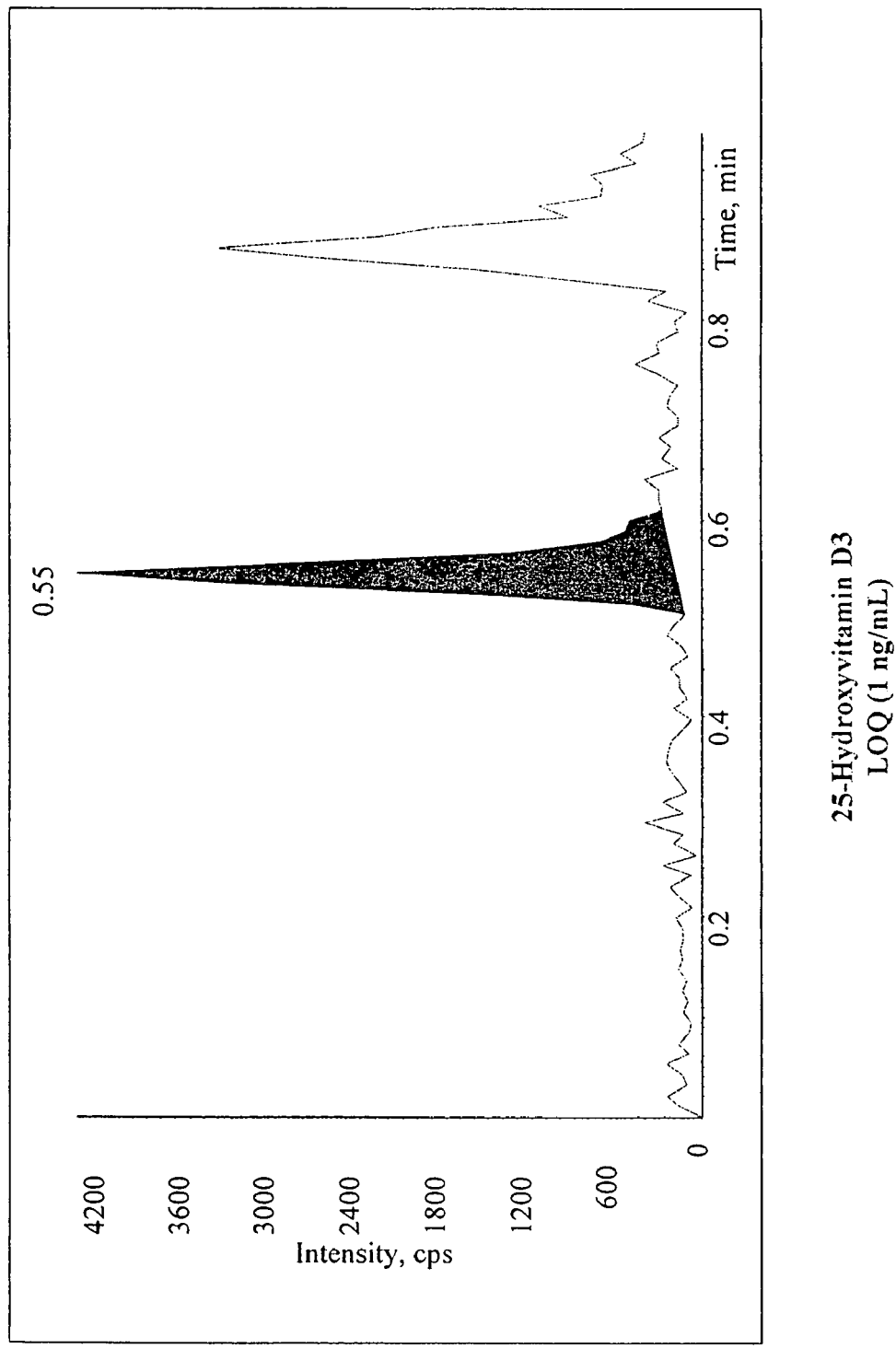

FIG. 11 shows a 2D-LC-MS/MS chromatogram of 25-hydroxyvitamin D3 at a limit of quantification of 1 ng/mL in accordance with one embodiment of the present invention.

Figure 12:
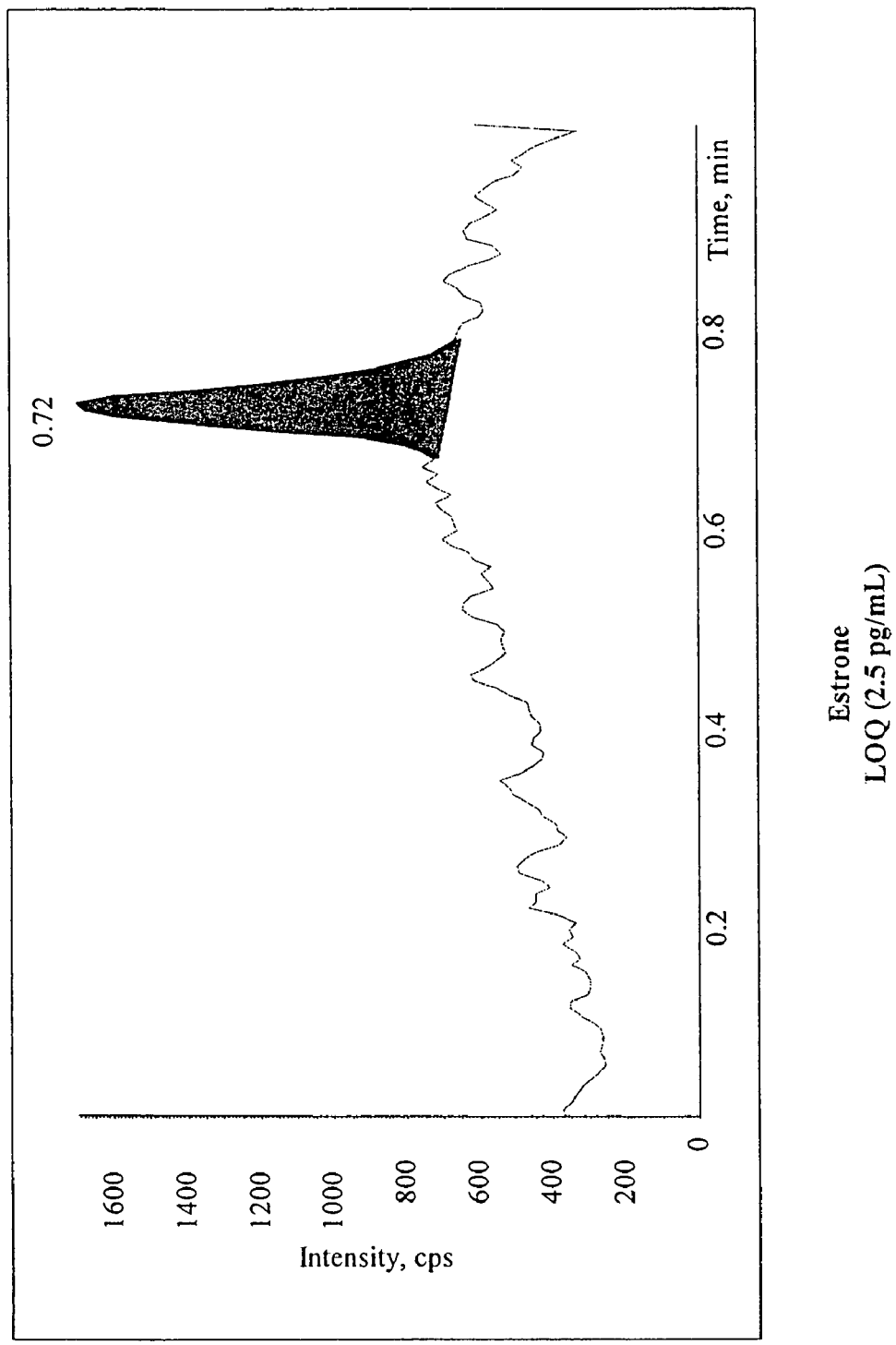

FIG. 12 shows a 2D-LC-MS/MS chromatogram of estrone at a limit of quantification of 2.5 pg/mL in accordance with one embodiment of the present invention.

Figure 13:
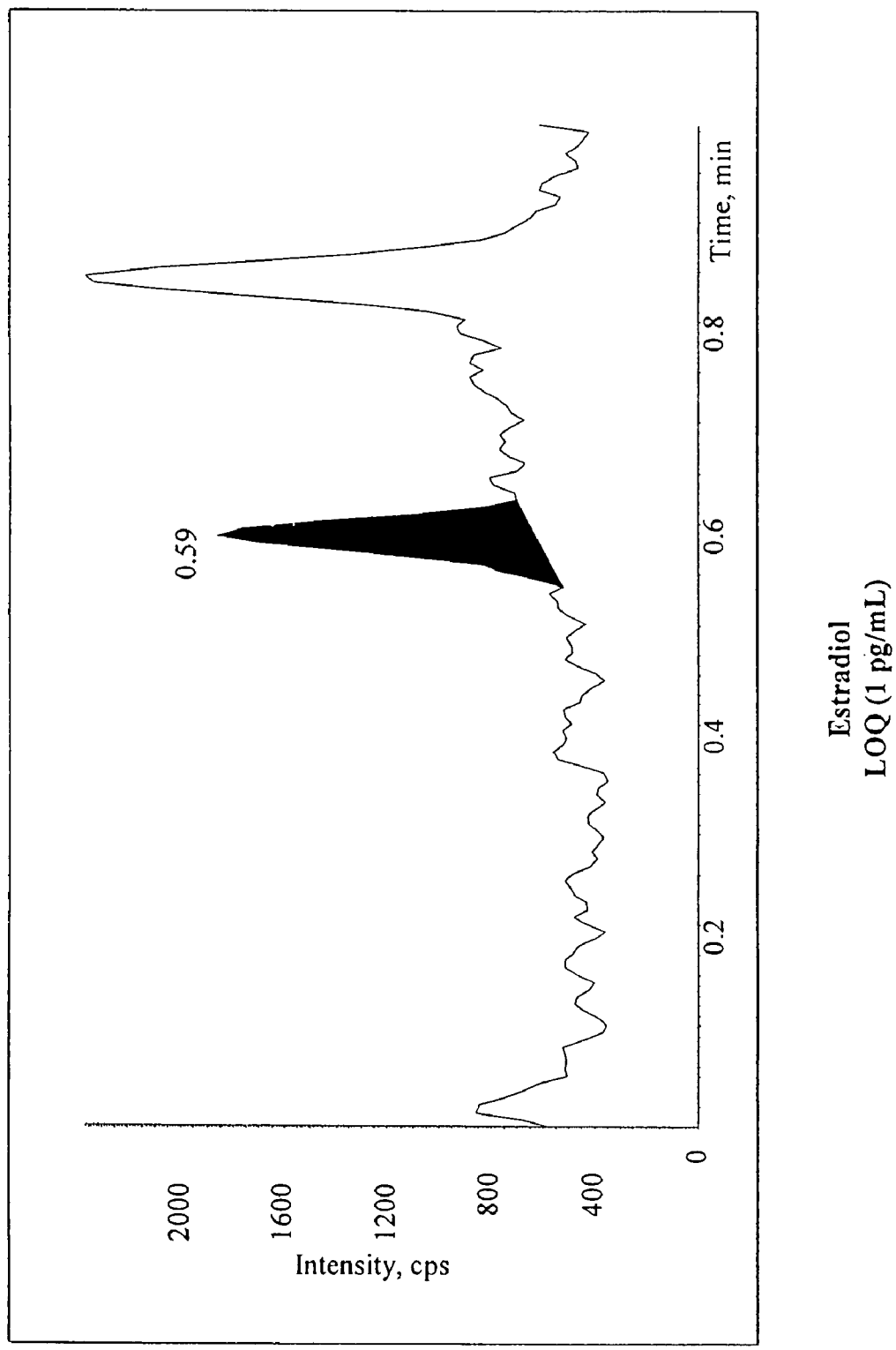

FIG. 13 shows a 2D-LC-MS/MS chromatogram of estradiol at a limit of quantification of 1 pg/mL in accordance with one embodiment of the present invention.

Figure 14:
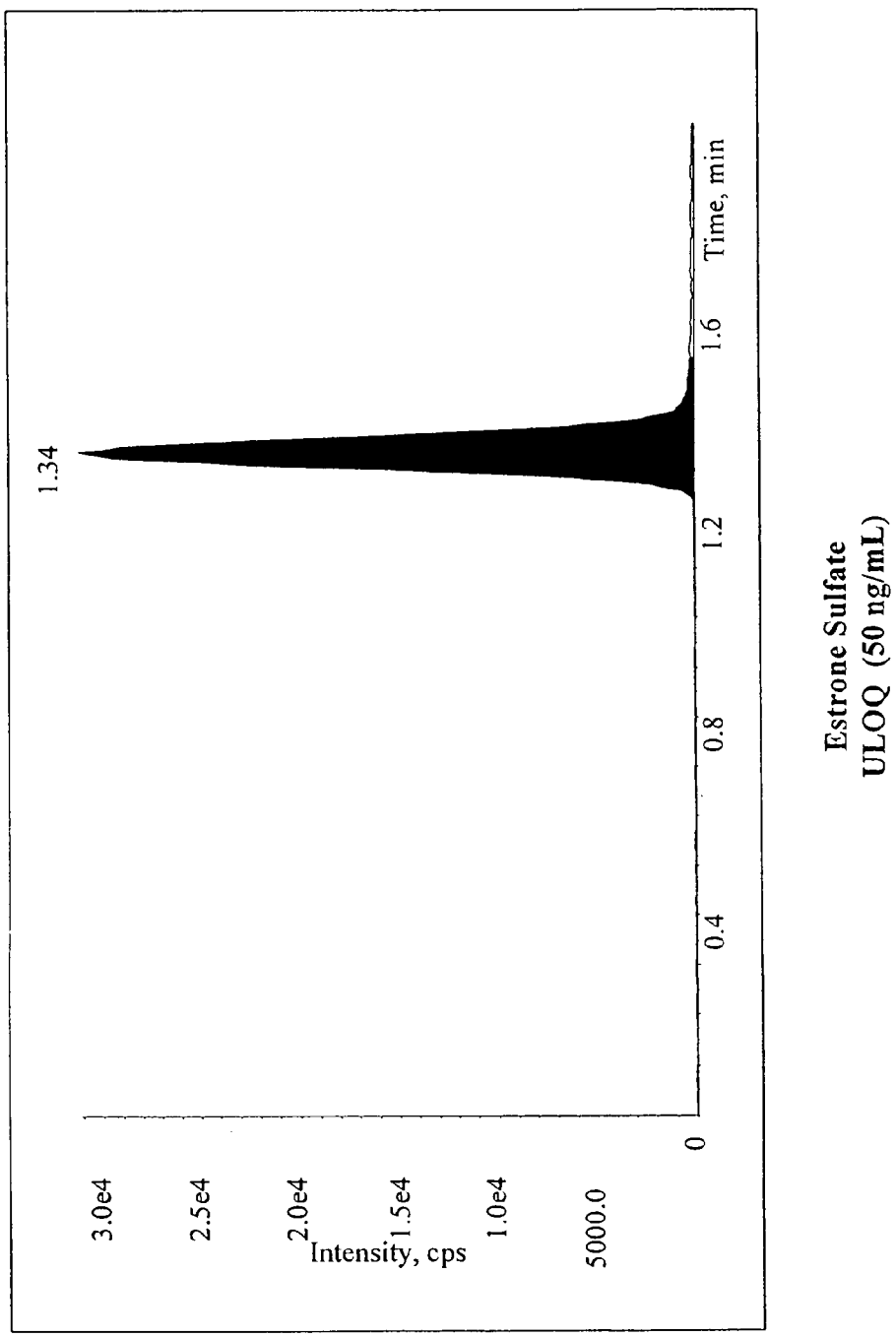

FIG. 14 shows a LC-MS/MS chromatogram of estrone sulfate at an upper limit of quantification of 50 ng/mL in accordance with one embodiment of the present invention.

Figure 15:
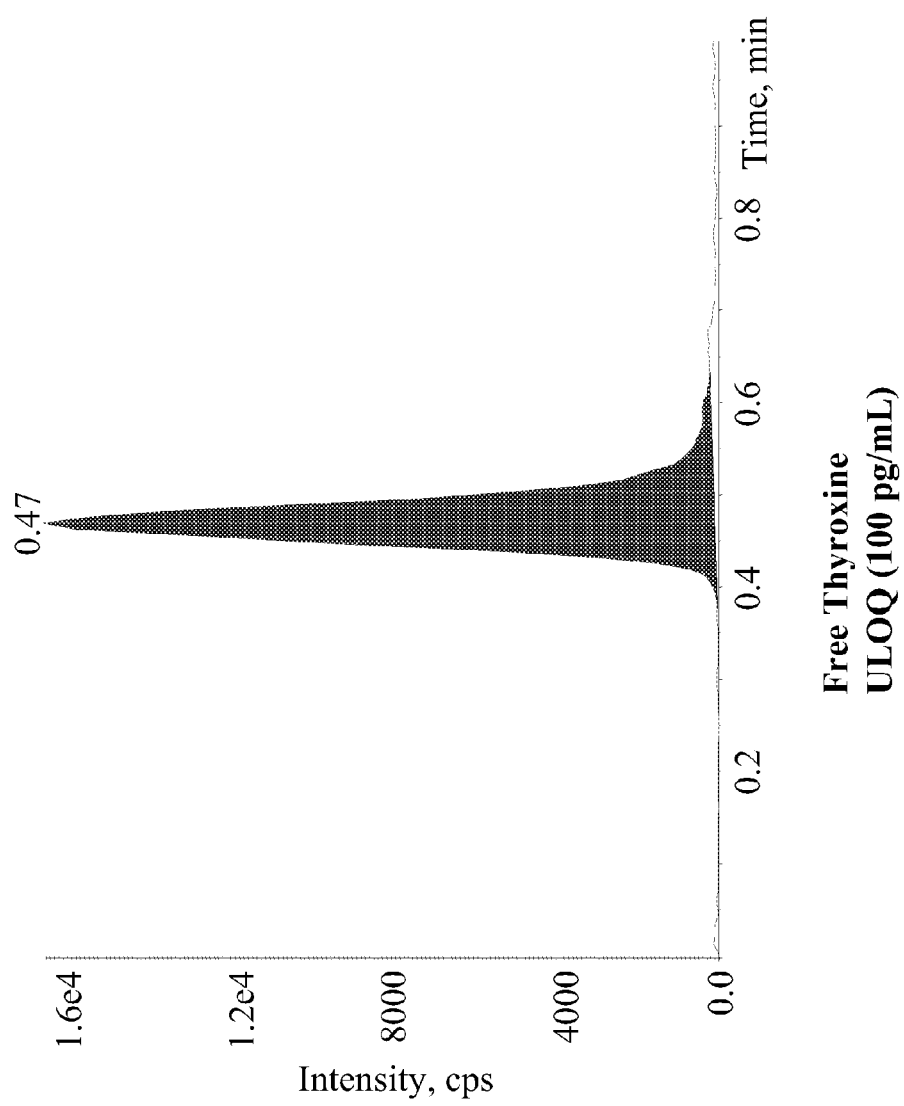

FIG. 15 shows a LC-MS/MS chromatogram of free thyroxine at an upper limit of quantification of 100 pg/dL in accordance with one embodiment of the present invention.

Figure 16:
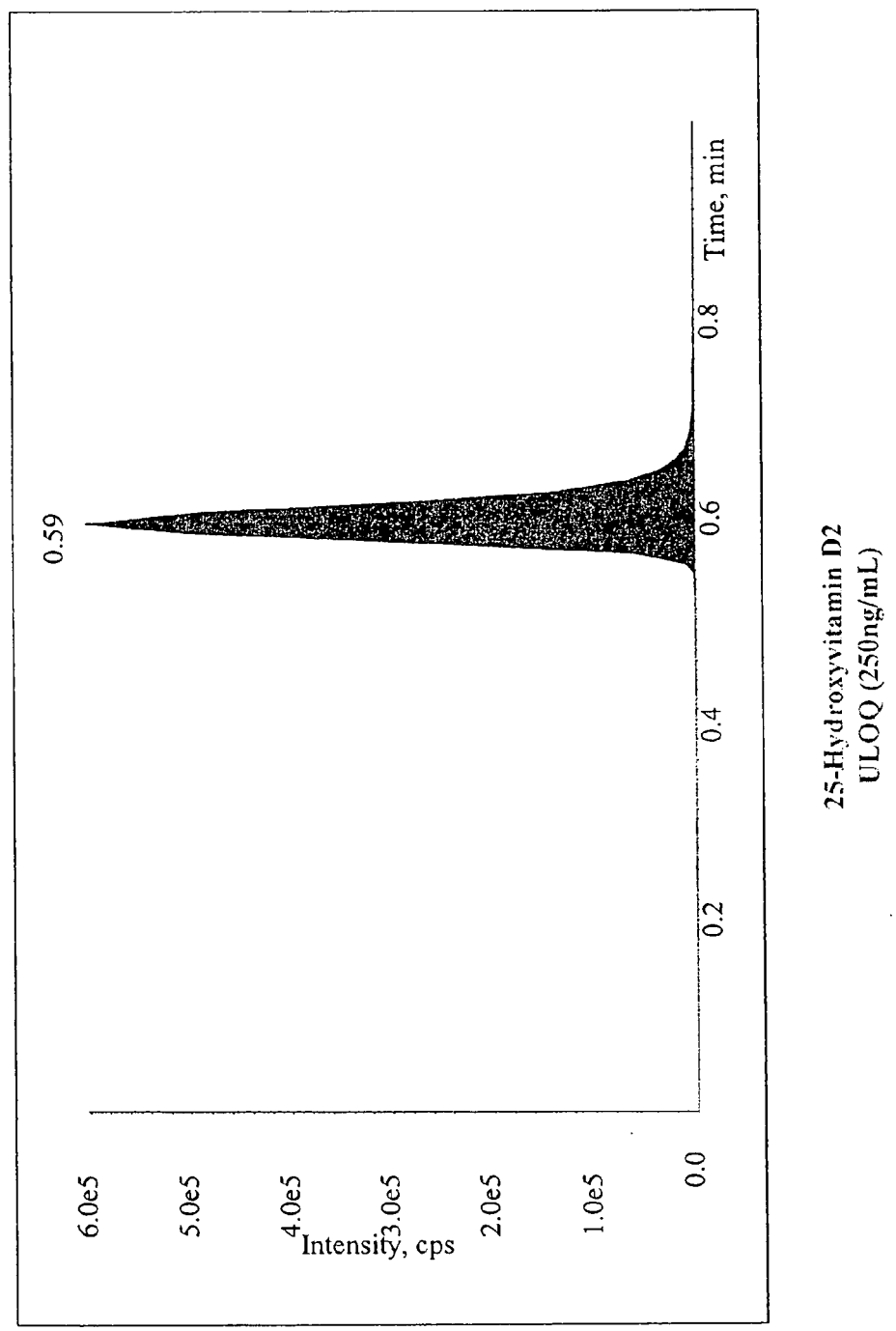

FIG. 16 shows a 2D-LC-MS/MS chromatogram of 25-hydroxyvitamin D2 at an upper limit of quantification of 250 ng/mL in accordance with one embodiment of the present invention.

Figure 17:
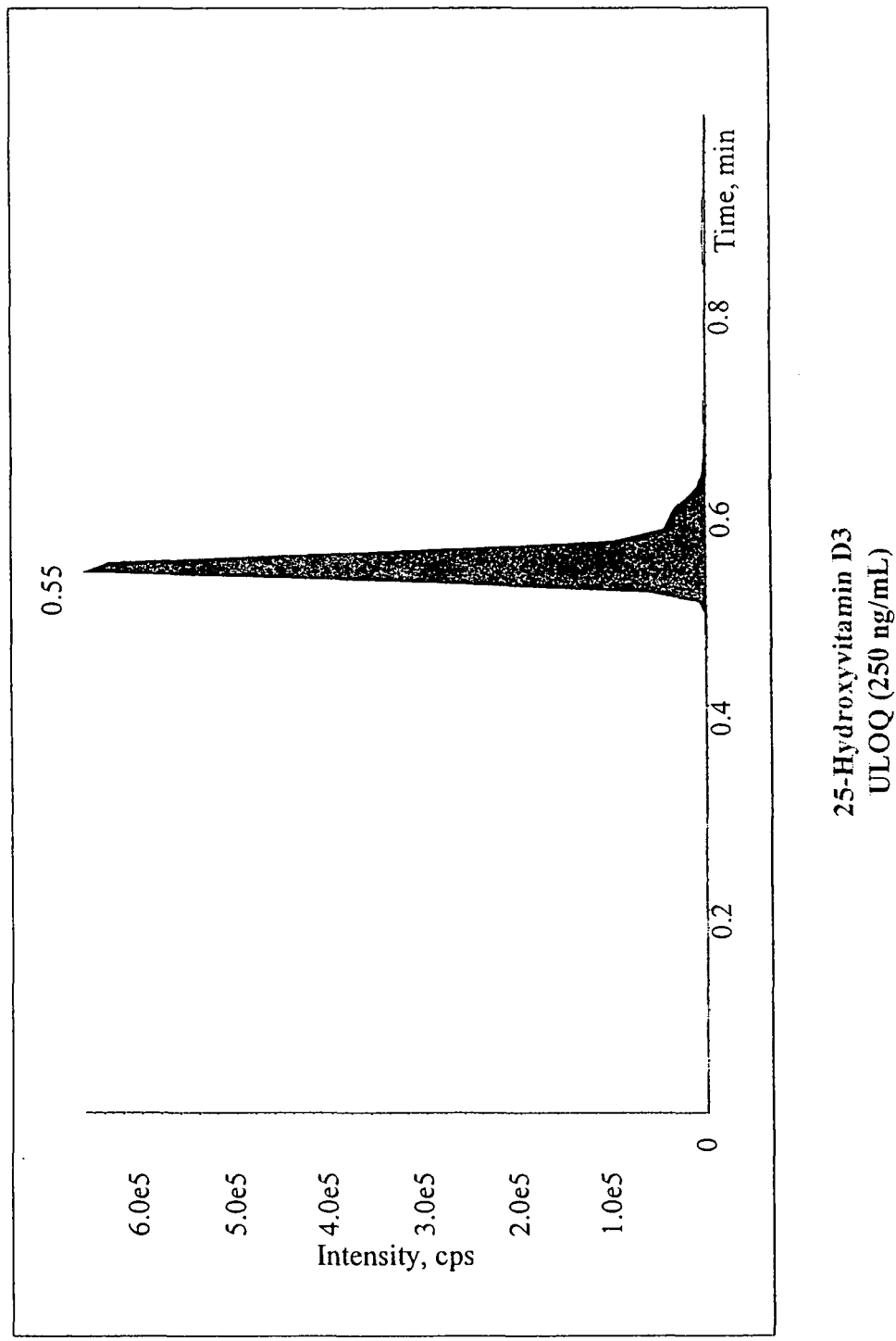

FIG. 17 shows a 2D-LC-MS/MS chromatogram of 25-hydroxyvitamin D3 at an upper limit of quantification of 250 ng/mL in accordance with one embodiment of the present invention.

Figure 18:
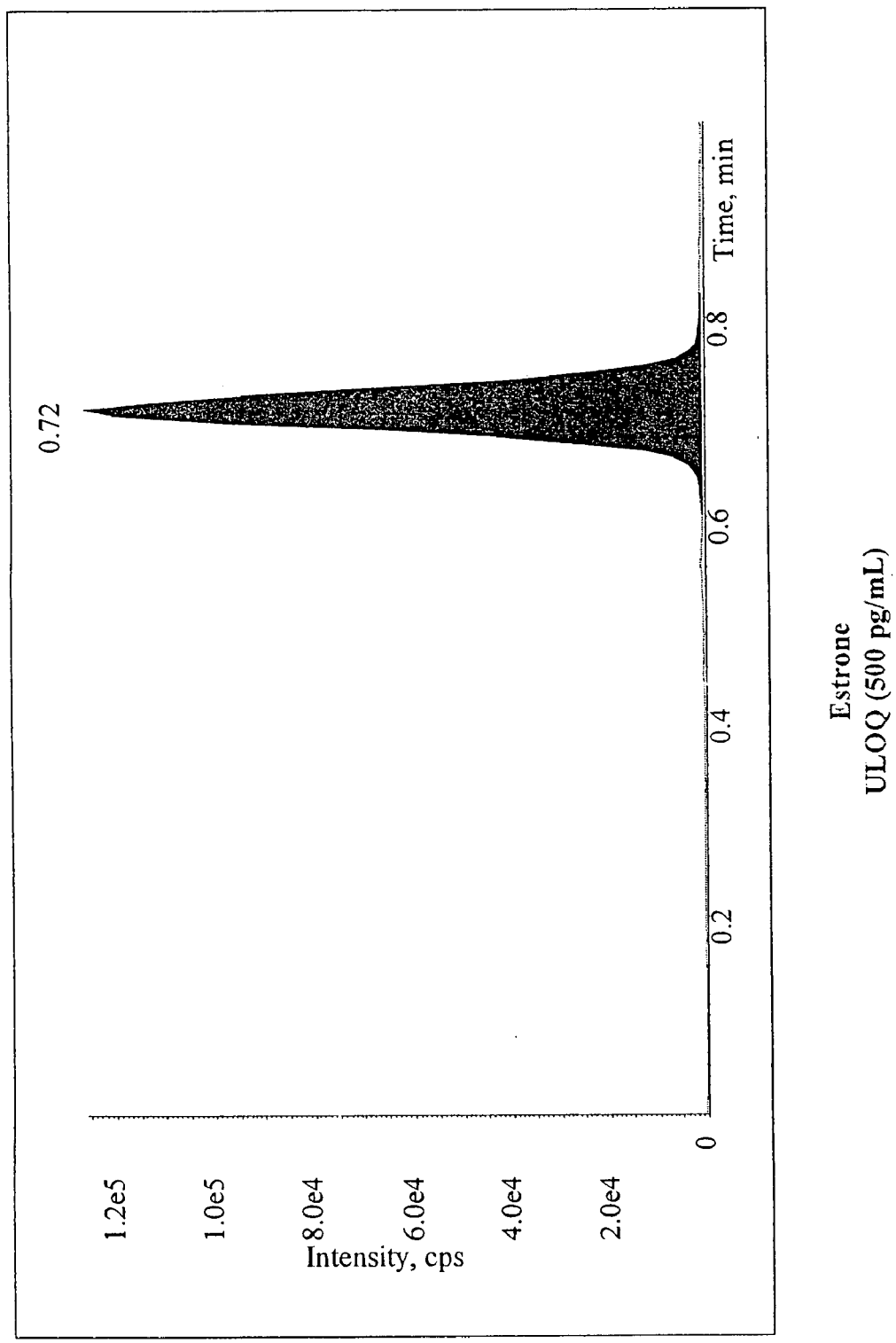

FIG. 18 shows a 2D-LC-MS/MS chromatogram of estrone at an upper limit of quantification of 500 pg/mL in accordance with one embodiment of the present invention.

Figure 19:
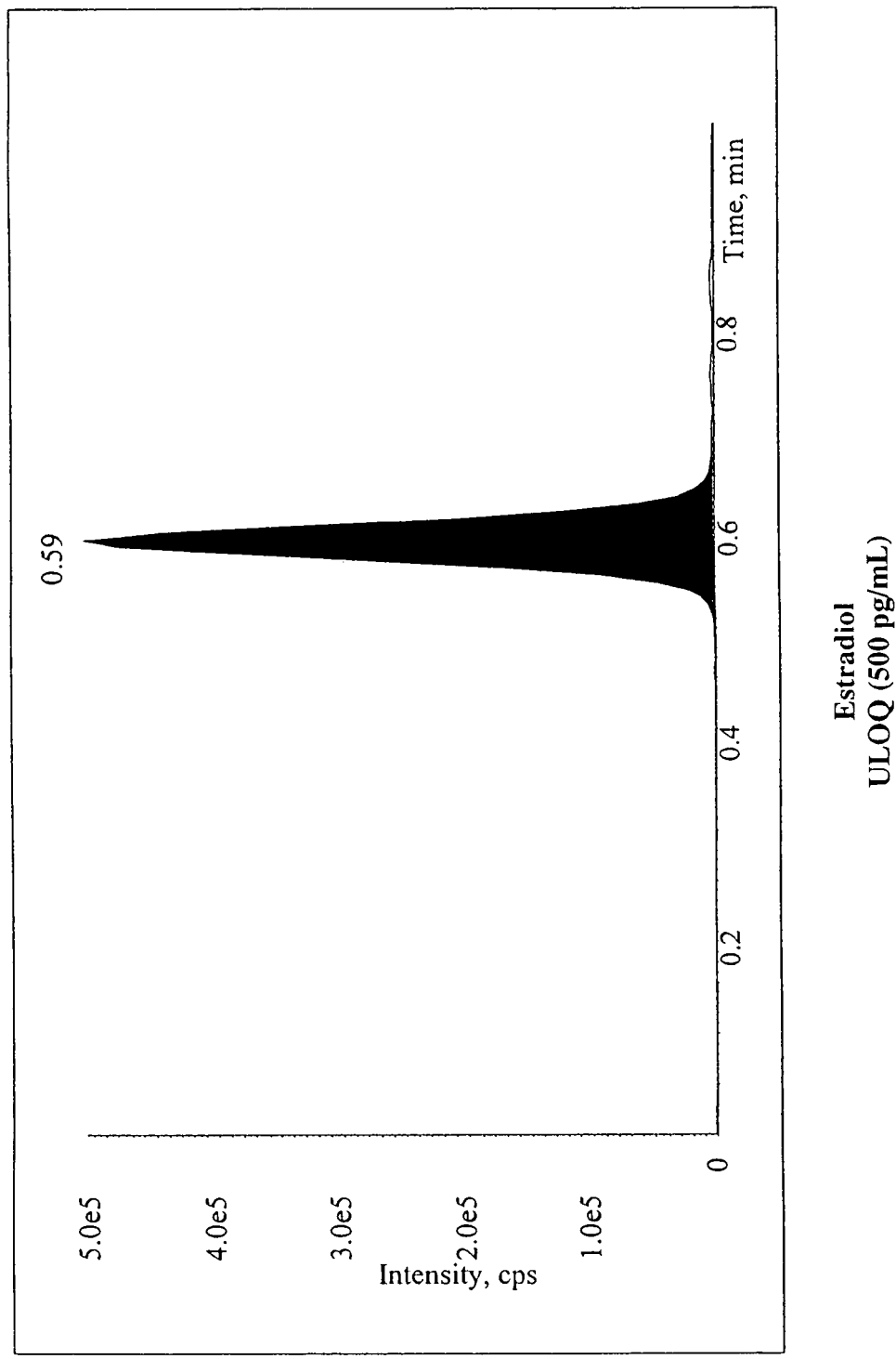

FIG. 19 shows a 2D-LC-MS/MS chromatogram of estradiol at an upper limit of quantification of 500 pg/mL in accordance with one embodiment of the present invention.

Figure 20:
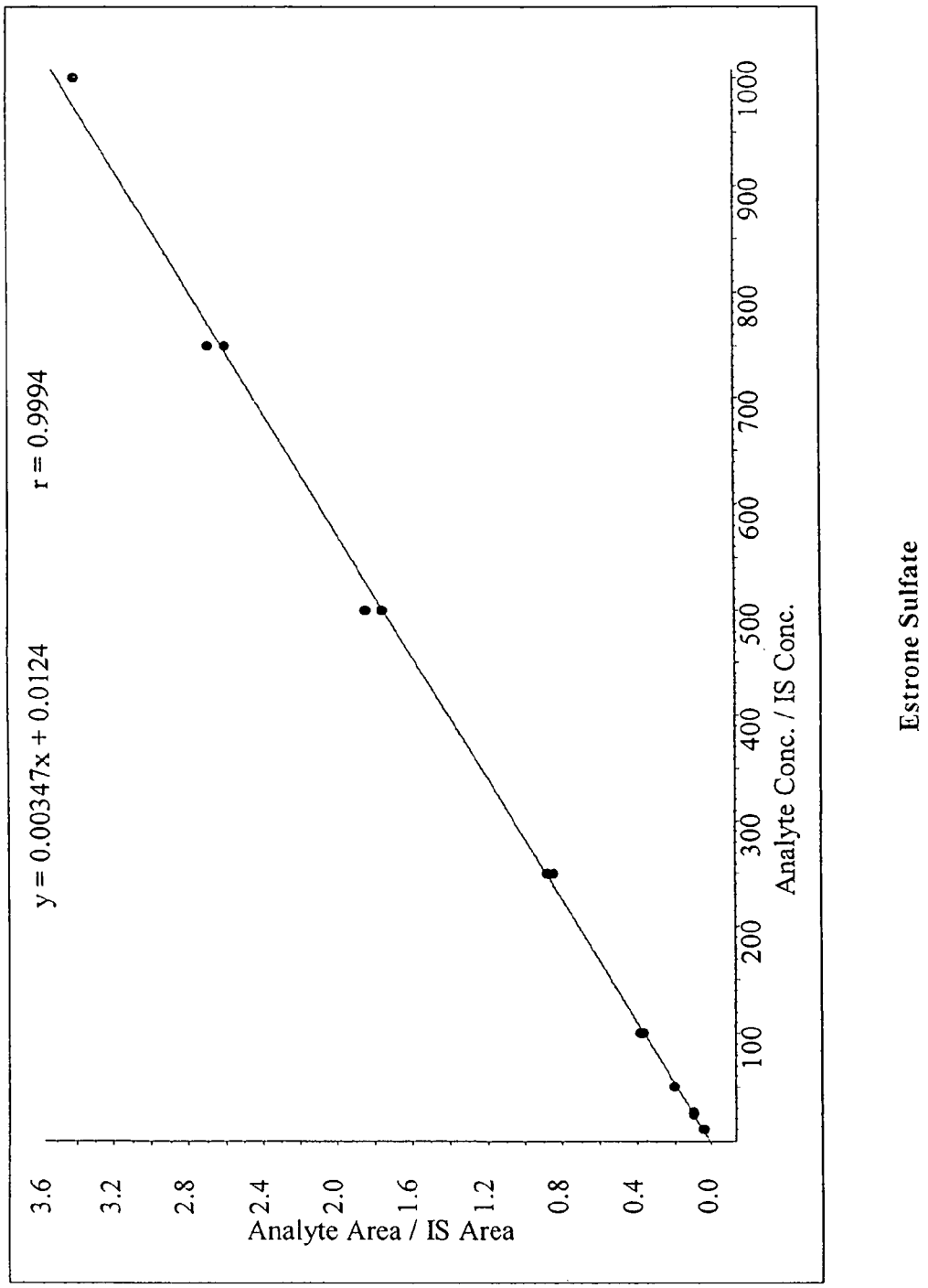

FIG. 20 shows a calibration curve obtained by LC-MS/MS for estrone sulfate in accordance with one embodiment of the present invention.

Figure 21:
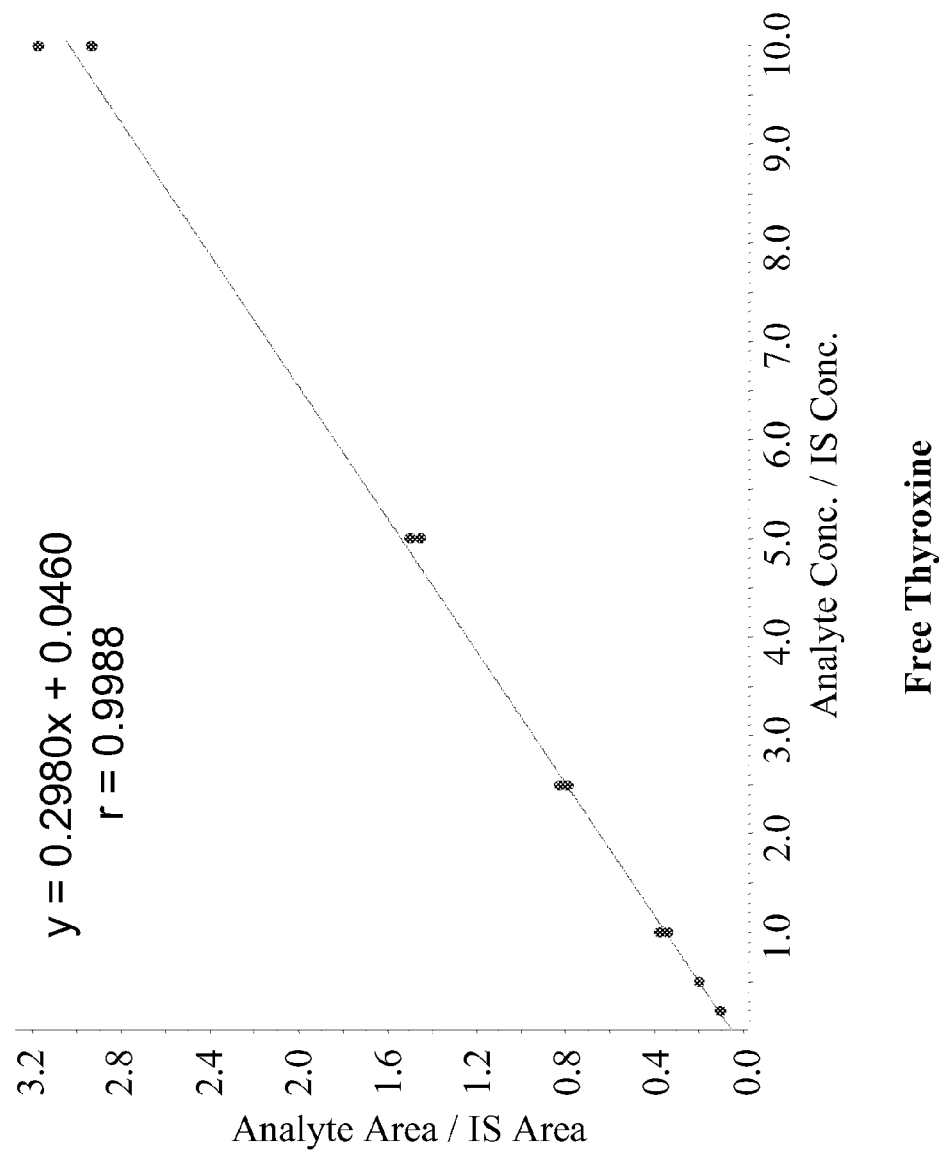

FIG. 21 shows a calibration curve obtained by LC-MS/MS for free thyroxine in accordance with one embodiment of the present invention.

Figure 22:
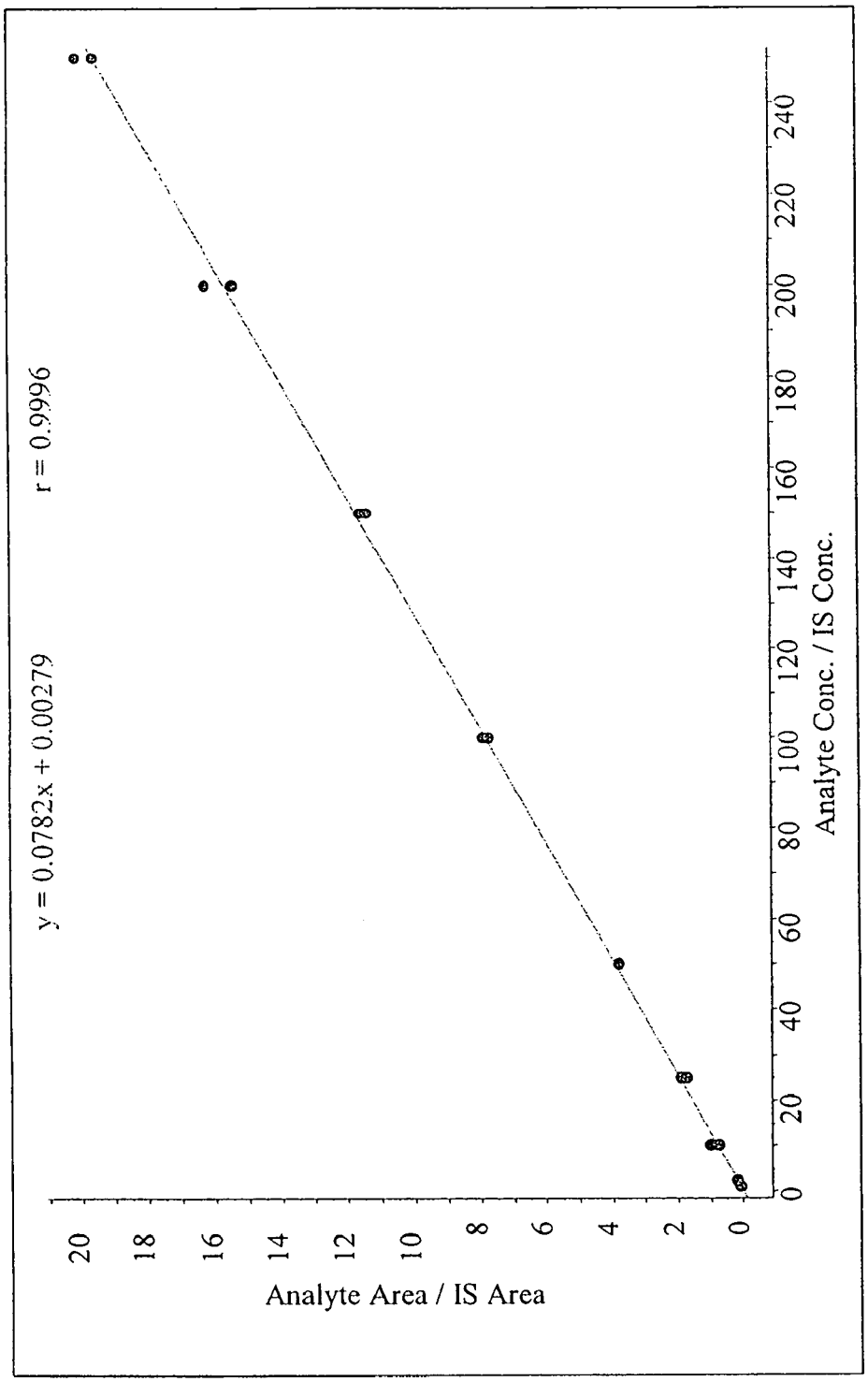

FIG. 22 shows a calibration curve obtained by 2D-LC-MS/MS for 25-hydroxyvitamin D2 in accordance with one embodiment of the present invention.

Figure 23:
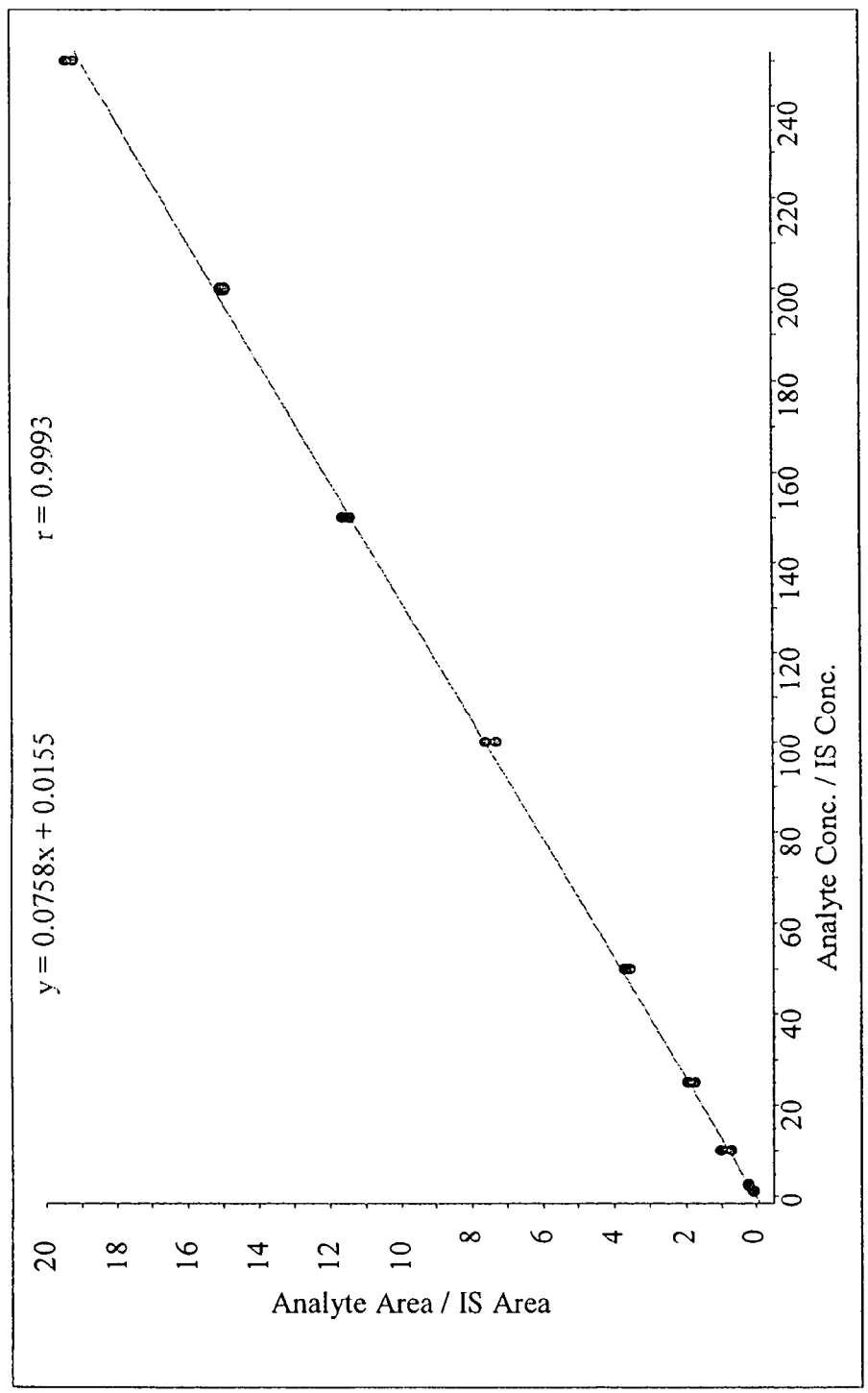

FIG. 23 shows a calibration curve obtained by 2D-LC-MS/MS for 25-hydroxyvitamin D3 in accordance with one embodiment of the present invention.

Figure 24:
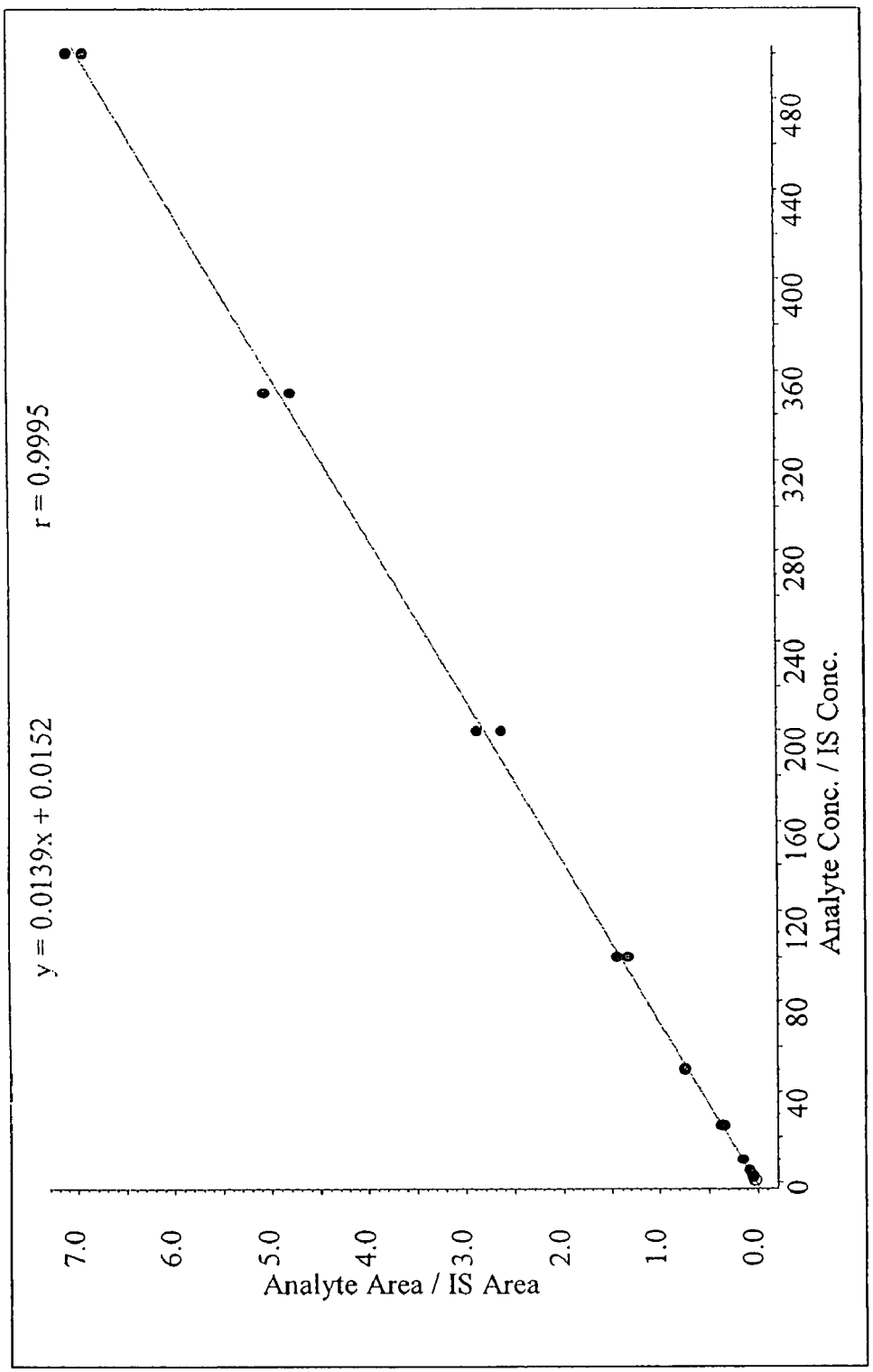

FIG. 24 shows a calibration curve obtained by 2D-LC-MS/MS for estrone in accordance with one embodiment of the present invention.

Figure 25:
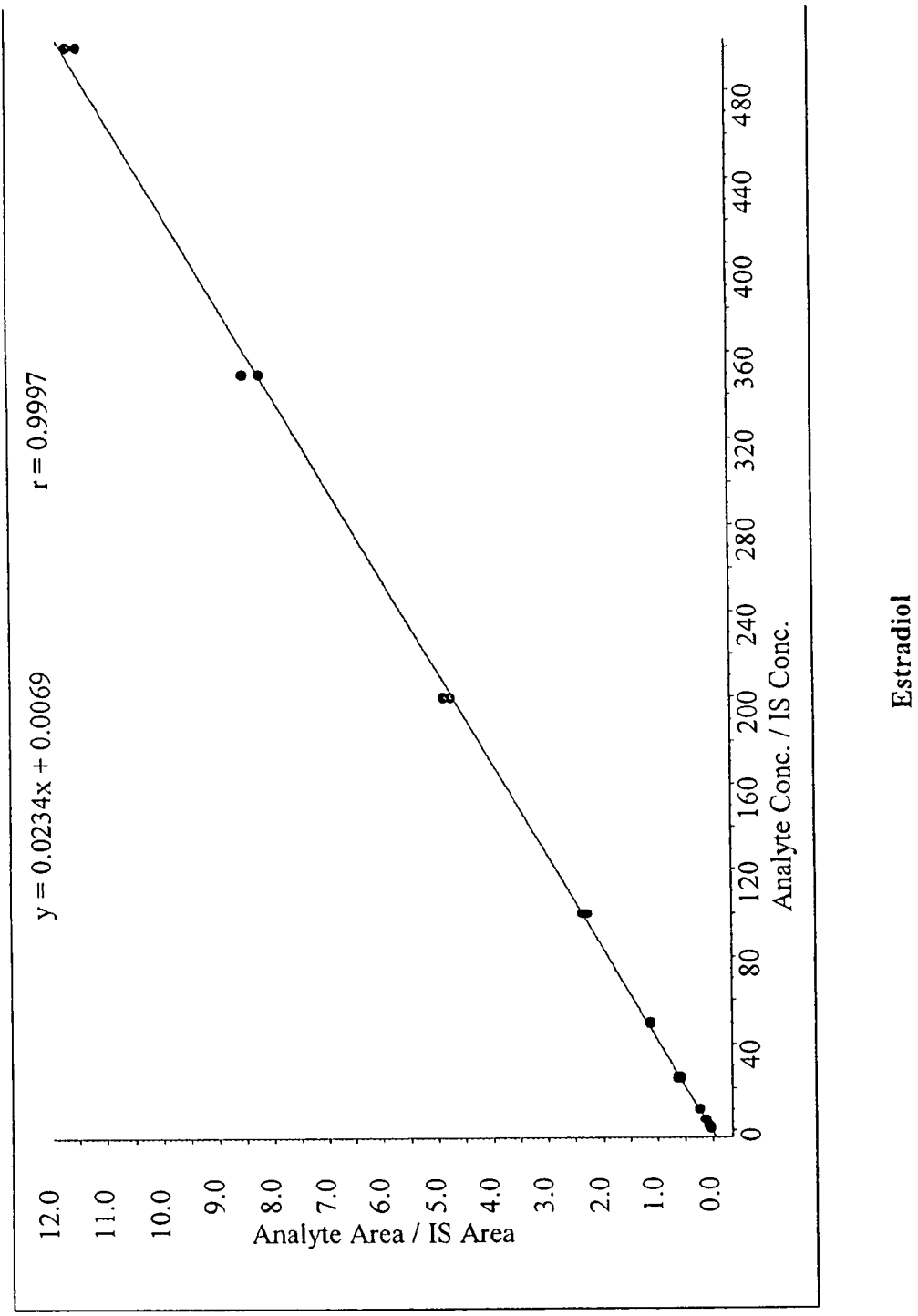

FIG. 25 shows a calibration curve obtained by 2D-LC-MS/MS for estradiol in accordance with one embodiment of the present invention.

Figure 26:
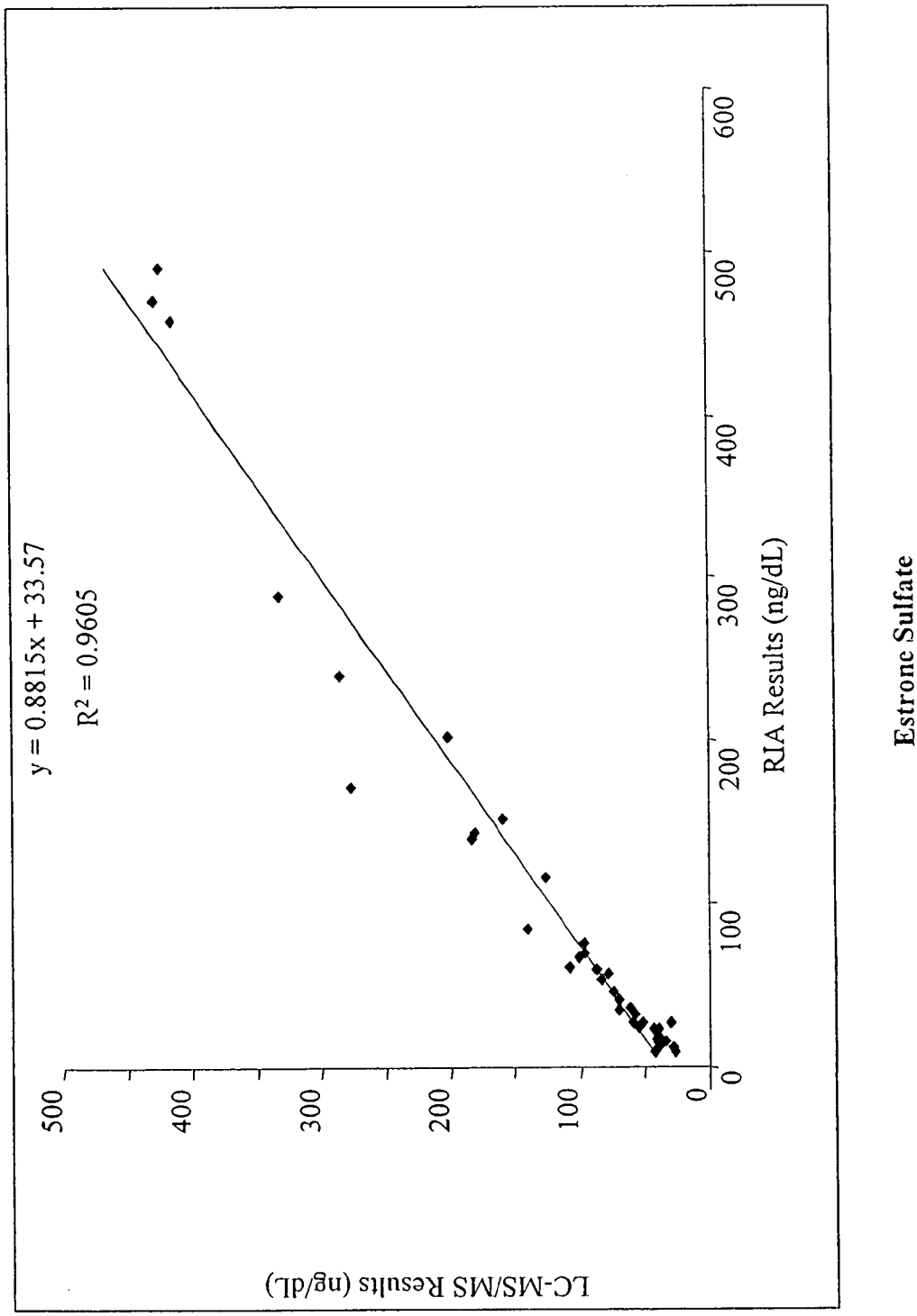

FIG. 26 shows cross-validation data for LC-MS/MS as compared to radioimmunoassay (RIA) for estrone sulfate in accordance with one embodiment of the present invention.

Figure 27:
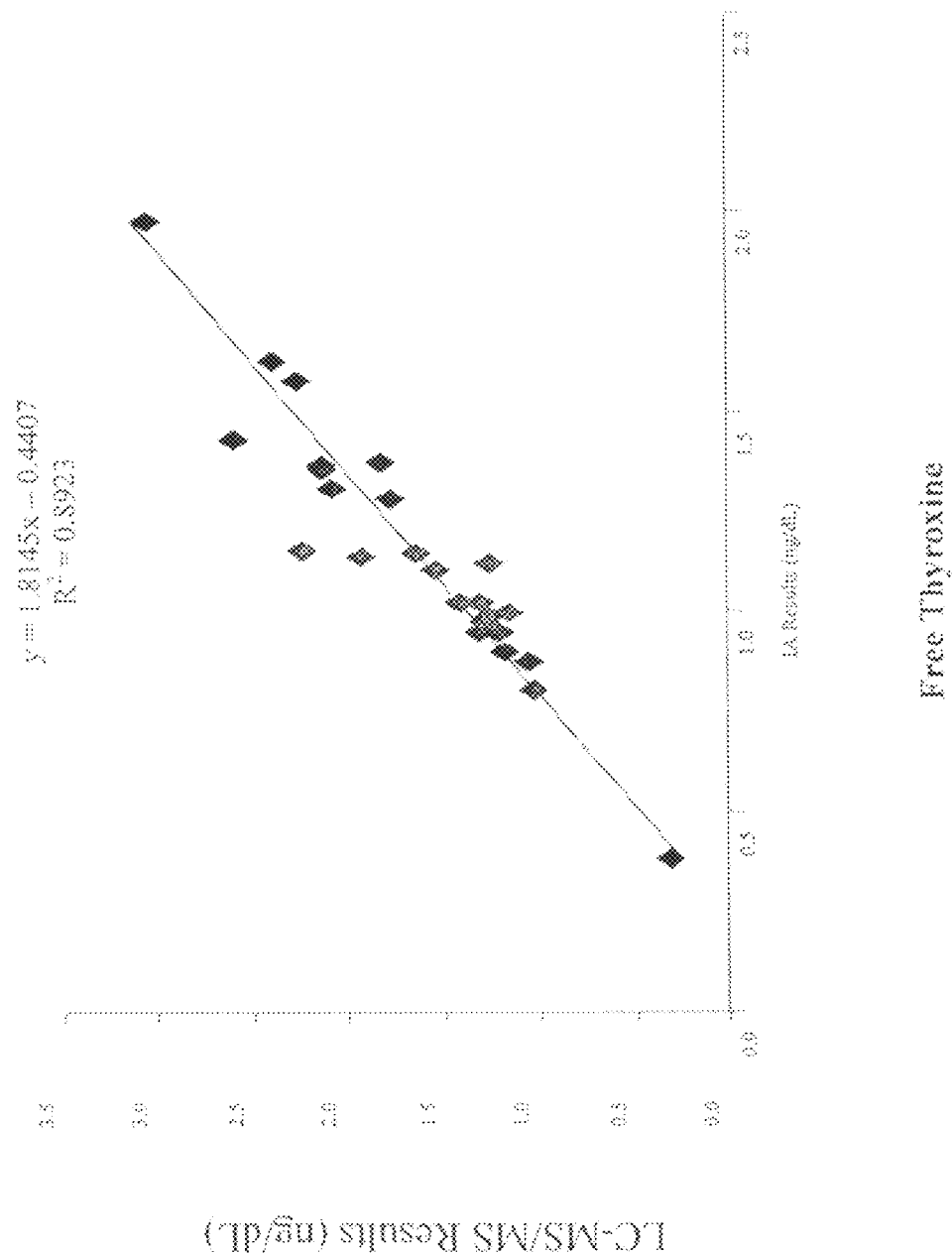

FIG. 27 shows cross-validation data for LC-MS/MS as compared to immunoassay (IA) for free thyroxine in accordance with one embodiment of the present invention.

Figure 28A:
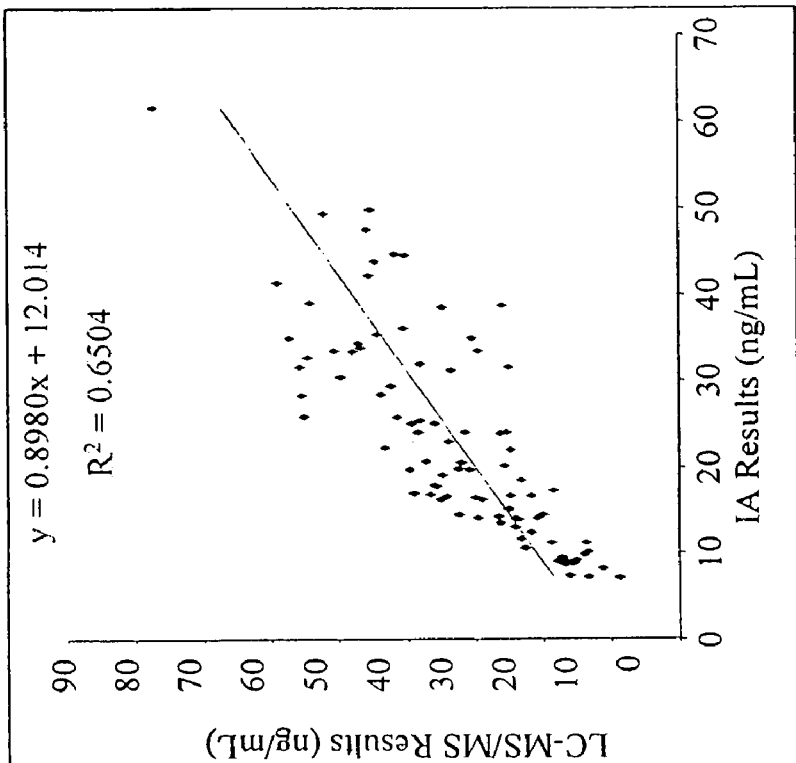
Figure 28B:
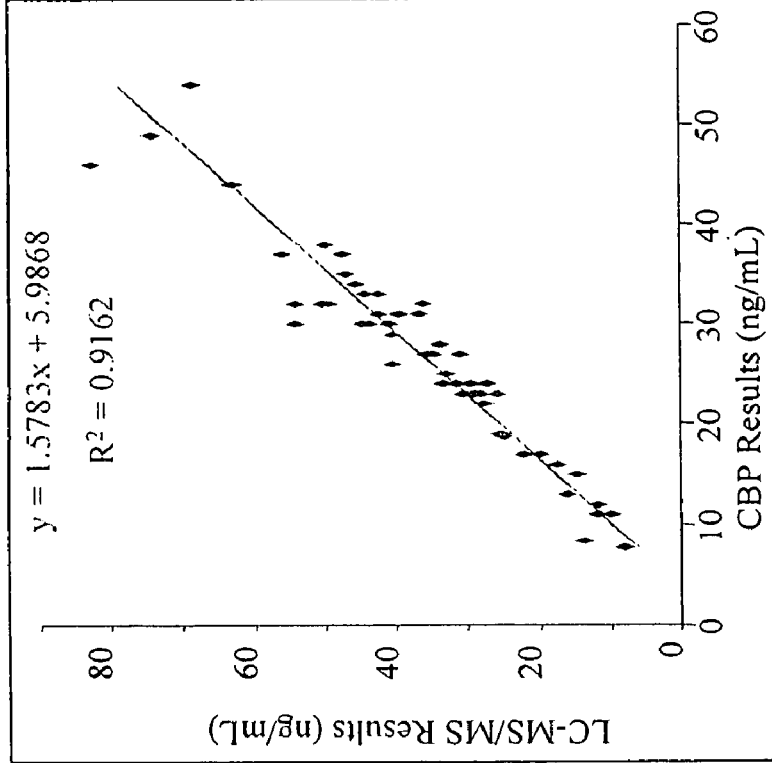

FIG. 28 shows cross-validation data for 2D-LC-MS/MS as compared to a competitive binding protein assay (CBP) (Panel A) or immunoassay (IA) (Panel B) for total 25-hydroxyvitamin D (25-hydroxyvitamin D2+D3) in accordance with alternate embodiments of the present invention.

Figure 29:
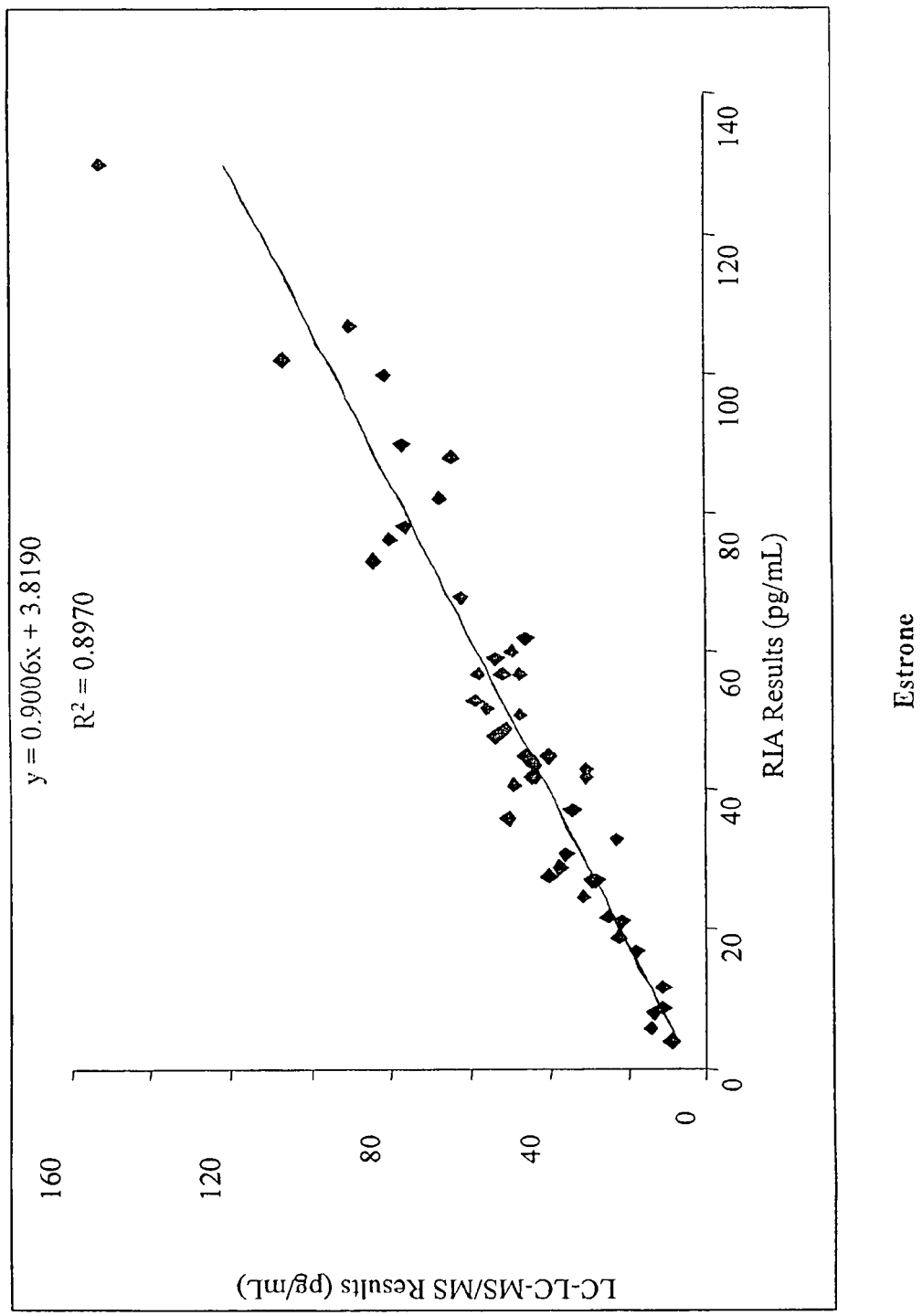

FIG. 29 shows cross-validation data for 2D-LC-MS/MS as compared to RIA for Estrone in accordance with one embodiment of the present invention.

Figure 30:
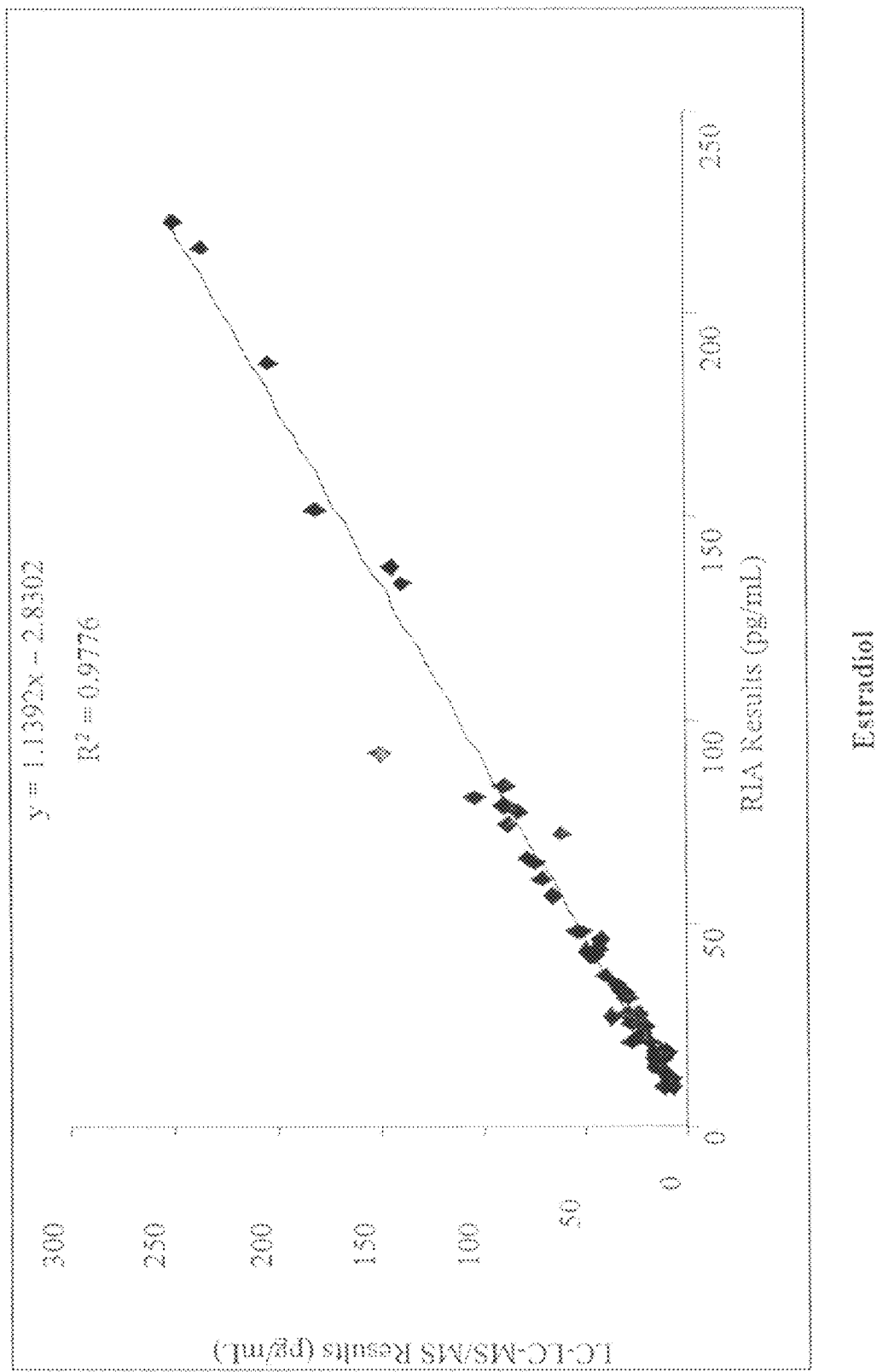

FIG. 30 shows cross-validation data for 2D-LC-MS/MS as compared to RIA for Estradiol in accordance with one embodiment of the present invention.

Figure 31:
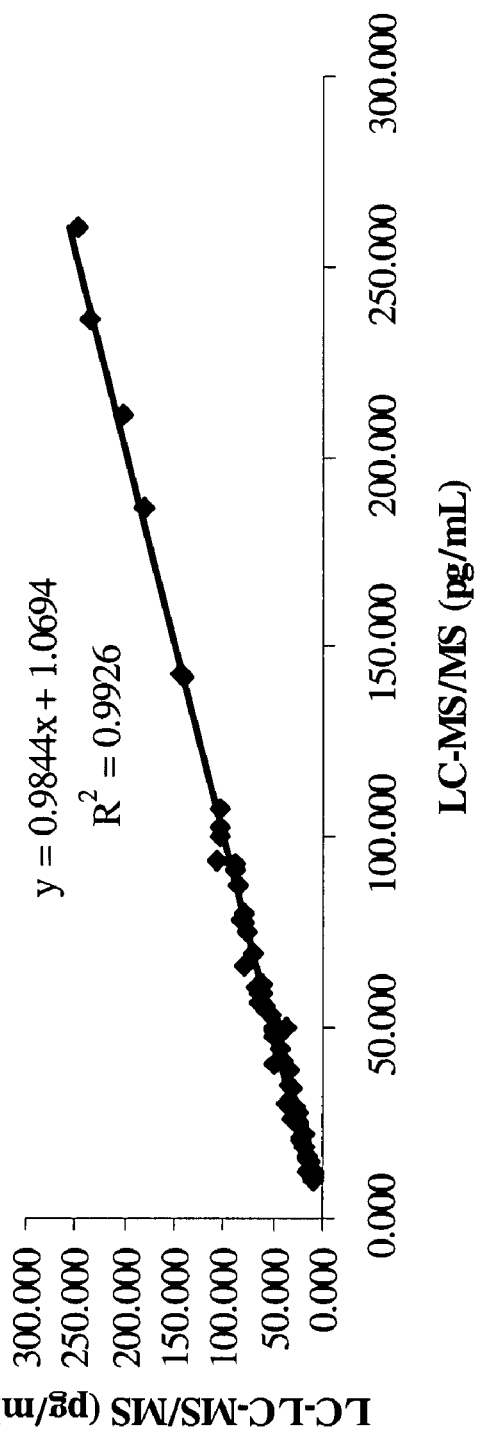

FIG. 31 shows a comparison of Estradiol (E2) cross-validation of LC-MS/MS with derivatization to 2D-LC-MS/MS without derivatization in accordance with an embodiment of the present invention.

Figure 32:
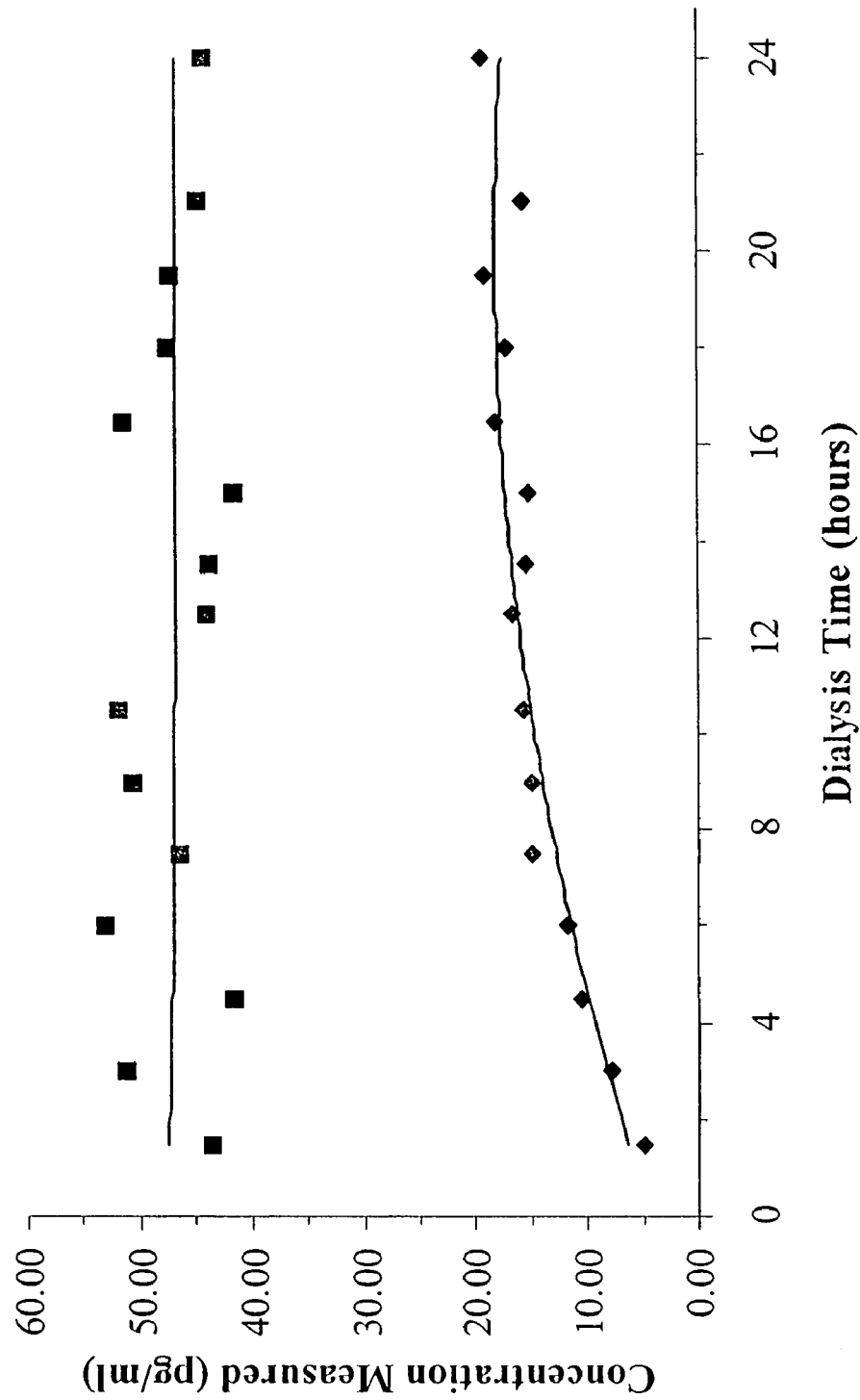

FIG. 32 shows the measured concentration (pg/mL) of free thyroxine vs. dialysis time (hours). The squares (■) show dialysis losses and the diamonds (♦) show effective dialysis for free thyroxine using 96-well equilibrium dialysis plates in accordance with one embodiment of the present invention.

DETAILED DESCRIPTION

The presently disclosed subject matter now will be described more fully hereinafter with reference to the accompanying description and drawings, in which some, but not all embodiments of the presently disclosed subject matter are shown. The presently disclosed subject matter can be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation. The disclosure utilizes the abbreviations shown below.

Abbreviations

APCI=atmospheric pressure chemical ionization
CBP=competitive binding protein
E1=Estrone
E2=17B-Estradiol or Estradiol
FT4=Free Thryoxine

Abbreviations

HTLC=high turbulence (throughput) liquid chromatography
HPLC=high performance liquid chromatography
LLE=liquid-liquid extraction
LOQ=limits of quantification
LLOQ=lower limit of quantification
IA=immunoassay
ELISA=enzyme linked immunoassay
RIA=radioimmunoassay
SST=system suitability test
ULOQ=upper limit of quantification
2D-LC-MS/MS=two-dimensional liquid chromatography hyphenated to tandem mass spectrometry
(LC)-LC-MS/MS=two-dimensional liquid chromatography tandem hyphenated to mass spectrometry
(LC)-MS/MS=liquid chromatography hyphenated to tandem mass spectrometry

Definitions

While the following terms are believed to be well understood by one of ordinary skill in the art, the following definitions are set forth to facilitate explanation of the presently disclosed subject matter. Other definitions are found throughout the specification. Unless otherwise defined, all technical and scientific terms used herein have the same meaning as commonly understood by one of ordinary skill in the art to which this presently described subject matter belongs.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

The terms "a", "an", and "the" refer to "one or more" when used in this application, including the claims. Thus, for example, reference to "a cell" includes a plurality of such cells, unless the context clearly is to the contrary (e.g., a plurality of cells), and so forth.

As used herein, the term "biomarker" is any biomolecule that may provide biological information about the physiological state of an organism. In certain embodiments, the presence or absence of the biomarker may be informative. In other embodiments, the level of the biomarker may be informative. A biomarker may be a hormone, such as an estrogen (e.g., estradiol, estrone), testosterone, thyroxine (T4), triiodothyronine (T3), or a metabolite of a hormone (estrogen sulfate). A biomarker may also be a vitamin or a metabolite of a vitamin. For example, in one embodiment, the measured biomarker may comprise a vitamin D compound such as 25-hydroxyvitamin D2 and 25-hydroxyvitamin D3.

As used herein, the terms "purify" or "separate" or derivations thereof do not necessarily refer to the removal of all materials other than the analyte(s) of interest from a sample matrix. Instead, in some embodiments, the terms "purify" or "separate" refer to a procedure that enriches the amount of one or more analytes of interest relative to one or more other components present in the sample matrix. In some embodiments, a "purification" or "separation" procedure can be used to remove one or more components of a sample that could interfere with the detection of the analyte, for example, one or more components that could interfere with detection of an analyte by mass spectrometry.

As used herein, "derivatizing" means reacting two molecules to form a new molecule. Derivatizing agents may include isothiocyanate groups, dansyl groups, dinitro-fluorophenyl groups, nitrophenoxycarbonyl groups, and/or phthalaldehyde groups.

As used herein, "chromatography" refers to a process in which a chemical mixture carried by a liquid or gas is separated into components as a result of differential distribution of the chemical entities as they flow around or over a stationary liquid or solid phase.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties such as the biomarker analytes quantified in the experiments herein. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In the method, the sample (or pre-purified sample) may be applied to the column at the inlet port, eluted with a solvent or solvent mixture, and discharged at the outlet port. Different solvent modes may be selected for eluting different analytes of interest. For example, liquid chromatography may be performed using a gradient mode, an isocratic mode, or a polytyptic (i.e. mixed) mode. In one embodiment, HPLC may performed on a multiplexed analytical HPLC system with a C18 solid phase using isocratic separation with water:methanol as the mobile phase.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having an average diameter of about 5 μm. In some embodiments, the analytical column is a functionalized silica or polymer-silica hybrid, or a polymeric particle or monolithic silica stationary phase, such as a phenyl-hexyl functionalized analytical column.

Analytical columns can be distinguished from "extraction columns," which typically are used to separate or extract retained materials from non-retained materials to obtained a "purified" sample for further purification or analysis. In some embodiments, the extraction column is a functionalized silica or polymer-silica hybrid or polymeric particle or monlithic silica stationary phase, such as a Poroshell SBC-18 column.

The term "heart-cutting" refers to the selection of a region of interest in a chromatogram and subjecting the analytes eluting within that region of interest to a second separation, e.g., a separation in a second dimension.

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g. ammonia) is subjected to electron impact, and analyte ions are formed by the interaction of reagent gas ions and analyte molecules.

The term "field desorption" as used herein refers to methods in which a non-volatile test sample is placed on an ionization surface, and an intense electric field is used to generate analyte ions.

The term "matrix-assisted laser desorption ionization," or "MALDI" as used herein refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

The term "surface enhanced laser desorption ionization," or "SELDI" as used herein refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization," or "ESI," as used herein refers to methods in which a solution is passed along a short length of capillary tube, to the end of which is applied a high positive or negative electric potential. Upon reaching the end of the tube, the solution may be vaporized (nebulized) into a jet or spray of very small droplets of solution in solvent vapor. This mist of droplet can flow through an evaporation chamber which is heated slightly to prevent condensation and to evaporate solvent. As the droplets get smaller the electrical surface charge density increases until such time that the natural repulsion between like charges causes ions as well as neutral molecules to be released.

The term "Atmospheric Pressure Chemical Ionization," or "APCI," as used herein refers to mass spectroscopy methods that are similar to ESI, however, APCI produces ions by ion-molecule reactions that occur within a plasma at atmospheric pressure. The plasma is maintained by an electric discharge between the spray capillary and a counter electrode. Then, ions are typically extracted into a mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" ("APPI") as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+(see e.g., Robb et al., 2000, Anal. Chem. 72(15): 3653-3659).

The term "inductively coupled plasma" as used herein refers to methods in which a sample is interacted with a partially ionized gas at a sufficiently high temperature to atomize and ionize most elements.

The term "ionization" and "ionizing" as used herein refers to the process of generating an analyte ion having a net electrical charge equal to one or more electron units. Negative ions are those ions having a net negative charge of one or more electron units, while positive ions are those ions having a net positive charge of one or more electron units.

The term "desorption" as used herein refers to the removal of an analyte from a surface and/or the entry of an analyte into a gaseous phase.

As used herein, the term "immunoassay" (IA) refers to a method for measuring the amount of an analyte of interest by quantifying the binding, or the inhibition of binding, of a substance to an antibody. Where an enzyme is used to detect the amount of binding of the substance (e.g. antigen) to an antibody, the assay is an enzyme-linked immunoassay (ELISA). As used herein, the term "radioimmunoassay" (RIA) refers to a method for measuring the amount of an analyte of interest by quantifying the binding, or the inhibition, of binding, of a radiolabled substance to an antibody.

As used herein, the term "hemolysed" refers to the rupturing of the red blood cell membrane, which results in the release of hemoglobin and other cellular contents into the plasma or serum and the term "lipemic" refers to an excess of fats or lipids in blood.

Analysis of Biomarkers by LC-MS/MS

Thus, embodiments of the present invention relate to methods and systems for the quantitative analysis of endogenous biomarkers for clinical diagnosis. The present invention may be embodied in a variety of ways.

In one embodiment, the present invention comprises a method for determining the presence or amount of at least one biomarker of interest in a biological sample, the method comprising: providing a biological sample believed to contain at least one biomarker of interest; chromatographically separating the at least one biomarker of interest from other components in the sample; and analyzing the chromatographically separated at least one biomarker of interest by mass spectrometry to determine the presence or amount of the at least one biomarker of interest in the sample.

In an embodiment, the at least one biomarker comprises a steroid hormone or a thyroid hormone. For example, in one embodiment, the at least one biomarker comprises estradiol and estrone. Or, the at least one biomarker may comprise free thyroxine (T4) or triiodothyronine (T3).

In certain embodiments, the chromatography may comprise high performance liquid chromatography (HPLC). In an embodiment, the chromatography may comprises extraction and/or analytical liquid chromatography.

In an embodiment, the method may comprise purifying the biomarker of interest prior to chromatography. For example, the sample may be partially purified by at least one of liquid-liquid extraction. Also, the method may comprise the step of diluting the sample into a solvent or solvents used for LS and/or MS.

In some embodiments, the method may comprise the use of two liquid chromatography steps. For example, in certain embodiments, the method for determining the presence or amount of one or more biomarkers in a test sample may comprise the steps of: (a) providing a sample suspected of containing one or more biomarkers of interest; (b) partially purifying the one or more biomarkers of interest from other components in the sample by at least one of liquid-liquid extraction or by diluting the sample; (c) transferring the extracted one or more hormones or metabolites onto an extraction column (i.e., on-line or off-line); (d) transferring the one or more biomarkers of interest from the extraction column onto an analytical column and chromatographically separating the one or more biomarkers of interest from other components in the sample; and (e) analyzing the chromatographically separated biomarkers of interest by mass spectrometry to determine the presence or amount of the one or more biomarkers in the test sample.

In certain embodiments, the present invention comprises methods for measuring at least one of estradiol and/or estrone in a sample. In certain embodiments, the estradiol is dehydrated to reduce the complexity of the MS/MS spectrum, such that the sensitivity of estradiol detection is increased. For example, in one embodiment, the present invention comprises a method for determining the presence or amount of estradiol in a sample by tandem mass spectrometry, comprising: (a) generating a dehydrated precursor ion of the estradiol; (b) generating one or more fragment ions of the precursor ion; and (c) detecting the presence or amount of one or more of the ions generated in step (a) or (b) or both, and relating the detected ions to the presence or amount of the estradiol in the sample.

In an embodiment, the sample may be subjected to a purification step prior to ionization. For example, in certain embodiments, the purification step may comprises chromatography. As discussed herein, in certain embodiments, the chromatography comprises high performance liquid chromatography (HPLC). The LC step may comprise one LC separation, or multiple LC separations. In one embodiment, the chromatographic separation comprises extraction and analytical liquid chromatography. Additionally or alternatively, high turbulence liquid chromatography (HTLC) (also known as high throughput liquid chromatography) may be used.

The purification may comprise steps in addition to HPLC or other types of chromatographic separation techniques. In alternate embodiments, the method may comprise at least one of liquid-liquid extraction or dilution. In one embodiment, the sample is diluted into a solvent or solvent mixture that may be used for LC and/or MS (e.g., LC-MS/MS or 2D-LC-MS/MS).

In an embodiment, the treatment of estradiol to form a dehydrated form of the compound reduces the molecular weight of the estradiol by about 18 mass units. Thus, in an embodiment, the precursor ion has a mass/charge ratio (m/z) of about 255.2. Also, in an embodiment, treatment of estradiol to form a dehydrated form of the compound reduces the complexity of the mass spectrum. Thus, in a embodiment the fragment ions comprise ions having a mass/charge ratio (m/z) of about 159.0 and 133.0. By reducing the complexity of the spectrum, the sensitivity of the procedure may be increased. The method may comprise detection of estradiol over a range of from a LOQ of about 1 pg/ml to an ULOQ of about 500 pg/mL as a single assay (i.e., as a linear assay without multiple dilution of the samples). Also, the method may comprise detection of estrone over a range of from a LOQ of about 2.5 pg/mL to and ULOQ of about 500 pg/mL as a single assay (i.e., as a linear assay without multiple dilution of the samples).

Also, since the spectrum of the estradiol is simplified, the analysis may further comprise a determination of the amount of other estrogens, such as estrone, in the sample.

The sample may only require heating for a relatively brief period of time to form the dehydrated estradiol. For example, the sample may be heated within the range of 300° C. to 1000° C. In an embodiment, the sample is heated in the interface where the sample is transferred to the mass spectrometer. In alternate embodiments, the heating step is done for less than 1 second, or less than 100 milliseconds (msec), or less than 10 msec, or less than 1 msec, or less than 0.1 msec, or less than 0.01 msec, or less than 0.001 msec.

In other embodiments, the present invention comprises methods for determining the presence or amount of a free thyroxine in a sample or a plurality of samples. In an embodiment, the present invention may comprise a method for determining the presence or amount of free thyroxine in a plurality of samples by tandem mass spectrometry, comprising: (a) dialyzing the plurality of samples to separate the free thyroxine from the protein-bound thyroxine in the samples; (b) generating a precursor ion of the thyroxine in each sample; (b) generating one or more fragment ions of the thyroxine in each sample; and (c) detecting the presence or amount of one or more of the ions generated in step (b) or (c) or both in each sample, and relating the detected ions to the presence or amount of the free thyroxine in the plurality of samples.

In an embodiment, the method may comprise detection of thyroxine over a range of from a LLOQ of about 2.0 pg/mL to an ULOQ of about 100 pg/mL as a single assay (i.e., without dilution of the samples). In an embodiment, and as described in more detail herein, the dialysing step may comprise the use of a buffer, and wherein the buffer comprises and sufficient salts such that the buffer is isotonic.

In an embodiment, the sample may be subjected to a purification step prior to ionization. For example, in certain embodiments, the purification step may comprises chromatography. As discussed herein, in certain embodiments, the chromatography comprises high performance liquid chromatography (HPLC). The LC step may comprise one LC separation, or multiple LC separations. In one embodiment, the chromatographic separation comprises extraction and analytical liquid chromatography. Additionally or alternatively, high turbulence liquid chromatography (HTLC) may be used.

The purification may comprise steps in addition to HPLC or other types of chromatographic separation techniques. In alternate embodiment, the purification may comprise at least one of liquid-liquid extraction or dilution. In alternate embodiment, the sample may diluted in a solvent or solvents used for LC or MS, rather than undergoing LLE.

In other embodiments, the present invention comprises a system for determining the presence or amount of one or more biomarkers in a sample. In an embodiment, the system for determining the presence or amount of one or more biomarkers in a sample may comprise a station for chromatographically separating the one or more biomarkers from other components in the sample. For example, in some embodiments, the present invention may comprise system for determining the presence or amount of at least one biomarker of interest in a sample, the system comprising: a station for providing a sample believed to contain at least one biomarker of interest; a station for chromatographically separating the at least one biomarker of interest from other components in the sample; and a station for analyzing the chromatographically separated at least one biomarker of interest by mass spectrometry to determine the presence or amount of the one or more biomarkers in the sample. In an embodiment, the system may comprise a station for partially purifying the at least one biomarker of interest from other components in the sample. In an embodiment, the mass spectrometry is operated in an atmospheric pressure chemical ionization (APCI) mode. In an embodiment, the system may further comprise a station for dialyzing a plurality of samples as a means to separate the at least one biomarker of interest that is bound to proteins in the sample from the portion of the biomarker of interest that is free in solution (i.e., "free"). Also in certain embodiments, at least one of the stations is automated and/or controlled by a computer. For example, as described herein, in certain embodiments, at least some of the steps are automated such that little to no manual intervention is required.

In one embodiment, the station for chromatographic separation comprises at least one apparatus to perform liquid chromatography (LC). In one embodiment, the station for liquid chromatography comprises a column for extraction chromatography. Additionally or alternatively, the station for liquid chromatography comprises a column for analytical chromatography. In certain embodiments, the column for extraction chromatography and analytical chromatography comprise a single station or single column. For example, in one embodiment, liquid chromatography is used to purify the biomarker of interest from other components in the sample that co-purify with the biomarker of interest after extraction or dilution of the sample.

The system may also include a station for analyzing the chromatographically separated one or more biomarkers of interest by mass spectrometry to determine the presence or amount of the one or more biomarkers in the test sample. In certain embodiments, tandem mass spectrometry is used (MS/MS). For example, in certain embodiments, the station for tandem mass spectrometry comprises an Applied Biosystems API4000 or API5000 or thermo quantum or Agilent 7000 triple quadrupole mass spectrometer.

The system may also comprise a station for extracting the one or more hormones or metabolites from the test sample and/or diluting the sample. In an embodiment, the station for extraction comprises a station for liquid-liquid extraction. The station for liquid-liquid extraction may comprise equipment and reagents for addition of solvents to the sample and removal of waste fractions. In some cases a isotopically-labeled internal standard is used to standardize losses of the biomarker that may occur during the procedures. Thus, the station for liquid-liquid extraction may comprise a hood or other safety features required for working with solvents.

Additionally, the system may comprise a station for dialyzing sample as a means to separate the free hormone or metabolite from a sample that comprises free and protein-bound hormone or metabolite for measurement. The station for dialysis may comprise equipment for aliquoting samples into dialysis chambers. Also, the station for dialysis may comprise a mixing chamber to effect dialysis of the free analyte (e.g., free hormone) from the sample.

In embodiments of the methods and systems of the present invention, the biomarker is a hormone or a metabolite. The methods and systems of the present invention may be used to measure the amount of either total and/or free biomarkers of intersest in serum. In an embodiment, the hormone may comprise a steroid hormone. Or, the hormone may comprise a thyroid hormone. Or, the hormone may comprise a protein or peptide hormone. For example, in alternate embodiments, the steroid hormone may comprise an estrogen, androgen, mineralcorticoid, or glucocorticoid hormone. In certain embodiments, the hormone may comprise at least one of estrone or estradiol. In other embodiments, the hormone may comprise an estrogen metabolite. For example, the hormone may comprise estrone sulfate and/or glucoronidated and sulphated metabolites of estradiol, estrone or estriol. Or, other steroid hormones or steroid hormone metabolites may be measured. For example, the hormone may comprise testosterone. Or, non-steroid hormones may be measured. For example, in certain embodiments, the methods and systems may be used to measure a thyroid hormone, such as free thyroxine (T4) or triiodothyronine (T3). Or, pre-hormones (such as 25 hdroxyvitamin D) may be measured. For examples, the methods and systems of the present invention may be used to measure vitamins or other metabolites. In some embodiments, the metabolite may comprise a vitamin D compound such as 25-hydroxyvitamin D2 or 25-hydroxyvitamin D3, 1,25 dihydroxyvitamin D2 and 1,25 dihydroxyvitamin D3. In yet other embodiments, the methods and systems of the present invention may be used to measure a non-hormone compound.

In certain embodiments, the test samples suitable for analysis by the methods and systems of the present invention can include any liquid sample that can contain one or more target analytes of interest. In an embodiment, the biomarker is endogenous to a subject. For example, in some embodiments, the test sample comprises a biological sample. As used herein, the term "biological sample" refers to a sample obtained from a biological source, including, but not limited to, an animal, a cell culture, an organ culture, and the like. Suitable samples include blood, plasma, serum, urine, saliva, tear, cerebrospinal fluid, organ, hair, muscle, or other tissue sample.

As used herein, a subject may comprise an animal. Thus, in some embodiments, the biological sample is obtained from a mammalian animal, including, but not limited to a dog, a cat, a horse, a rat, a monkey, and the like. In some embodiments, the biological sample is obtained from a human subject. In some embodiments, the subject is a patient, that is, a living person presenting themselves in a clinical setting for diagnosis, prognosis, or treatment of a disease or condition. In some embodiments, the test sample is not a biological sample, but comprises a non-biologicial sample, e.g., obtained during the manufacture or laboratory analysis of a synthetic steroid, which can be analyzed to determine the composition and/or yield of the manufacturing and/or analysis process.

A variety of methods may be used to extract the biomarker of interest from the sample. In certain embodiments, extracting the one or more hormones or metabolites from the test sample comprises a liquid-liquid extraction procedure. For example, for the analysis of estrone and estradiol in serum, a hexane:ethyl acetate is used for extraction. For example, in one embodiment, a 9:1 hexane:ethyl acetate solution may be used.

In certain embodiments, purifying the at least one biomarker of interest from the test sample may also comprise the use of a liquid chromatography extraction column. In one embodiment, the column is on-line. In an embodiment, purification of the biomarker of interest using a extraction column may comprises the steps of: (i) transferring the test sample on an extraction column; and (ii) eluting the biomarker of interest from the extraction column.

In certain embodiments, the methods and systems of the present invention may comprise multiple liquid chromatography steps. Thus, in certain embodiments, a two-dimensional liquid chromatography (LC) procedure is used. For example, in one embodiment, the method and systems of the present invention may comprise transferring the biomarker of interest from the LC extraction column to an analytical column. In one embodiment, the transferring of the at least one biomarker of interest from the extraction column to an analytical column is done by a heart-cutting technique. In another embodiment, the biomarker of interest is transferred from the extraction column to an analytical column by a chromatofocusing technique. Alternatively, the biomarker of interest is transferred from the extraction column to an analytical column by a column switching technique. These transfer steps may be done manually, or may be part of an on-line system.

Various columns comprising stationary phases and mobile phases that may be used for extraction or analytical liquid chromatography are described herein. The column used for extraction liquid chromatography may be varied depending on the biomarker of interest. In some embodiments, the extraction column is a functionalized silica or polymer-silica hybrid or polymeric particle or monlithic silica stationary phase, such as a Poroshell SBC-18 column. The column used for analytical liquid chromatography may be varied depending on the biomarker of interest and/or the column that was used for the extraction liquid chromatography step. For example, in certain embodiments, the analytical column comprises particles having an average diameter of about 5 µm. In some embodiments, the analytical column is a functionalized silica or polymer-silica hybrid, or a polymeric particle or monolithic silica stationary phase, such as a phenyl-hexyl functionalized analytical column.

A variety of methods may be used to quantify the at least one biomarker of interest once the biomarker of interest has been substantially purified (i.e., substantially separated away from other components that may have been present in the sample). In some embodiments, mass spectrometry is used to quantify the at least one biomarker of interest. In certain embodiments, the mass spectrometer may comprise a tandem mass spectrometer (MS/MS). For example, in one embodiment of the methods and systems of the present invention, the tandem MS/MS spectrometry comprises a triple quadrupole tandem mass spectrometer.

The tandem MS/MS may be operated in a variety of modes. In one embodiment, the tandem MS/MS spectrometer is operated in an atmospheric pressure chemical ionization (APCI) mode. In some embodiments, the quantification of the analytes and internal standards is performed in the selected reaction monitoring mode (SRM).

Thus, embodiments of the present invention comprise methods and systems for applying liquid chromatography and mass spectrometry as a means to separate a biomarker analyte of interest from other components that may be present in a biological sample. In certain embodiments, two liquid chromatography (LC) steps are used in tandem. Also, the method may comprise an off-line liquid-liquid extraction and/or sample dilution step as a means to partially purify the sample prior to liquid chromatography. In some embodiments, tandem mass spectrometry is used to quantify the analyte of interest. The methods and systems may be used for clinical diagnosis.

The systems and methods of the present invention may, in certain embodiments, provide for a multiplexed assay. For example, certain embodiments of the present invention may comprise a multiplexed liquid chromatography tandem mass spectrometry (LC-MS/MS) or two-dimensional or tandem liquid chromatography-tandem mass spectrometry (LC)-LC-MS/MS) methods for the quantitative analysis of one or more analytes, including steroid hormones, such as estrone and estradiol and/or thyroid hormones, such as free thyroxine (T4) or triiodothyroine (T3) in biological samples.

An example of a method (2) of the present invention is shown in FIG. 1. Thus, in an embodiment, the method may include a step of providing a biological sample, for example, a serum sample believed to contain one or more analytes of interest (4). In some embodiments, an appropriate internal standard is added to the sample (6). For example, in some embodiments of the presently disclosed method for analyzing estrone and estradiol in serum samples, deuterated $D_4$-estrone and $D_5$-estradiol are added as internal standards. Or, $C_{13}$-estrone and $C_{13}$-estradiol stable labeled isotopes may be used. Or, for thyroxine, a deuterated or $C_{13}$ derviative may be used. For example, in one embodiment, Thyroxine Ring-$^{13}C_6$ may be used. In yet other embodiments, structural analogus of the biomarker of interest may be used. For example, such structural analogues may comprise compounds wherein a first chemical group is replaced with a second chemical group. In general, the groups are of similar chemical reactivity, but different mass, as for example, the replacement of a methyl (—CH$_3$) group with an ethyl (—CH$_2$CH$_3$) group.

In some embodiments, the analytes of interests are partially purified by liquid-liquid extraction of the sample (8). Or, the sample may be diluted (9) in a solvent that can be used for LC or MS in subsequent purification steps.

In an embodiment, the liquid-liquid extraction is used to concentrate and partially purify the analyte. For example, for estradiol/estrone analysis, the liquid extraction may be used to remove conjugated estrogens, such as sulfated and glucoronidated estrogens. Also, the liquid extraction may remove lipids and/or fibrinogen from the samples. In some embodiments, estrone and estradiol can be extracted from a serum sample with an organic solvent that can separate estrone and estradiol from conjugated estrogens. For example, in an embodiment, an alkane mixed with a more polar solvent is used. For example, in certain embodiments, hexane is mixed with a more polar solvent. In an embodiment, the polar solvent comprises ethyl acetate or a similar solvent. In an embodiment, 9:1 hexane:ethyl acetate is used.

Or, other solvents may be used. As is known in the art, the solvents employed may be optimized to separate the analyte of interest from the sample. For example, the solvents used to extract estrone and estradiol from serum may not be the same solvent or solvent mix as used to extract estrone and estradiol from urine. Or, the solvents used to extract estrone and estradiol from serum may not be the same solvent or solvent mix as used to extract thyroxine (T4), triiodothyronine (T3), or vitamin-D compounds from serum. For example, in certain embodiments, acetonitrile is used for liquid extraction of vitamin-D compounds, and ethyl acetate:hexane:methanol is used for extraction of T4.

Certain biomolecules may have a propensity to nonspecifically bind to proteins or other biomolecules. For example, thyroid hormones can non-specifically bind to proteins such as serum albumin, sex hormone binding globulin, and the like. For determination of free thyroxine (T4), the sample may be treated to separate the free thyroxine from thyroxine that is bound to proteins in the biological sample (e.g., serum).

In one embodiment, the sample may initially be dialyzed to separate the free hormone or metabolite from a mixture of free and protein-bound hormone or metabolite (5). In certain embodiments, multiple samples may be processed concerrently. For example, the dialysis may be performed using a multiwell dialysis plate which allows for the dialysis of multiple samples at one time. In certain embodiments 96 well plates are used. In this way, multiple samples are processed to comprise a high throughput assay.

For example, samples of serum that may contain free thyroxine and protein-bound thyroxine may be introduced into the individual sample chambers which are on one side of the membrane and a buffer solution introduced into the diluent chambers on the other side of the membrane from the sample. The 96 well plate is then positioned vertically and rotated to facilitate transfer of the free thyroxine across the membrane.

The dialysis buffer may, in certain embodiments, be isotonic and contain gelatin. The gelatin may be used over a range of concentrations depending upon the nature of the membranes and hardware used for dialysis. In alternate embodiments, the gelatin may be in a range of from about 0.1 to 10 mg/mL. In an embodiment, the gelatin is at about 1 mg/mL. In certain embodiments, the buffer used for dialysis comprises multiple endogenous salts to provide a buffer that is isotonic with the serum sample to thereby negate any potential dilution effects and/or disruptions to the ratio of bound thyroxine to free thyroxine in the sample. Also, gelatin may be include to prevent adsorptive losses of free thyroixine onto the dialysis membrane or the sample chamber. Gelatin may act as a carrier on the dialysate side of the 96-well plate to ensure free thyroxine remains in the dialysate solution. Gelatin does not bind free thyroxine and thus, does not affect the ratio of bound throxine to free thyroxine in the sample on the sample side of the membrane.

For the analysis of free thyroxine, a liquid extraction step may be performed after the dialysis. The liquid extraction may be designed to remove residual salts and/or other additives which are used in the dialysis solution and/or remain from the sample, but that may interfere with the MS analysis. Thus, in one embodiment, the dialysate comprising free thyroxine is extracted with 71.25:23.75:5 ethyl acetate:hexane: methanol. In another embodiment, the dialysate may be diluted with a solution of methanol containing a stable labeled internal standard and directly injected onto the LC-MS/MS system for analysis.

Where the sample is extracted, the internal standard addition may include a protein to prevent the free thyroxin from sticking to the walls of the sample container. Addition of protein (e.g., bovine serum albumin) can minimize losses in extraction and recovery for liquid-liquid extraction. Where extraction is not performed, the internal standard may be added in methanol or a similar solvent used for LC.

As is known in the art, in some embodiments, the organic extract may be transferred to a fresh tube and then backwashed. For example, in an embodiment where the analyte of interest is estradiol and/or estrone, the solvent may be backwashed with aqueous sodium hydroxide (pH of about 12) to further purify the sample. Or, for extraction of other biomarkers, back-extraction may employ other solvents. The backwash may, in certain embodiments, remove additional lipids or interfering analytes from the sample.

The extract supernatant may then be evaporated and the sample reconstituted. For example, for analysis of estradiol and/or estrone, the sample may be reconstituted in 70:30 water:methanol. Or, for analysis of thyroxine, the solvent used for liquid-liquid extraction may be evaporated and the sample reconstituted in 50:50 water:methanol.

Still referring to FIG. 1, the method may further include liquid chromatography as a means to separate the analyte of interest from other components in the sample. In an embodiment, two liquid chromatography steps are used. For example, the method may comprise a first extraction column liquid chromatography (10), transfer of the biomarker of interest to a second analytical column (12), and an analytical column liquid chromatography (16). In other embodiments, only one liquid chromatography step is used.

The first extraction liquid chromatography column may, in certain embodiments, comprise a step whereby the analytes of interest are separated from a majority of contaminants. Thus, in certain embodiments, the first column provides the majority of selectivity for the procedure. The second analytical liquid chromatography column may, in certain embodiments, comprise a step whereby the analytes of interest are concentrated, to thereby increase sensitivity for analysis by mass spectrometry (MS).

For example, the reconstituted extract may be applied onto a high performance liquid chromatography (HPLC) system, wherein the analytes are eluted using an isocratic separation through an extraction column. In certain embodiments, the mobile phase that is used comprises a gradient. For example, in an embodiment for the separation of estradiol and estrone from other components in serum, the stationary phase comprises a Poroshell 300SBC-18 column. Thus, the inventors have found that surprisingly, a stationary phase designed for large molecules such as proteins may be used to separate smaller molecules such as estrone and estradiol. The mobile phase may comprise methanol and water.

Depending upon the biomarker of interest, a variety of analytical columns known in the art may be used as needed to provide good purification. In certain embodiments, the analytical column may comprise particles having an average diameter of about 5 μm. In some embodiments, the analytical column is a functionalized silica or polymer-silica hybrid, or a polymeric particle or monolithic silica stationary phase, such as a phenyl-hexyl functionalized analytical column.

For example, in one embodiment, estrone and estradiol are separated from isobaric substances by separation using a Poroshell 300SBC10 column (7.5 mm by 2.1 mm) with 5 micron particle size using a gradient separation using methanol and water for elution at 1 mL per minute flow rate. Estrone and estradiol are transferred from the extraction column after 2.5 minutes and chromatofocused onto a phenyl-hexyl column (50 mm by 2.1 mm) with 5 micron particles using water for 45 seconds. The transferred and purified analytes are chromatographed using an accelerated gradient employing methanol and water to improve sensitivity prior to introduction into the mass spectrometer interface and subsequent detection.

For liquid chromatography of thyroxin, a single liquid chromatography step may be used. Thus, for liquid chromatography of thyroxin, a phenyl hexyl column (50 mm by 2.1 mm) with 5 micron particle size may be used. Thus, following either: (a) liquid-liquid extraction, evaporation and reconstitution; or (b) post-dialysis sample dilution with internal standard solution; samples are injected onto the liquid chromatography column. The transferred analyte and internal standard are chromatographed using a methanol:water gradient separation at 1 mL per minute. To enable further sensitivity gains, a post-separation additional flow of 90:10 methanol:water containing ammonium carbonate (1 mM) is introduced at 200 microliters per minute prior to introduction into the mass spectrometer (MS) electrospray interface.

If two liquid chromatography steps are employed, the eluted analytes may be transferred to the analytical column in a manner such that the sample is concentrated upon application to the analytical column. In some embodiments, the eluted analytes are transferred to the analytical column via a heart-cutting technique. In some embodiments, a chromatofocusing procedure is used to transfer and focus the analytes on the analytical column. Also in some embodiments, a column-switching procedure is used to transfer the analytes to the analytical column. The analytes may then be separated on the analytical column (16) and the fraction containing the analyte of interest is eluted. In an embodiment, the second column in run in a manner to maximize throughput, and to provide the sample in a reduced volume.

The separated analytes are then introduced into a mass spectrometer (MS) system (20). In some embodiments, a tandem MS/MS system is used. As is known by those of skill in the art, in tandem MS spectrometry, the precursor ion is selected following ionization, and that precursor ion is subjected to fragmentation to generate product (i.e., fragment) ions, whereby one or more product ions are selected for detection. A sample may therefore be analyzed for both estradiol and estrone since the compounds have different precursor and product ions in tandem mass spectrometric methodologies (i.e., different transitions).

The analyte of interest may then be quantified based upon the amount of the characteristic transitions measured by tandem MS. In some embodiments, the tandem mass spectrometer comprises a triple quadrupole mass spectrometer. In some embodiments, the tandem mass spectrometer is operated in a positive ion Atmospheric Pressure Chemical Ionization (APCI) mode. In some embodiments, the quantification of the analytes and internal standards is performed in the selected reaction monitoring mode (SRM). Or, other methods of ionization such as the use of inductively coupled plasma, or MALDI, or SELDI, ESI, or APPI may be used for ionization.

In some embodiments, the back-calculated amount of each analyte in each sample may determined by comparison of unknown sample response or response ratio when employing internal standardization to calibration curves generated by spiking a known amount of purified analyte material into a standard test sample, e.g., charcoal stripped human serum. In one embodiment, calibrators are prepared at known concentrations and analyzed as per the biomarker methodology to generate a response or response ratio when employing internal standardization versus concentration calibration curve.

In one embodiment, the sample may be treated so as to chemically modify the analyte of interest to allow for improved detection in the MS system. For example, in one embodiment, a sample being analyzed for estrone and/or estradiol may be heated to the extent that the estradiol loses a molecule of water thereby converting the estradiol to a dehydrated form of the compound (FIG. 2, Panels A and B, respectively). This conversion can reduce the number of major product ion peaks seen for estradiol from about 60 to 3 (FIG. 2, panels C and D). For MS analysis, the sensitivity of the analysis is generally inversely proportional to the number of product ion peaks. Thus, with fewer peaks, the sensitivity of detection using tandem mass spectrometry is increased. For example, as illustrated in FIG. 2, estradiol may be quantified by measuring the transition from the precursor ion at a mass to charge (m/z) 255.3±0.5 mass units to the two product (fragment) ions at a mass to charge (m/z) of 159.0±0.5 mass units and 133.0±0.5.

In alternate embodiments, the sensitivity obtained for measurement of estradiol is increased more than 10 fold, or more than 20 fold, or more than 50 fold, or more than 100 fold, or more than 150 fold, or more than 200 fold, or more than 500 fold, or more than 1,000 fold. For example, in alternate embodiments, the sensitivity is increased by about 5-1,000 fold, or a by about 20-500 fold, or by about 50-150 fold, or by about 100 fold.

The temperature for heating the sample may, in alternate embodiments range from 300° C. to about 1000° C. and includes all ranges therein. In an embodiment, the dehydration step is performed within the interface of the mass spectrometer employed in APCI or electrospray mode at 500 degrees C.±100 degrees. In an embodiment, the sample is heated for several microseconds at the interface for dehydration to occur. In alternate embodiments, the heating step is done for less than 1 second, or less than 100 milliseconds (msec), or less than 10 msec, or less than 1 msec, or less than 0.1 msec, or less than 0.01 msec, or less than 0.001 msec.

In an embodiment, the tandem liquid chromatograhy (LC) steps help reduce isobaric interferences. For example, in one embodiment, there are 24 potential isobaric interferences in estradiol (transition m/z 255->159, 133), and 16 potential interferences for estrone (transition m/z 273->159, 133). For example, dehydroepiandrosterone (DHEA) undergoes thermal dehydration forming MH-H20]+ and MH-2H$_2$O]+(FIG. 3). There may be DHEA concentrations that are about 300-1,500 times the levels of estrone and estradiol in healthy patients. Thus, the M+2 isotopic overlap of dehydrated DHEA may become an isobaric interference. Heart cutting from the primary separation using isocratic or gradient separation resolves most isobaric interferences (FIG. 4). Thus, as shown in FIG. 4, heart cutting combined with chromatofocusing may be used to separate estradiol (E2) and estrone (E1) from all but one potential isobaric contaminant which is separated within the analytical (second) liquid chromatography separation dimension.

An example of a method for measuring estradiol and estrone is provided in FIG. 5. For example, in an embodiment, a method (40) of measuring estrone and estradiol comprise providing a sample believed to contain at least one of estrone and estradiol (44). The method may also comprise adding an internal standard of $D_4$-estrone and $D_5$-estradiol to the sample (46).

Also, the method may optionally comprise partial purification of the estrone and estradiol by liquid-liquid extraction of the estrone and/or estradiol from the serum with 9:1 hexane-ethyl acetate (48). Or, the sample may be diluted (50) as a means to improve sensitivity in subsequent purification and/or analysis steps (e.g. LC and/or MS).

After initial purification by liquid-liquid extraction or dilution, the sample may be further purified by liquid chromatography. Thus, in one embodiment, the solvent is evaporated and the extracted estrone/estradiol is reconstituted in 30:70 methanol water for application to a liquid chromatography extraction column (52). The estradiol/estrone may be eluted from the extraction column. For example, in alternate embodiments, the estradiol/estrone may be eluted by heart cutting, chromatofocusing or column switching. Next, the fraction containing the estrone/estradiol may, in certain embodiments, be applied to an analytical LC column (54). The fraction containing the estrone/estradiol may then be transferred to the LC-MS/MS interface to undergo ionization and dehydration of the estradiol (60) prior to MS/MS detection in SRM mode (62). In an embodiment, heating the estradiol removes a molecule of water, and changes the resultant MS/MS profile such that it comprises only three major product ions.

Thus, the methods provide the ability to quantify estrone and/or estradiol at physiologically relevant levels. As discussed herein, the difference between a serum level of 10 pg/mL and 15 pg/mL may be clinically relevant. In one embodiment, the method is able to measure estrone and/or estradiol at levels of about 2.5 pg/mL and 1 pg/mL respectively.

An example of a method for measuring free thyroxine (T4) (70) is provided in FIG. 6. In an embodiment, the method may comprise providing a sample that includes thyroxine (both free and protein-bound) (74). The method may also comprise dialyzing the sample (76) to separate the free thyroxine from the protein bound thyroxine. Also, the method may comprise adding an internal standard such as $^6C_{13}$-thyroxine (78) to allow for the measured amount of thyroxine to be correlated to the actual amount present in the sample (i.e., to quantify the amount lost during the extraction and measurement procedures).

The method may also comprise an optional step whereby the free thyroxine present in the dialysate is extracted by liquid-liquid extraction (80). Alternatively, the sample may be diluted into the solvent used for LC-MS/MS as a means to reduce interference from non-T4 or non-T3 analytes (81). At this point, the solvent used for extraction may be evaporated, and the extracted thyroxine reconstituted in 50:50 methanol: water for application to an LC column (82). The free thyroxine may then be eluted from the column (84) and then quantified by MS/MS (86).

Thus, the methods provide the ability to quantify free thyroxine at physiologically relevant levels. The difference between a serum level of 8 pg/mL and 12 pg/mL T4 may be clinically relevant. The method is able to measure free thyroxine (T4) at levels of 2 pg/mL.

Systems for Quantification of Endogenous Biomarkers

Figure 7A:
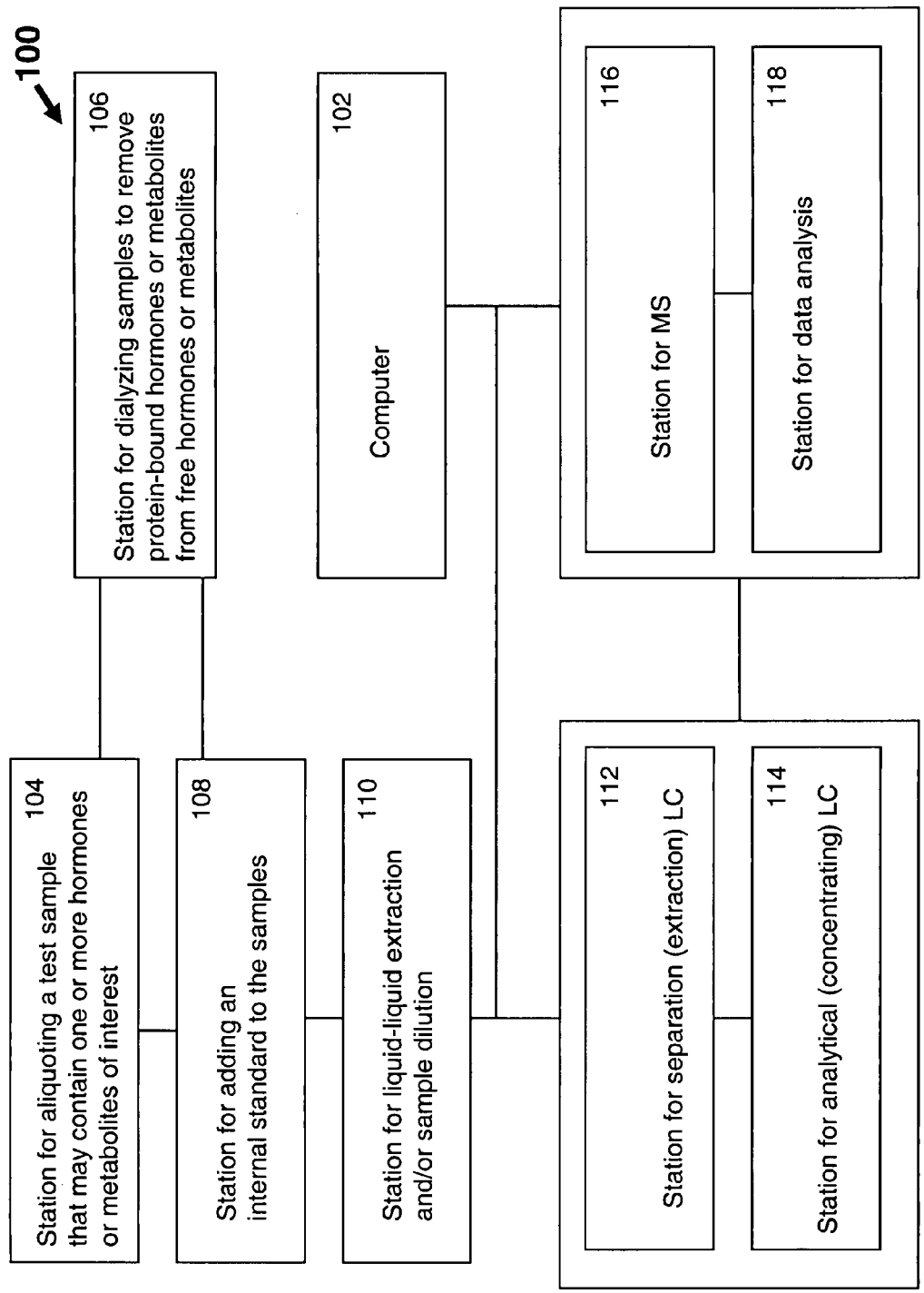

FIG. 7A shows an embodiment of a system of the present invention. As shown in FIG. 7, the system may comprise a station for aliquoting a sample (104) that may comprise a biomarker of interest into sampling containers. In one embodiment, the sample is aliquoted into a container or containers to facilitate liquid-liquid extraction or sample dilution. The station for aliquoting may comprise receptacles to discard the portion of the biological sample that is not used in the analysis.

Alternatively or additionally, the sample may be aliquoted into a container for dialysis. As described above, the container for dialysis may comprise a multi-well plate. Thus, in addition to the station for aliquoting, the system may comprise a station for dialysis (106). The station for dialysis may comprise a rotator oven, multi-chamber pipettes for sample transfer, as well as receptacles to discard the portion of the biological sample that is not used in the analysis.

The system may further comprise a station for adding an internal standard to the sample (108). In an embodiment, the internal standard comprises the biomarker of interest labeled with a non-natural isotope. Thus, the station for adding an internal standard may comprise safety features to facilitate adding an isotopically labeled internal standard solutions to the sample. The system may also, in some embodiments, comprise a station (110) for liquid-liquid extraction and/or dilution of the sample.

The system may also comprise a station for liquid chromatography (LC) of the sample. As described herein, in an embodiment, the station for liquid chromatography may comprise an extraction liquid chromatography column (112). The station for liquid chromatography may comprise a column comprising the stationary phase, as well as containers or receptacles comprising solvents that are used as the mobile phase. In an embodiment, the mobile phase comprises a gradient of methanol and water, acetonitrile and water, or other miscible solvents with aqueous volatile buffer solutions. Thus, in one embodiment, the station may comprise the appropriate lines and valves to adjust the amounts of individual solvents being applied to the column or columns. Also, the station may comprise a means to remove and discard those fractions from the LC that do not comprise the biomarker of interest. In an embodiment, the fractions that do not contain the biomarker of interest are continuously removed from the column and sent to a waste receptacle for decontamination and to be discarded.

A variety of extraction LC systems may be used. For example, in the embodiment where the system is being used to measure estrone or estradiol, a Poroshell 300SBC18 extraction column with a phenyl hexyl analytical column, with mobile phases comprising a gradient of methanol and water are used. Or, for measurement of thyroxine, a phenyl hexyl column, with a mobile phase of methanol:water is used with post-column addition of a methanol:water solution containing ammonium carbonate. Or, for vitamin D metabolites, a Fluophase WP extraction column, with a mobile phase of methanol:water is used and an Extent C18 analytical column is used with a mobile phase of methanol:water is used.

The system may also comprise an analytical LC column (114). The analytical column may facilitate further purification and concentration of the biomarker of interest as may be required for further characterization and quantification.

Also, the system may comprise a station for characterization and quantification of the biomarker of interest. In one embodiment, the system may comprise a station for mass spectrometry (MS) of the biomarker. In an embodiment, the station for mass spectrometry comprises a station for tandem mass spectrometry (MS/MS). Also, the station for characterization and quantification may comprise a computer and software for analysis of the MS/MS results. In an embodiment, the analysis comprises both identification and quantification of the biomarker of interest.

In some embodiments, one or more of the purification or separation steps can be preformed "on-line." As used herein, the term "on-line" refers to purification or separation steps that are performed in such a way that the test sample is disposed, e.g., injected, into a system in which the various components of the system are operationally connected and, in some embodiments, in fluid communication with one another. The on-line system may comprise an autosampler for removing aliquots of the sample from one container and transferring such aliquots into another container. For example, an autosampler may be used to transfer the sample after extraction onto an LC extraction column. Additionally or alternatively, the on-line system may comprise one or more injection ports for injecting the fractions isolated from the LC extraction columns onto the LC analytical column. Additionally or alternatively, the on-line system may comprise one or more injection ports for injecting the LC purified sample into the MS system. Thus, the on-line system may comprise one or more columns, including but not limited to, an extraction column, including an HTLC extraction column, and in some embodiments, an analytical column. Additionally or alternatively, the system may comprise a detection system, e.g., a mass spectrometer system. The on-line system may also comprise one or more pumps; one or more valves; and necessary plumbing. In such "on-line" systems, the test sample and/or analytes of interest can be passed from one component of the system to another without exiting the system, e.g., without having to be collected and then disposed into another component of the system.

In some embodiments, the on-line purification or separation method can be automated. In such embodiments, the steps can be performed without the need for operator intervention once the process is set-up and initiated. For example, in one embodiment, the system, or portions of the system may be controlled by a computer or computers (102). Thus, in certain embodiments, the present invention may comprise software for controlling the various components of the system, including pumps, valves, autosamplers, and the like. Such software can be used to optimize the extraction process through the precise timing of sample and solute additions and flow rate.

Although some or all of the steps in the method and the stations comprising the system may be on-line, in certain embodiments, some or all of the steps may be performed "off-line." In contrast to the term "on-line", the term "off-line" refers to a purification, separation, or extraction procedure that is performed separately from previous and/or subsequent purification or separation steps and/or analysis steps. In such off-line procedures, the analytes of interests typically are separated, for example, on an extraction column or by liquid/liquid extraction, from the other components in the sample matrix and then collected for subsequent introduction into another chromatographic or detector system. Off-line procedures typically require manual intervention on the part of the operator.

Liquid chromatography may, in certain embodiments, comprise high turbulence liquid chromatography or high throughput liquid chromatography (HTLC). See, e.g., Zimmer et al., J. Chromatogr. A 854:23-35 (1999); see also, U.S. Pat. Nos. 5,968,367; 5,919,368; 5,795,469; and 5,772,874. Traditional HPLC analysis relies on column packings in which laminar flow of the sample through the column is the basis for separation of the analyte of interest from the sample. In such columns, separation is a diffusional process. Turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the biomarker of interest prior to mass spectrometry. In such embodiments, samples may be extracted using an HTLC extraction cartridge which captures the analyte, then eluted and chromatographed on a second HTLC column or onto an analytical HPLC column prior to ionization. Because the steps involved in these chromatography procedures can be linked in an automated fashion, the requirement for operator involvement during the purification of the analyte can be minimized. Also, in some embodiments, the use of a high turbulence liquid chromatography sample preparation method can eliminate the need for other sample preparation methods including liquid-liquid extraction. Thus, in some embodiments, the test sample, e.g., a biological fluid, can be disposed, e.g., injected, directly onto a high turbulence liquid chromatography system.

For example, in a typical high turbulence or turbulent liquid chromatography system, the sample may be injected directly onto a narrow (e.g., 0.5 mm to 2 mm internal diameter by 20 to 50 mm long) column packed with large (e.g., >25 micron) particles. When a flow rate (e.g., 3-500 mL per minute) is applied to the column, the relatively narrow width of the column causes an increase in the velocity of the mobile phase. The large particles present in the column can prevent the increased velocity from causing back pressure and promote the formation of vacillating eddies between the particles, thereby creating turbulence within the column.

In high turbulence liquid chromatography, the analyte molecules may bind quickly to the particles and typically do not spread out, or diffuse, along the length of the column. This lessened longitudinal diffusion typically provides better, and more rapid, separation of the analytes of interest from the sample matrix. Further, the turbulence within the column reduces the friction on molecules that typically occurs as they travel past the particles. For example, in traditional HPLC, the molecules traveling closest to the particle move along the column more slowly than those flowing through the center of the path between the particles. This difference in flow rate causes the analyte molecules to spread out along the length of the column. When turbulence is introduced into a column, the friction on the molecules from the particle is negligible, reducing longitudinal diffusion.

The methods and systems of the present invention may use mass spectrometry to detect and quantify the biomarker of interest. The terms "mass spectrometry" or "MS" as used herein generally refer to methods of filtering, detecting, and measuring ions based on their mass-to-charge ratio, or "m/z." In MS techniques, one or more molecules of interest are ionized, and the ions are subsequently introduced into a mass spectrometer where, due to a combination of electric fields, the ions follow a path in space that is dependent upon mass ("m") and charge ("z").

In certain embodiments, the mass spectrometer uses a "quadrupole" system. In a "quadrupole" or "quadrupole ion trap" mass spectrometer, ions in an oscillating radio frequency (RF) field experience a force proportional to the direct current (DC) potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

In certain embodiments, tandem mass spectrometry is used. See, e.g., U.S. Pat. No. 6,107,623, entitled "Methods and Apparatus for Tandem Mass Spectrometry," which is hereby incorporated by reference in its entirety. Further, the selectivity of the MS technique can be enhanced by using "tandem mass spectrometry," or "MS/MS." Tandem mass spectrometry (MS/MS) is the name given to a group of mass spectrometric methods wherein "parent or precursor" ions generated from a sample are fragmented to yield one or more "fragment or product" ions, which are subsequently mass analyzed by a second MS procedure. MS/MS methods are useful for the analysis of complex mixtures, especially biological samples, in part because the selectivity of MS/MS can minimize the need for extensive sample clean-up prior to analysis. In an example of an MS/MS method, precursor ions are generated from a sample and passed through a first mass filter to select those ions having a particular mass-to-charge ratio. These ions are then fragmented, typically by collisions with neutral gas molecules in a suitable ion containment device, to yield product (fragment) ions, the mass spectrum of which is recorded by a electron multiplier detector. The product ion spectra so produced are indicative of the structure of the precursor ion, and the two stages of mass filtering can eliminate ions from interfering species present in the conventional mass spectrum of a complex mixture.

In an embodiment, the methods and systems of the present invention use a triple quadrupole MS/MS (see e.g., Yost, Enke in Ch. 8 of Tandem Mass Spectrometry, Ed. McLafferty, pub. John Wiley and Sons, 1983). Triple quadrupole MS/MS instruments typically consist of two quadrupole mass filters separated by a fragmentation means. In one embodiment, the instrument may comprise a quadrupole mass filter operated in the RF only mode as an ion containment or transmission device. In an embodiment, the quadropole may further comprise a collision gas at a pressure of between 1 and 10 millitorr. Many other types of "hybrid" tandem mass spectrometers are also known, and can be used in the methods and systems of the present invention including various combinations of magnetic sector analyzers and quadrupole filters. These hybrid instruments often comprise high resolution magnetic sector analyzers (i.e., analyzers comprising both magnetic and electrostatic sectors arranged in a double-focusing combination) as either or both of the mass filters. Use of high resolution mass filters may be highly effective in reducing chemical noise to very low levels.

For the methods and systems of the present invention, ions can be produced using a variety of methods including, but not limited to, electron ionization, chemical ionization, fast atom bombardment, field desorption, and matrix-assisted laser desorption ionization ("MALDI"), surface enhanced laser desorption ionization ("SELDI"), photon ionization, electrospray ionization, and inductively coupled plasma.

In those embodiments, such as MS/MS, where precursor ions are isolated for further fragmentation, collision-induced dissociation ("CID") may be used to generate the fragment ions for further detection. In CID, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

Figure 7B:
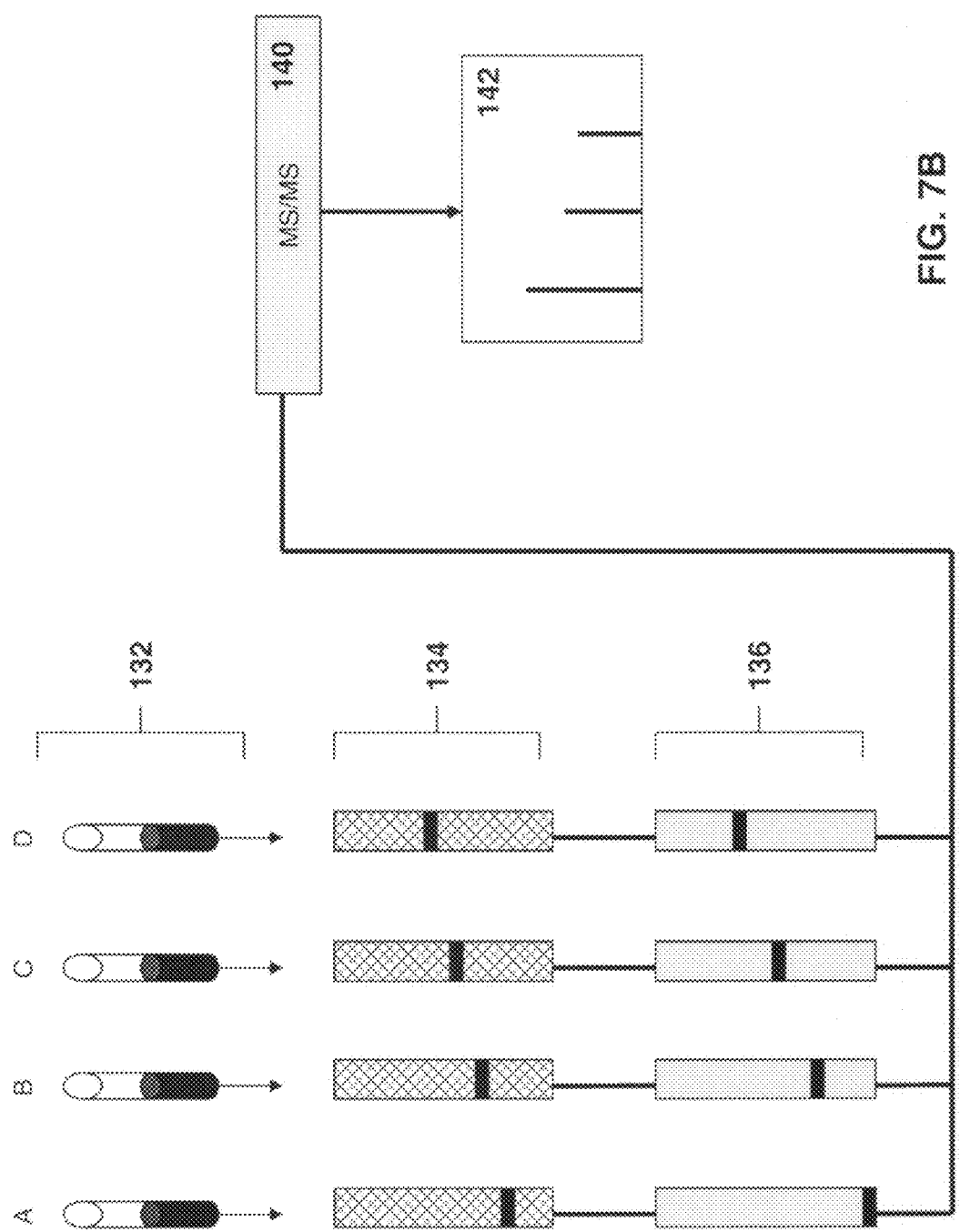

In some embodiments, to attain the required analytical selectivity and sensitivity, the presently disclosed 2D-LC-MS/MS methods include multiplexed sample preparation procedures. For example, in certain embodiments dialysis of the sample is performed using a 96 well plate having a dialysis membrane in each well or multiple sample tubes (FIG. 7B). Additionally or alternatively, the multiplex system may comprise staggered multiplexed LC and MS sample inlet systems. Also, the methods and systems of the present invention may comprise multiple column switching protocols, and/or heart-cutting (LC-LC or 2D-LC) techniques, and/or LC separations prior to MS detection. In some embodiments, the methods and systems of the present invention may include a multiplexed two-dimensional liquid chromatographic system coupled with a tandem mass spectrometer (MS/MS) system, for example a triple quadrupole MS/MS system. Such embodiments provide for staggered, parallel sample input into the MS system.

Thus, as shown in FIG. 7B, four samples (132 A-D) may each be applied to individual extraction columns (134 A-D). Once the samples have each run through the extraction column, they may each be transferred directly (e.g., by column switching) to a second set of analytical columns (136 A-D). As each sample elutes from the analytical column, it may be transferred (138) to the mass spectrometer (140) for identification and quantification.

A plurality of analytes can be analyzed simultaneously or sequentially by the presently disclosed LC-MS/MS and 2D-LC-MS/MS methods. Exemplary analytes amenable to analysis by the presently disclosed methods include, but are not limited to, steroid hormones, such as estradiol, estrone, and metabolites, such as estrone sulfate. In other embodiments, thyroid hormones, such as free thyroxine (T4) and triiodothyronine (T3) can be measured. In the other embodiments, metabolites, such as 25-Hydroxyvitamin D2, 25-Hydroxyvitamin D3, may be measured. One of ordinary skill in the art would recognize after a review of the presently disclosed subject matter that other similar analytes could be analyzed by the methods and systems disclosed herein. Thus, in alternate embodiments, the methods and systems may be used to quantify steroid hormones, protein and peptide hormones, peptide and protein biomarkers, drugs of abuse and therapeutic drugs. For example, optimization of key parameters for each analyte can be performed using a modular method development strategy to provide highly tuned bioanalytical assays. Thus, certain steps may be varied depending upon the analyte being measured as disclosed herein.

Also, embodiments of the methods and systems of the present invention may provide greater sensitivity than the sensitivities previously attainable for many of the analytes being measured. For example, through using this optimization procedure, an LOQ of about 1 picogram per milliliter (pg/mL), or less than 5 pg/mL, or less that 10 pg/mL, or less than 25 pg/mL is attained for the analysis of at least one of estradiol, estrone or free thyroxine without the cumbersome derivatization processes historically required for LC-MS/MS analyses of steroids. Importantly, the low levels of detection allow for the analysis of small sample volumes, for example 100 μL, 200 μL, 500 μL, or less than 1 mL, which can be necessary to analyze pediatric sample volumes. Thus, the presently disclosed LC-MS/MS and (LC)-LC-MS/MS methods can be used to measure levels of steroid hormones, such as estrone and estradiol, or other hormones or metabolites (e.g., free thyroxine, vitamin D metabolites and the like) in serum or plasma samples from children, women, and men.

Embodiments of the present invention may provide certain advantages. In certain embodiments, the methods and systems of the present invention may provide greater sensitivity than the sensitivities previously attainable for many of the analytes being measured.

Also, embodiments of the methods and systems of the present invention may provide for rapid throughput that has previously not been attainable for many of the analytes being measured. For example, using the methods and systems of the present invention, multiple samples may be analysed for free thyroxine using 96 well plates and a multiplex system of four LC-MS/MS systems, significantly increasing the throughput.

As another advantage, the specificity and sensitivity provided by the methods and systems of the present invention may allow for the analysis of analytes from a variety of biological materials. For example, the 2D-LC-MS/MS methods of the present invention can be applied to the quantification of analytes of interest in complex sample biological matrices, including, but not limited to, blood, serum, plasma, urine, saliva, and the like. Thus, the methods and systems of the present invention are suitable for clinical applications and/or clinical trials.

As additional potential advantages, in certain embodiments, the systems and methods of the present invention provide approaches for addressing isobaric interferences, varied sample content, including hemolysed and lipemic samples, while attaining low pg/mL limits of quantification (LOQ) of the target analytes. Accordingly, embodiments of the methods and systems of the present invention may provide for the quantitative, sensitive, and specific detection of clinical biomarkers used in the clinical diagnosis of endocrine disorders.

Validation of LC-MS/MS and 2D-LC-MS/MS Assays for Endogenous Biomarkers

A general strategy for the validation of the presently disclosed LC-MS/MS and 2D-LC-MS/MS methods for endogenous biomarkers is provided in Scheme 1. Thus, Scheme 1 shows the different tests that were used to validate the procedures. Matrix specificity testing was performed by analyzing 6 different lots of charcoal stripped matrix in quadruplicate for the presence of residual analyte, absence of analyte enables the charcoal stripped matrix to be spiked with known concentrations of target analytes to generate calibration curves. Internal standard specificity was performed by spiking the stable labeled internal standard into analyte-free charcoal stripped matrix and measuring for the presence of analyte in quadruplicate. Absence of unlabeled analyte confirms the purity of internal standard materials. Endogenous (hormones) and exogenous (drugs) are spiked into analyte free matrix to confirm the selectivity of the method.

Accuracy and precision was determined using 6 replicates per level in spiked charcoal stripped serum at the LLOQ, 2 levels within the analytical range and the ULOQ in 3 different batches. Precision was determined using 6 replicates in 3 separate runs of pooled matrix samples at concentrations of approximately 3 to 10 times the LLOQ, the mid point of the analytical range and approximately 80% of the ULOQ. Accuracy was determined in pooled matrix samples using spike and recovery (standard addition) at 3 different concentrations throughout the analytical range using 4 replicates per level.

Linearity was confirmed using multi-level calibrators over 5 separate runs. Sample mixing experiments were also undertaken mixing pooled matrix samples with fortified stripped matrix samples to ensure the assays were free of matrix interferences in quadruplicate. Recovery was undertaken using both spiked stripped matrix and pooled matrix samples in quadruplicate as confirmation of linearity and also further proof that the assay was free of matrix effects. The effect of matrix content on measurement was also tested following post-column infusion, addition of lipemia and hemolysis content, alternate sample types (e.g. serum and or plasma) and sample draw-tubes in quadruplicate. Sample stability was undertaken using both spiked stripped matrix samples and pooled matrix samples at storage conditions expected from sample collection to final analysis. Each condition was compared against baseline samples drawn and frozen at −70° C. for comparison and analyzed in quadruplicate at each concentration.

Inter-assay comparison was performed using at least 50 samples representing physiological range during comparison of LC-MS/MS and LC-MS/MS assays with alternate techniques. Reference range generation and/or transference was undertaken using guidance from the National Committee on Clinical Laboratory Standards (NCCLS).

| Scheme 1. Bioanalytical Validation Strategy | |
|---|---|
| Specificity Testing: | Matrix, Internal Standard, Endogenous/Exogenous Analytes |
| Accuracy and Precision: | Stripped Matrix: LLOQ, Mid levels (x2) ULOQ; Pooled Matrix: 3x LLOQ, mid and 80% of ULOQ; Spike and Recovery at 3 levels |
| Linearity: | Stripped Matrix: 7-10 point duplicate curves, 5 batches; Pooled Matrix: Sample dilution (mixing) at 4 levels |
| Recovery: | Stripped and Pooled Matrix: Spike and recovery at 3 levels |
| Ionization Effect: | Stripped and Pooled Matrix: Post-column infusion, post-extraction spiking, Heparin and EDTA anticoagulants, Lipemic and Hemolysis additives |
| Sample Stability: | Stripped and Pooled Matrix: Pre and Post processing stability compared against −70° C. baseline samples, Whole blood stability and stock solutions |
| Inter-Assay Comparison: | Pooled Matrix samples: At least 50 samples spanning normal and abnormal range |
| Reference Range: | Transference based upon 90% CI for at least 20 samples per range |

Representative LC-MS/MS and 2D-LC-MS/MS chromatograms of selected analytes at the limit of quantification (LOQ) obtained by using the LC-MS/MS and 2D-LC-MS/MS methods of the present invention are shown in FIGS. 8-13. In these figures the X axis is time, and the Y axis corresponds to the amount of material (i.e., the response). Thus, it can be seen that estrone sulfate was detected at 100 pg/mL (FIG. 8); free thyroxine was detected at 2 pg/mL (FIG. 9); 25-hydroxyvitamin D2 was detected at 1 ng/mL (FIG. 10); 25-hydroxyvitamin D3 was detected at 1 ng/mL (FIG. 11); estrone was detected at 2.5 pg/mL (FIG. 12); and estradiol was detected at 1 pg/mL (FIG. 13).

Similarly, representative LC-MS/MS and 2D-LC-MS/MS chromatograms of selected analytes at the upper limit of quantification (ULOQ) (the level of analyte above which the assay is outside of linear range) obtained by using the LC-MS/MS and 2D-LC-MS/MS methods and systems of the present invention are shown in FIGS. 14-19. Thus, it can be seen that estrone sulfate has an ULOQ of 50 ng/mL (FIG. 14); free thyroxine has an ULOQ of 100 pg/mL (FIG. 15); 25-hydroxyvitamin D2 has an ULOQ of 250 ng/mL (FIG. 16); 25-hydroxyvitamin D3 has an ULOQ of 250 ng/mL (FIG. 17); estrone has an ULOQ of 500 pg/mL (FIG. 18); and estradiol has an ULOQ of 500 pg/mL (FIG. 19).

Representative LC-MS/MS and 2D-LC-MS/MS calibration curves for selected analytes are shown in FIGS. 20-25. FIG. 20 shows a calibration curve for estrone sulfate where it is seen that the assay is linear over a 1000-fold range. Calibration curves for thyroxine (FIG. 21), 25-hydroxyvitamin D2 (FIG. 22), 25-hydroxyvitamin D3 (FIG. 23), estrone (FIG. 24) and estradiol (FIG. 25) also show linearity over at 100 to 250 fold range. In these figures, the X axis is the concentration, and the Y axis is the ratio of the analyte to an internal standard response.

Representative inter-assay comparison results for the presently disclosed LC-MS/MS and 2D-LC-MS/MS methods versus RIA, CBP, or IA methods are shown in FIGS. 26-30. Thus, it can be seen that using LC-MS/MS provides excellent correlation with RIA for measurement of estrone sulfate (FIG. 26); good correlation but a bias (slope offset) with IA for measurement of free thyroxine (FIG. 27), excellent correlation but a bias (slope offset) for measurement of total 25-hydroxyvitamin D by CBP and average correlation with IA (FIG. 28, panels A and B, respectively); excellent correlation with RIA for measurement of estrone (FIG. 29); and excellent correlation with RIA for measurement of estradiol (FIG. 30). Also, FIG. 31 shows good correlation between the 2D-LC-MS/MS assays described herein for estradiol with an alternate LC-MS/MS strategy involving derivatization. Excellent correlation is observed for samples within the higher analytical range of the derivatization assay (10 pg/mL LLOQ).

FIG. 32 shows results of dialysis losses for thyroxine. The squares (■) show dialysis losses and the diamonds (♦) show effective dialysis for free thyroxine using 96-well equilibrium dialysis plates in accordance with one embodiment of the present invention. This indicates that during the dialysis experiments, free T4 does not degrade or bind to the 96-well plate apparatus (i.e. losses). Further, FIG. 31 indicates that dialysis is complete after approximately 16 hours.

Data showing the validation bias due to ionization effect and recovery for selected analytes are provided in Tables 1 through 7, below. Data showing the accuracy and precision of the presently disclosed LC-MS/MS and 2D-LC-MS/MS methods are provided in Tables 8 through 13. As known by those in the art, acceptable values based on the FDA and CLIA regulations are ≦20% bias or imprecision (% CV) at the LLOQ and ≦15% over the remainder of the assay. See e.g., FDA Guidance: 1.1 Guidance for Industry, Bioanalytical Method Validation, FDA, May 2001, BP, and CLIA Regulation: 42 CFR 493.1253 Standard: Establishment and verification of performance specifications. Subart K, Quality System for Non-waived Testing. Thus, as used herein, "acceptable" or "good" indicates that the assay or aspect of the method being measured meets the NCCLS, FDA and CLIA critieria.

Each of the presently disclosed LC-MS/MS and 2D-LC-MS/MS methods was evaluated for specificity against multiple steroids and/or other potential interferences for a total of up to 60 different analytes (see Examples 1 and 2) at excessive concentrations, for example, 100 μg/dL, to ensure accurate measurement in each assay independent of clinical levels of endogenous and therapeutic agents, such as steroids, which either cross-react in RIA assays or are not discriminated using the specificity provided by MS/MS detection. Additionally, analyte stability was evaluated for all conditions expected from original patient sampling to final result. Proven stability includes sample shipment (−20° C.), sample processing (20° C.; >3 freeze/thaw cycles) and post processing (20° C. and autosampler at 10° C.) to ensure accurate and precise determination of analytes, such as hormone steroids, derived from patient samples (see Examples 1 and 2).

TABLE 1

Estrone Sulfate

| Validation | Bias (%) |
| --- | --- |
| Serum | −3.8-2.6 |
| Lipemia | −0.2 |
| Hemolysis | 0.7 |
| Recovery | 85.0-97.1 |

TABLE 2

Free Thyroxine

| Validation | Bias (%) |
| --- | --- |
| Serum | −6.9-4.8 |
| Lipemia | 1.0 |
| Hemolysis | 12.8 |
| Recovery | 90.5-95.8 |

TABLE 3

25-Hydroxyvitamin D2

| Validation | Bias (%) |
| --- | --- |
| Serum | −3.8-2.2 |
| Lipemia | −5.0 |
| Hemolysis | −5.4 |
| Recovery | 93.2-100.5 |

TABLE 4

25-Hydroxyvitamin D3

| Validation | Bias (%) |
| --- | --- |
| Serum | −8.8-11.9 |
| Lipemia | −0.3 |
| Hemolysis | −1.6 |
| Recovery | 88.8-94.1 |

TABLE 5

Estrone

| Validation | Bias (%) |
| --- | --- |
| Serum | −11.9-7.8 |
| Lipemia | 8.3 |
| Hemolysis | 2.8 |
| Recovery | 97.2-106.9 |

TABLE 6

Estradiol

| Validation | Bias (%) |
|---|---|
| Serum | −4.5-4.0 |
| Lipemia | −5.9 |
| Hemolysis | −2.9 |
| Recovery | 90.0-95.7 |

TABLE 7

Estrone Sulfate

| | Accuracy (%) | | | | Precision (%) | | | |
|---|---|---|---|---|---|---|---|---|
| Conc. (ng/dL) | 10 | 150 | 2500 | 5000 | 10 | 150 | 2500 | 5000 |
| Intra - 1 | −13.1 | −1.6 | 3.0 | 2.1 | 3.2 | 5.4 | 7.3 | 8.2 |
| Intra - 2 | −18.9 | −5.7 | 4.7 | 3.2 | 14.1 | 3.8 | 2.0 | 8.2 |
| Intra - 3 | −7.5 | −9.3 | 8.6 | −0.4 | 3.6 | 4.6 | 6.0 | 7.8 |
| Inter | −13.2 | −5.5 | 5.4 | 0.5 | 9.4 | 5.5 | 5.7 | 7.9 |

TABLE 8

Free Thyroxine

| | Accuracy (%) | | | Precision (%) | | |
|---|---|---|---|---|---|---|
| Conc. (ng/dL) | 0.2 | 5 | 10 | 0.2 | 5 | 10 |
| Intra - 1 | −3.4 | −7.0 | 3.0 | 5.0 | 6.2 | 5.5 |
| Intra - 2 | 0.1 | −1.2 | −0.3 | 5.1 | 5.2 | 2.2 |
| Intra - 3 | −0.4 | 0.6 | 3.7 | 4.4 | 4.1 | 5.5 |
| Inter | −1.3 | −2.5 | 2.1 | 4.8 | 6.0 | 4.8 |

TABLE 9

25-Hydroxyvitamin D2

| | Accuracy (%) | | | | Precision (%) | | | |
|---|---|---|---|---|---|---|---|---|
| Conc. (ng/mL) | 1.0 | 2.5 | 1.00 | 250 | 1.0 | 2.5 | 100 | 250 |
| Intra - 1 | 6.3 | −8.1 | −2.0 | −0.4 | 4.6 | 5.6 | 0.9 | 2.2 |
| Intra - 2 | 13.9 | 8.6 | −2.2 | 1.7 | 3.3 | 6.0 | 2.6 | 4.5 |
| Intra - 3 | 8.7 | 4.2 | −0.1 | 4.2 | 6.8 | 5.2 | 4.4 | 3.7 |
| Inter | 11.3 | 1.6 | −1.4 | 1.3 | 6.9 | 8.9 | 3.0 | 3.9 |

TABLE 10

25-Hydroxyvitamin D3

| | Accuracy (%) | | | | Precision (%) | | | |
|---|---|---|---|---|---|---|---|---|
| Conc. (ng/mL) | 1.0 | 2.5 | 1.00 | 250 | 1.0 | 2.5 | 100 | 250 |
| Intra - 1 | −3.9 | −4.0 | −2.8 | −0.4 | 5.8 | 5.7 | 4.6 | 2.1 |
| Intra - 2 | 6.2 | 4.8 | −1.4 | 1.5 | 11.2 | 4.6 | 3.9 | 5.5 |
| Intra - 3 | 5.9 | 3.7 | −2.1 | −0.4 | 3.0 | 9.9 | 3.0 | 3.9 |
| Inter | 2.7 | 1.5 | −2.1 | 0.3 | 8.5 | 7.8 | 3.7 | 3.9 |

TABLE 11

Estrone

| | Accuracy (%) | | | Precision (%) | | |
|---|---|---|---|---|---|---|
| Conc. (pg/mL) | 2.5 | 250 | 500 | 2.5 | 250 | 500 |
| Intra - 1 | 12.4 | 1.1 | −1.4 | 2.9 | 5.5 | 3.3 |
| Intra - 2 | −0.3 | 9.2 | 4.0 | 7.3 | 2.8 | 2.4 |
| Intra - 3 | 3.6 | 6.3 | 5.1 | 6.3 | 3.8 | 1.6 |
| Inter | 4.8 | 5.5 | 2.6 | 7.4 | 5.1 | 3.7 |

TABLE 12

Estradiol

| | Accuracy (%) | | | | Precision (%) | | | |
|---|---|---|---|---|---|---|---|---|
| Conc. (pg/mL) | 1.0 | 2.5 | 1.00 | 250 | 1.0 | 2.5 | 100 | 250 |
| Intra - 1 | −7.1 | 1.1 | −1.1 | 0.4 | 4.7 | 4.8 | 2.8 | 1.2 |
| Intra - 2 | −7.4 | 1.1 | 6.4 | 6.5 | 4.4 | 6.3 | 1.6 | 4.3 |
| Intra - 3 | 4.7 | 5.6 | 0.6 | 1.4 | 4.7 | 5.6 | 2.6 | 3.5 |
| Inter | −3.3 | 2.7 | 1.9 | 2.8 | 7.4 | 5.2 | 3.9 | 4.1 |

EXAMPLES

Additional data from the analytical validation and standard operating procedures for the presently disclosed method for the quantification of estrone and estradiol by liquid-liquid extraction and 2D-LC-MS/MS, or free thyroxine by dialysis, an optional liquid-liquid extraction, and LC-MS/MS are set forth in the following Examples.

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

2D-LC-MS/MS Analysis for Estrone, Estradiol, and Estrone Sulfate

Estrone and estradiol were validated to 2.5 pg/mL and 1 pg/mL, respectively, from a 1-mL serum sample. Sensitivity and selectivity were generated using heat assisted and guided fragmentation of estradiol to optimize sensitivity. Analytical specificity was generated via 2D LC using gradients in both LC dimensions, heart-cutting and chromato-focusing prior to MS/MS detection. Optimum selectivity was generated following titration of buffer pH and chromatography to enable separation from co-extracted isobaric endogenous interferences, while retaining necessary sensitivity (S/N>20) for accurate quantification in estrone sulfate analysis using LC-MS/MS.

More particularly, estrone (E1) and estradiol (E2) were measured by two-dimensional (2D) liquid chromatography with tandem mass spectrometry detection (2D-LC-MS/MS) after liquid-liquid extraction (LLE). Deuterated $D_4$-Estrone and $D_5$-Estradiol were added as internal standards to serum aliquots. Estrone and Estradiol were extracted from 1 mL serum samples with 8 mL of 9:1 Hexane:Ethyl Acetate. The organic extract was transferred to a fresh tube and back washed with 1 mL aqueous sodium hydroxide solution (pH of about 12), then evaporated and reconstituted in 70:30 Water: Methanol.

Duplicate sets of stripped serum calibrators were analyzed in each batch. All injections were made in singlicate. All samples are injected onto the ARIA TX4 or Transcend TX4 HTLC system (Thermo Fisher, Franklin, Mass., United States of America), where the analytes were first eluted using a separation gradient through an extraction column. Analytes of interest were then transferred onto the analytical column, where chromatographic separation was continued via a gradient. An API5000 triple quadrupole mass spectrometer (MDS-SCIEX, Concord, Ontario, Canada), operating in positive ion Atmospheric Pressure Chemical Ionization (APCI) mode was used for detection.

Quantification of analyte and internal standard was performed in selected reaction monitoring mode (SRM). The back-calculated amount of each analyte in each sample was determined from duplicate calibration curves generated by spiking known amounts of purified estrone and estradiol into charcoal stripped human serum.

Measurement of estrone and estradiol was used to evaluate ovarian function and to evaluate excess or diminished estrogen levels. Analysis of estrone and estradiol by 2D-LC-MS/MS detection was developed to measure levels in serum or plasma samples from children, women and men.

The lower limit of detection using the default sample aliquot of 1 mL was 1.0 pg/mL for Estradiol and 2.5 pg/mL for Estrone.

Definitions

APCI—Atmospheric Pressure Chemical Ionizationl LLE—Liquid-Liquid Extraction; SST—System Suitability Test; 2D-LC-MS/MS—Two-dimensional liquid chromatography with tandem mass spectrometry detection; E1—Estrone; E2-17β-Estradiol or Estradiol; HTLC—High Throughput Liquid Chromatography Specimens A recommended sample is 1.5 mL serum or plasma. Separate within one hour. Store and ship frozen in plastic vial.

| Adult: | 1.5 mL serum or plasma |
| Pediatric: | 1.5 mL serum or plasma |
| Minimum: | 1 mL serum or plasma |

Draw into red top vacutainer tube. Allow clotting to occur for 20 minutes at room temperature (or until clot has retracted). Spin and remove serum to labeled plastic vial. Freeze immediately. Storage is for short term storage (2 weeks): Frozen (≦−20° C.); for long term storage (6 months): Frozen L≦−20° C.). Shipping of specimens is:frozen (≦−20° C.)—on dry ice. Generally, samples drawn into SST tubes are unacceptable for this procedure.

Equipment & Materials

The following materials were used: Standard manual pipetting devices; 1.2 ml MBlock Polypropylene 96 Well Collection Plate (SPE Ware, Inc. Product No. SPE0210); Heat Sealing Foil (SPE Ware, Inc. Product No. AB-0589); Mechanical Shaker, Eberbach Inc.; Rotary Evaporator (rotovap), Speed Vac SC 200, Savant (or equivalent); Class A Volumetric Glass Containers, various sizes; API 5000 Tandem Mass Spectrometer, Sciex, (Toronto, Canada); Turbo V™ Ion Source with APCI probe, Sciex, (Toronto, Canada); Aria TX4 HTLC System, Cohesive Technologies, (MA, USA) consisting of 4 each: 1100 Series Quaternary Pump, 1100 Series Binary Pump, 1100 Series Vacuum Degasser; HTS Twin PAL System Autosampler, CTC Analytics AG (Switzerland); Luna Phenyl-Hexyl Analytical Column, 50×2.0 mm, 5 µm particle size, Phenomenex, (USA) Product No. 00B-4257-B0; Poroshell 300SB-C18 Column, 2.1×75 mm, 5 µm particle size, Agilent Inc., (USA) Product No. 660750-902; 16 mm Flange Caps, Stockwell Scientific, (AZ, USA) Product No. 8558; Vortex Mixer, VWR or equivalent; Combithermo Heat Sealer, Abgene Inc., Product No. AB-0559; 96-Well Centrifuge 5804R Eppendorf or equivalent; 16×100 mm borosilicate glass tubes; Thermo Hot pocket column oven, Thermo Electron Corp. (USA) Product No. 92016-150; Analyst Version 1.4 or greater. Applied Biosystems, (CA, USA); Aria OS Version 1.4 or greater, Cohesive Technologies (MA, USA).

Reagents

The following reagents were used. Water—Type II, Millipore MilliQ or equivalent; Charcoal Stripped Human Serum (Bioreclamation, Inc); Ethyl alcohol USP (AAPER Alcohol, USA); Acetonitrile HPLC grade (EM Science AX0142-1); Methanol (Reagent A.C.S., Fisher Scientific); Isopropanol HPLC Grade (Fisher Scientific, Catalog #A451-4); 17β-Estradiol, Sigma-Aldrich, (USA) Product # E8875 or USP, (USA) Product #1250008; Estrone, Sigma-Aldrich, (USA) Product # E1274 or USP, (USA) Product #1255001; 17β-Estradiol-2,4,16,16,17-$D_5$, CDN Isotopes, (USA) Product # D-5403; Estrone-2,4,16,16-$D_4$, CDN Isotopes, (USA) Product # D-3650; Acetone HPLC Grade (Burdick & Jackson, Catalog #AH010-4); Total Estrogen Stock Solution (10 µg/mL in ethanol) prepared by serial dilution.

The following solvents were used as the mobile phases for liquid chromatography. Eluting and Loading Pump A Mobile Phase (90% Water and 10% Methanol); Loading Pump B Mobile Phase (90% Methanol and 10% Water); and Loading Pump C Mobile Phase (60:30:10 Acetonitrile:Isopropanol: Acetone).

Internal Standard Solution (1 ng/mL $D_5$-Estradiol and 2 ng/mL $D_4$-Estrone) was prepared in 99:1 water:acetonitrile solution. The reconstitution solution (for reconstituting the sample after liquid-liquid extraction) was 70:30 Millipore Water: Methanol. Two needle wash solutions were used: Needle Wash Solution 1 (Aqueous 1% Formic Acid); and Needle Wash Solution 2 (70:30 Acetonitrile: 1N Ammonium Hydroxide).

Total Estrogen Stock Solution (10 µg/mL)-5 µg/mL estrone and 5 µg/mL estradiol was used to prepare intermediate stock solutions for preparation of calibrators. To prepare standards, 0.5 mL of Total Estrogen Stock (10 µg/mL) was diluted to 100 mL with stripped human serum to yield 25 ng/mL E1E2 solution, and 2 mL of the 25 ng/mL solution was diluted to 100 mL in charcoal stripped human serum to yield a 0.5 ng/mL E1E2 solution. The diluted stocks (0.5 ng/mL and 25 ng/mL) were stored at −20° C. Calibration Standards were then prepared as shown in the following table. All standards were prepared in charcoal stripped human serum. The standard curve back-fit data should be 80-120% at LLOQ, 85-115% at other concentrations of expected curve values.

| Standard Preparation Procedure | | | | | |
| --- | --- | --- | --- | --- | --- |
| Standard Number | Standard Concentration (pg/mL) | Stock Solution. Concentration (ng/mL) | Stock Volume (mL) | Final Volume (mL) | Final Concentration (pg/mL) |
| S1 | 1.0 | 0.5 | 1 | 500 | 1.0 |
| S2 | 2.5 | 0.5 | 2.5 | 500 | 2.5 |
| S3 | 5.0 | 0.5 | 5 | 500 | 5.0 |
| S4 | 10 | 0.5 | 10 | 500 | 10 |
| S5 | 25 | 25 | 0.5 | 500 | 25 |
| S6 | 50 | 25 | 1 | 500 | 50 |
| S7 | 100 | 25 | 2 | 500 | 100 |
| S8 | 200 | 25 | 4 | 500 | 200 |

-continued

Standard Preparation Procedure

| Standard Number | Standard Concentration (pg/mL) | Stock Solution. Concentration (ng/mL) | Stock Volume (mL) | Final Volume (mL) | Final Concentration (pg/mL) |
|---|---|---|---|---|---|
| S9 | 350 | 25 | 7 | 500 | 350 |
| S10 | 500 | 25 | 10 | 500 | 500 |

Quality Control

Control pools are prepared in human serum and introduced into use according to the analytically robust procedures. Each run contained duplicates of four control pools, each with a nominal target value.

Quality Control Concentrations

| Control Name | Target concentration (pg/mL) | |
|---|---|---|
| | Estrone | Estradiol |
| Pool 1 | 10 | 10 |
| Pool 2 | 25 | 25 |
| Pool 3 | 115 | 115 |
| Pool 4 | 300 | 300 |

Assay Procedure

The assay was performed as follows. Pipetted 1.0 ml standard, control or patient into the tube with an Eppendorf pipette (or equivalent). Using an Eppendorf Plus repeating pipette with 5 ml tip (or equivalent), added 50 µl Internal Standard Solution to each tube except double blanks. Mix all samples on multi-vortexer for 30 seconds. Added 8 mL 9:1 Hexane:Ethyl Acetate extraction solvent to all tubes and shook on mechanical shaker for 10 minutes. Removed tubes from shaker and spun down all samples in centrifuge up to 2000 rpm. Labeled a separate set of 16×100 mm test tubes, and add 1 mL redistilled water and 1 drop of 1N NaOH to each. Froze aqueous layer of extracted samples and poured into the tubes containing the water and NaOH. Capped and shook on mechanical shaker for 10 minutes. Removed from shaker and spin down all samples in centrifuge up to 2000 rpm. Froze aqueous layer of extracted samples and poured into new tubes. Placed all tubes into a Rotovap (or equivalent) and allow solvent to evaporate for 45 to 60 minutes. Once there was no trace of solvent left in the tubes, remove from Rotovap and reconstitute each with 120 µL E1E2 Reconstitution solution. Covered tubes with parafilm and mixed on multivortexer, 4×30 seconds.

Using an Eppendorf pipette, or equivalent, transfered the reconstituted tubes to a 96-well plate. Placed a heat-sealing foil over the plate and seadl the plate with the heated plate sealer. Centrifuged plate at 3700 rpm at 10° C. for 10 minutes and placed 96-well plate in LC-MS/MS Autosampler.

Liquid Chromatography Procedures

After liquid-liquid extraction and reconstitution in 100 µL, 80 µL of extracted sample was injected into the HTLC system using methanol:water in the mobile phase. The HTLC system is logically divided into two functions: (1) first dimension extraction/separation using a highly selective LC column using a binary gradient; and (2) second dimension separation using an sharper binary gradient of methanol and water and a 5 µm reverse phase analytical column. In this example, a Poroshell 300SBC18 75×2.1, 5 µm column was used for extraction.

In the extraction mode of the HTLC system, the sample was first pumped through the extraction column at a 1 ml/min flow rate using the HTLC loading pump. This separation ensures optimized separation of isobaric interferences and the passage of unwanted coextracted analytes to waste.

After the first dimension separation step, the flow rate was reduced to 0.5 mL/min and combined with 0.5 mL/min of water during transfer and chromatofocussing onto the second dimension phenyl hexyl column. Such HPLC columns are commercially available (e.g., Thermo Hypersil Phenyl hexyl, Phenomenex Luna Phenyl Hexyl)). In the analytical mode of the HTLC, after the sample was chromatofocussed onto the analytical column. A binary gradient from 0% to 90% methanol at 1 mL/min was used, resulting in the separation and increase in peak concentration of estrone and estradiol from other analytes contained in the sample. The separated sample was then transferred to the MS/MS for quantitation. The 2D-LC method is summarized below. Estrone, estradiol, $D_4$-estrone and $D_5$-estradiol elute from the second column at approximately 5.2 minutes (+ or −1 minute).

Estrone and Estradiol 2D-LC Method

| STEP | Start Time (minutes) | Step Duration (seconds) | Loading Pump** (% B) | Flow Rate (mL/minute) | Eluting Pump** (% B) | Flow Rate (mL/minute) | Eluting Pump Gradient Type |
|---|---|---|---|---|---|---|---|
| 1 | 0.00 | 20 | 20 | 0.7 | 0.0 | 1.0 | Isocratic |
| 2 | 0.33 | 124 | 36 | 0.7 | 0.0 | 1.0 | Isocratic |
| 3* | 2.40 | 42 | 41 | 0.5 | 0.0 | 0.5 | Isocratic |
| 4 | 3.10 | 30 | 100 | 1.0 | 23 | 1.0 | Gradient |
| 5 | 3.60 | 40 | 100 | 1.0 | 43 | 1.0 | Gradient |
| 6 | 4.27 | 70 | 100 | 1.0 | 70 | 1.0 | Gradient |
| 7 | 5.43 | 41 | 20 | 1.0 | 90 | 1.0 | Gradient |
| 8 | 6.12 | 45 | 20 | 0.7 | 100 | 1.0 | Gradient |
| 9 | 6.87 | 10 | 20 | 0.7 | 0.0 | 1.0 | Isocratic |

*Step 3: Transfer of eluent from the extraction column at 0.5 mL/minute and chromatofocus with 0.5 ml/Mminute of millipore water provided by the eluting pump.
**Loading and Eluting Buffers: Loading Pump Buffer A 90:10 Millipore Water:Methanol; Loading Pump Buffer B 10:90 Millipore Water:Methanol; Eluting Pump Buffer A Millipore Water; Eluting Pump Buffer B 10:90 Millipore Water:Methanol Mass Spectrometry The flow of liquid solvent from the HTLC system entered the heated nebulizer (APCI) interface of the MS/MS analyzer. The solvent/analyte mixture was first converted to vapor in the heated tubing of the interface. The analytes, contained in the nebulized solvent, were ionized and a positive charge added by the corona discharge needle of the interface, which applies a large voltage to the nebulized solvent/analyte mixture. During heating and ionization of estradiol (E2), the selected interface heater settings of 500° C. enable dehydration of estradiol to the dehydrated moiety at m/z 255.3 that enables the sensitivity gains observed within the underivatized assay described here. The ions passed through the orifice of the instrument and entered the first quadrupole. Quadrupoles 1 and 3 (Q1 and Q3) were the mass filters, allowing selection of ions based on their mass to charge ratio (m/z). Quadrupole 2 (Q2) was the collision cell, where ions were fragmented.

The first quadrupole of the MS/MS (Q1) selected for molecules with the mass to charge ratio of estrone/estradiol (271.3/255.3±0.5 m/z or mass units). Ions with these nm/z passed to the collision chamber (Q2), while ions with any other m/z collided with the sides of the quadrupole and were fragmented. Ions entering Q2 collided with neutral gas molecules and fragment. This process is called Collisionally Activated Dissociation (CAD). The CAD gas used in this example was nitrogen resulting in the generation of fragment (products). The fragment ions generated were passed into quadrupole 3 (Q3), where the two fragment ions of estradiol to be measured (m/z 159.0±0.5 m/z and 133.0±0.5 m/z or mass units) and 2 ions for estrone (m/z 159.0±0.5 m/z and 133.0±−0.5 m/z or mass units) were selected for, while other ions were screened out. The selected fragment ions were collected by the detector. The same process was carried out for an internal standards, which were 5-deuterated estradiol and 4-deuterated estrone molecules. Thus, the selected MS/MS transitions (nominal masses) measured were as follows: Estradiol m/z 255 to 159 and 133; Estrone m/z 271 to 159 and 133; $D_5$-Estradiol m/z 260 to 161; and $D_4$-Estrone m/z 275 to 161.

Selected MS/MS parameters were as follows: Dwell time: 100 msec for each estradiol and estrone transition, and 50 msec for each internal standard transition; Unit mass resolution in both resolving g quadrupoles (Q1 and Q3); Curtain Gas: 10; CADGas: 6; NC: µA; Temp: 500° C.; GS1: 20; GS2: 0; CE: 27 for estradiol and internal standards and 35 for estrone and internal standards.

As ions collide with the detector, they produce a pulse of electrons. The pulse was converted to a digital signal, which was counted to provide an ion count. The acquired data was relayed to the computer, which plotted counts of the ions collected vs. time. Areas of the chromatohgraphic peaks generated were computer-measured, response factors (ratio of analyte to internal standard responses) were generated from calibration materials spiked into stripped matrix calibrators at known concentrations, and estradiol and estrone concentrations in unknown samples were thereby quantitated by back-calculating the area response ratios of analyte to internal standards against the constructed calibration curves.

The HTLC system can be operated with 1 to 4 channels in parallel, with each channel incorporating 1 or more columns. Given that a single assay requires about 3-6 minutes to traverse the column or columns, by staggering the start time on each column, a 4-fold multiplexed system can inject four times as many test samples into the MS/MS instrument than with a single column. Thus, a set of 1000 samples may be assayed for estrone and estradiol in 1 day using HTLC 4 channel muliplexing, as opposed to 4 days when using a single channel system. Furthermore, following transfer of samples to the autosampler, no further operator handling of samples is required, as the HTLC may be computer-controlled to perform the subsequent purification and analysis steps in a fully on-line configuration.

Calculations

Calibration curves are constructed using the software system (Analyst) that controls the mass spectrometer. Calibration curves are generated by assigning the known concentrations to calibrators to generate a response ratio of analyte to internal standard versus concentration of analyte added [FIG. 20-26]. The concentrations of unknown samples are automatically calculated by comparing the response ratio of analyte to internal standard observed in measuring unknown samples to the calibration curve generated above. Samples that have an initial value greater than 500 pg/mL are diluted and re-extracted/analyzed to provide a result within the linear range of the assay.

Assay Performance Characteristics

A quantitative bioanalytical method for the determination of estrone and estradiol in human serum using LLE and 2D LC-MS/MS detection was developed and validated. The assay accuracy and precision was shown to be specific for the analysis of estrone and estradiol.

Spiked standard samples at nine (estrone) and ten (estradiol) concentrations were used to generate a weighted (1/x) linear regression calibration curve, which covered the range from 2.5 to 500 pg/mL for estrone and 1 to 500 pg/mL for estradiol. Average inaccuracies and imprecision <20% at the LLOQ and <15% throughout the remainder of the range were observed. The correlation coefficients of the curves were greater than 0.98. Sample dilution was evaluated for both estrone and estradiol. Acceptable bias was observed for all samples within the analytical ranges of both assays.

Selectivity

Blank Matrix Interference

Quadruplicate injections of stripped serum were injected to determine the degree of blank matrix interference for each analyte. Matrix responses were <20% of the mean LLOQ for estrone in all 6 lots tested and <20% of the mean LLOQ for estradiol in 5 of 6 lots tested.

Anticoagulant Effect on Matrix.

The effect of EDTA and heparin as anticoagulants was tested by drawing four healthy volunteers using red top serum collection tubes and vacutainers containing Sodium Heparin and EDTA anticoagulants. The results of the heparin and EDTA tubes were compared to the results from the serum collection tubes. Variation of sample type and anticoagulant exhibited a bias <±15% for measurement of estrone and estradiol. Thus, plasma samples collected with Heparin and EDTA are acceptable specimen types.

| Anticoagulant Effect on Estrone and Estradiol Measurement | | | |
|---|---|---|---|
| | Concentration (pg/mL) | | |
| Sample | Serum | Heparin | EDTA |
| Estrone | 32.200 | 27.953 | 28.590 |
| | 20.213 | 19.387 | 20.425 |
| | 162.481 | 151.423 | 156.020 |
| | 17.925 | 17.841 | 16.521 |
| Mean | 58.205 | 54.151 | 55.389 |
| Mean Matrix Effect (%) | NA | −6.96 | −4.84 |
| n | 4 | 4 | 4 |
| Estradiol | 22.475 | 21.226 | 20.300 |
| | 40.975 | 42.657 | 42.183 |
| | 181.435 | 184.180 | 193.202 |
| | 13.833 | 13.635 | 13.092 |
| Mean | 64.680 | 65.425 | 67.194 |
| Mean Matrix Effect (%) | NA | 1.15 | 3.89 |
| n | 4 | 4 | 4 |

Effect of Lipemia and Hemolysis in the Matrix.

The effect of lipemia and hemolysis on the quantitative result was determined by spiking pooled patient serum with 5% by volume of lipid solution or lysed red blood cells. The samples were run in quadruplicate and the results compared to the results of the pool before contamination. Bias was <±15% following addition of lipemic or hemolyzed material was observed for both estrone and estradiol. Thus, lipemic and hemolyzed samples may be processed using this assay.

Internal Standard Interference.

Internal standards ($D_4$-estrone and $D_5$-estradiol) working solution was spiked into charcoal stripped serum and tested in quadruplicate to evaluate the presence of unlabeled analyte. Internal standards ($D_4$-estrone and $D_5$-estradiol) interference responses were less than 20% of the mean LLOQ response for both estrone and estradiol.

Matrix Effect.

The matrix effect was calculated at low, mid and high level concentrations. The matrix effect for the internal standard was measured at a single concentration. A minimum of 4 samples per QC level were analyzed for both analytes to determine matrix effect on quantitative result. Matrix effects were less than 15% for all analytes (estrone, estradiol and $D_4$-estrone and $D_5$-estradiol internal standards) tested when comparing water and pooled samples.

Effect of Lipemia and Hemolysis on Estrone and Estradiol

| | Concentration (pg/mL) | | |
|---|---|---|---|
| Sample | Serum | Lipemic | Hemolyzed |
| Estradiol | 118.286 | 118.877 | 113.430 |
| | 108.600 | 120.709 | 114.765 |
| | 108.772 | 120.159 | 114.246 |
| | 113.406 | 126.448 | 119.172 |
| Mean | 112.266 | 121.548 | 115.403 |
| Mean Matrix Effect (%) | NA | 8.27 | 2.79 |
| n | 4 | 4 | 4 |
| Estrone | 108.159 | 97.741 | 114.344 |
| | 108.131 | 103.348 | 96.851 |
| | 105.072 | 98.358 | 104.242 |
| | 102.476 | 99.496 | 96.149 |
| Mean | 105.960 | 99.736 | 102.897 |
| Mean Matrix Effect (%) | NA | −5.87 | −2.89 |
| n | 4 | 4 | 4 |

Estrone Matrix Effect

| | Sample Matrix | | | | | |
|---|---|---|---|---|---|---|
| | Millipore Water | | | Pooled Human Serum | | |
| Post-Column Infusion Level | Analyte Response (cps) | Internal Standard Response (cps) | Ratio | Analyte Response (cps) | Internal Standard Response (cps) | Ratio |
| Low Infusion | 13704.285 | 13282.465 | 1.032 | 12977.458 | 14357.420 | 0.904 |
| | 11983.207 | 12280.880 | 0.976 | 12726.749 | 15154.084 | 0.840 |
| | 13447.370 | 14129.109 | 0.952 | 13866.153 | 14011.588 | 0.990 |
| | 12912.166 | 13543.690 | 0.953 | 12798.316 | 14614.364 | 0.876 |
| MARR per Conc. | NA | NA | 0.978 | NA | NA | 0.902 |
| % Change | NA | NA | NA | NA | NA | −7.76 |
| Mid Infusion | 34680.714 | 12444.598 | 2.787 | 37110.060 | 13962.366 | 2.658 |
| | 34353.842 | 11496.604 | 2.988 | 35363.380 | 13567.318 | 2.607 |
| | 38284.618 | 13119.045 | 2.918 | 37102.053 | 14459.360 | 2.566 |
| | 36175.359 | 12448.411 | 2.906 | 37599.353 | 15799.305 | 2.380 |
| MARR per Conc. | NA | NA | 2.900 | NA | NA | 2.553 |
| % Change | NA | NA | NA | NA | NA | −11.98 |
| High Infusion | 123737.835 | 11465.898 | 10.792 | 132777.319 | 14635.791 | 9.072 |
| | 109476.758 | 11070.122 | 9.889 | 123422.614 | 14005.516 | 8.812 |
| | 130085.379 | 12808.997 | 10.156 | 142380.844 | 14729.975 | 9.666 |
| | 124071.128 | 11506.322 | 10.783 | 133162.192 | 13750.007 | 9.685 |
| MARR per Conc. | NA | NA | 10.405 | NA | NA | 9.309 |
| % Change | NA | NA | NA | NA | NA | −10.54 |

Estradiol Matrix Effect

| | Sample Matrix | | | | | |
|---|---|---|---|---|---|---|
| | Millipore Water | | | Low Pooled Human Serum | | |
| Post-Column Infusion Level | Analyte Response (cps) | Internal Standard Response (cps) | Ratio | Analyte Response (cps) | Internal Standard Response (cps) | Ratio |
| Low Infusion | 9289.430 | 15134.202 | 0.614 | 10756.094 | 16273.794 | 0.661 |
| | 9142.882 | 14970.197 | 0.611 | 9623.939 | 15742.986 | 0.611 |
| | 9178.822 | 14245.804 | 0.644 | 10323.741 | 15672.658 | 0.659 |
| | 9115.187 | 14769.048 | 0.617 | 10657.311 | 16270.173 | 0.655 |

-continued

Estradiol Matrix Effect

| | Sample Matrix | | | | | |
|---|---|---|---|---|---|---|
| | Millipore Water | | | Low Pooled Human Serum | | |
| Post-Column Infusion Level | Analyte Response (cps) | Internal Standard Response (cps) | Ratio | Analyte Response (cps) | Internal Standard Response (cps) | Ratio |
| MARR per Conc. | NA | NA | 0.622 | NA | NA | 0.646 |
| % Change | NA | NA | NA | NA | NA | 4.02 |
| Mid Infusion | 32753.289 | 14367.449 | 2.280 | 34773.500 | 15118.142 | 2.300 |
| | 33992.565 | 14615.840 | 2.326 | 33326.110 | 14131.532 | 2.358 |
| | 34038.400 | 14387.971 | 2.366 | 34970.558 | 14653.828 | 2.386 |
| | 33191.028 | 13699.972 | 2.423 | 33447.218 | 14509.296 | 2.305 |
| MARR per Conc. | NA | NA | 2.348 | NA | NA | 2.338 |
| % Change | NA | NA | NA | NA | NA | −0.47 |
| High Infusion | 123906.209 | 13814.999 | 8.969 | 147602.652 | 15918.071 | 9.273 |
| | 129674.464 | 13636.345 | 9.509 | 140981.287 | 16008.385 | 8.807 |
| | 126576.356 | 13173.822 | 9.608 | 136601.192 | 15250.626 | 8.957 |
| | 128043.106 | 13263.078 | 9.654 | 149499.158 | 16614.989 | 8.998 |
| MARR per Conc. | NA | NA | 9.435 | NA | NA | 9.009 |
| % Change | NA | NA | NA | NA | NA | −4.52 |

For both the estrone and estradiol matrix effect tables, matrix effect = [(Mean Analyte to Internal standard ratio in pooled serum)/Mean Analyte to Internal standard ratio in water)] − 1, expressed as a percentage

A. Intra-Assay Precision

The intra-assay precision of the analytical method was calculated for three assays using patient pools (Pool 1 at 10 pg/mL, Pool 2 at 25 pg/mL, Pool 3 at 115 pg/mL, and Pool 4 at 300 pg/mL, all concentrations are approximate). The following tables show the data for these pools, as well as, the data from quality controls made from spiked charcoal stripped human serum at four concentrations (1.0 pg/mL, 2.5 pg/mL, 250 pg/mL, and 500 pg/mL).

Estrone Intra-assay Precision

| | Intra-Assay % CV | | | | | | | |
|---|---|---|---|---|---|---|---|---|
| Assay No. | Pool 1 | Pool 2 | Pool 3 | Pool 4 | 1.0 | 2.5 | 250 | 500 |
| 1 | 4.50 | 5.03 | 4.42 | 2.69 | 15.35 | 2.91 | 5.52 | 3.30 |
| 2 | 5.21 | 4.71 | 3.64 | 4.30 | 19.56 | 7.16 | 2.76 | 2.39 |
| 3 | 3.47 | 2.91 | 1.87 | 2.95 | 29.91 | 6.30 | 3.81 | 1.63 |

Estradiol Intra-assay Precision

| | Intra-Assay % CV | | | | | | | |
|---|---|---|---|---|---|---|---|---|
| Assay No. | Pool 1 | Pool 2 | Pool 3 | Pool 4 | 1.0 | 2.5 | 250 | 500 |
| 1 | 2.27 | 3.43 | 1.80 | 3.23 | 4.72 | 4.77 | 2.81 | 1.15 |
| 2 | 4.31 | 3.04 | 1.34 | 2.56 | 4.44 | 6.26 | 1.60 | 4.33 |
| 3 | 5.59 | 1.35 | 3.64 | 4.86 | 4.70 | 3.92 | 2.61 | 3.46 |

Reproducibility

The inter-assay precision was calculated from the overall data from the precision assays for each of the QC samples. As shown in the inter-assay tables, the method has good inter-assay precision.

Estrone Inter-Assay Precision

| | Pool 1 | Pool 2 | Pool 3 | Pool 4 | 1.0 | 2.5 | 250 | 500 |
|---|---|---|---|---|---|---|---|---|
| Average | 10.34 | 26.16 | 116.91 | 309.26 | 1.22 | 2.62 | 263.79 | 512.80 |
| % CV | 4.88 | 4.59 | 4.65 | 5.37 | 29.23 | 7.39 | 5.08 | 3.67 |
| N | 18 | 18 | 18 | 18 | 18 | 18 | 18 | 18 |

Estradiol Inter-Assay Precision

| | Pool 1 | Pool 2 | Pool 3 | Pool 4 | 1.0 | 2.5 | 250 | 500 |
|---|---|---|---|---|---|---|---|---|
| Average | 10.83 | 23.94 | 114.18 | 293.45 | 0.97 | 2.57 | 254.82 | 513.87 |
| % CV | 4.36 | 3.53 | 3.33 | 4.86 | 7.39 | 5.22 | 3.94 | 4.10 |
| N | 18 | 18 | 18 | 18 | 18 | 18 | 18 | 18 |

Accuracy

The inter-assay accuracy was determined by calculating the percent bias for samples of known concentrations. Stripped human serum was spiked to 1.0 pg/mL, 2.5 pg/mL, 250 pg/mL, and 500 pg/mL and then assayed 6 times in three different runs. As shown in the intra-assay tables, the method has good inter-assay accuracy.

Estrone Inter-assay Accuracy Data

| System Precision | 1.0 pg/mL | 2.5 pg/mL | 250 pg/mL | 500 pg/mL |
|---|---|---|---|---|
| Expected Result | 1.0 | 2.5 | 250 | 500 |
| Average Result | 1.22 | 2.62 | 263.79 | 512.80 |
| % Bias | 22.13 | 4.79 | 5.51 | 2.56 |

| Estradiol Inter-assay Accuracy Data | | | | |
|---|---|---|---|---|
| System Precision | 1.0 pg/mL | 2.5 pg/mL | 250 pg/mL | 500 pg/mL |
| Expected Result | 1.0 | 2.5 | 250 | 500 |
| Average Result | 0.97 | 2.57 | 254.82 | 513.87 |
| % Bias | −3.28 | 2.70 | 1.93 | 2.77 |

Spike and Recovery

A patient pool and stripped human serum calibrator were spiked with Estrone and Estradiol. Recovery was performed by comparing the measured results of samples spiked with 50, 200 and 400 pg/mL of standard material against expected values. Samples were analyzed in quadruplicate. Both estrone and estradiol exhibited recoveries >85% and <115%.

Specificity

Specificity was tested by adding 1 μg of the steroids listed below to 1 mL (equivalent to 100 μg/dL) of water before extraction and injection. Where specificity is being further evaluated, lower concentrations of analytes are used (i.e. 100 ng/mL or 10 ng/mL). Acceptability Criteria: Response less than the LLOQ at the appropriate retention time in excess of physiologically significant amounts of potential interfering analytes.

It was found that estrone analysis is not affected by the presence of circulating hormones or drugs at physiological concentrations in the testing. The liquid-liquid extraction step employed is known to exclude extraction of estrone sulfate during sample processing, thus, it is apparent that the estrone sulfate material tested contains estrone as an impurity at approximately 0.03% and thus, the assay is considered specific for the measurement of estrone. Also, estradiol analysis was not affected by the presence of the circulating hormones and drugs tested at relevant physiological levels.

| Estrone and Estradiol Spike and Recovery | | | | |
|---|---|---|---|---|
| | Concentration Added (pg/mL) | | | |
| | 0.000 | 50.000 | 200.000 | 400.000 |
| | Concentration Measured (pg/mL) | | | |
| Estrone Stripped Serum | 10.716 | 61.395 | 199.547 | 394.156 |
| | 11.578 | 58.841 | 198.228 | 423.264 |
| | 12.133 | 65.149 | 216.259 | 400.486 |
| | 10.381 | 59.695 | 206.891 | 431.507 |
| Mean | 11.202 | 61.270 | 205.231 | 412.353 |
| Expected Conc. | NA | 61.202 | 211.202 | 411.202 |
| Recovery (%) | NA | 100.1 | 97.2 | 100.3 |
| n | 4 | 4 | 4 | 4 |
| Estrone Pooled Serum | 24.513 | 83.123 | 234.620 | 434.374 |
| | 27.357 | 82.876 | 228.706 | 431.772 |
| | 27.574 | 81.036 | 230.123 | 434.208 |
| | 25.478 | 78.861 | 231.405 | 433.010 |
| Mean | 26.231 | 81.474 | 231.214 | 433.341 |
| Expected Conc. | NA | 76.231 | 226.231 | 426.231 |
| Recovery (%) | NA | 106.9 | 102.2 | 101.7 |
| n | 4 | 4 | 4 | 4 |
| Estradiol Stripped Serum | 10.029 | 54.400 | 197.858 | 362.120 |
| | 9.950 | 56.014 | 197.599 | 373.907 |
| | 10.542 | 59.706 | 200.453 | 373.998 |
| | 9.757 | 56.920 | 204.747 | 366.630 |
| Mean | 10.070 | 56.760 | 200.164 | 369.164 |
| Expected Conc. | NA | 60.070 | 210.070 | 410.070 |
| Recovery (%) | NA | 94.5 | 95.3 | 90.0 |
| n | 4 | 4 | 4 | 4 |
| Estradiol Pooled Serum | 21.627 | 67.816 | 207.658 | 375.399 |
| | 23.183 | 70.755 | 202.194 | 390.105 |
| | 24.317 | 70.378 | 206.603 | 411.400 |
| | 23.876 | 71.583 | 221.472 | 400.773 |
| Mean | 23.251 | 70.133 | 209.482 | 394.419 |
| Expected Conc. | NA | 73.251 | 223.251 | 423.251 |
| Recovery (%) | NA | 95.7 | 93.8 | 93.2 |
| n | 4 | 4 | 4 | 4 |

| Estrone Hormone Specificity | | | |
|---|---|---|---|
| Steroid | Amount added (pg/mL) | Measured Concentration (pg/mL) | Relative Response (%) (LLOQ of 2.5 pg/mL = 0.00025%) |
| Dihydrotestosterone | 1000000 | 6.234 | 0.00062 |
| Androstenediol | 1000000 | 0.000 | 0.00000 |
| 5-androsten-3,11,17-trione | 1000000 | 0.000 | 0.00000 |
| Androstenedione | 1000000 | 0.000 | 0.00000 |
| 17a-Methyltestosterone | 1000000 | 0.000 | 0.00000 |
| Cortisone | 1000000 | 0.000 | 0.00000 |
| Epitestosterone | 1000000 | 0.000 | 0.00000 |
| Dehydroepiandrostenedione | 1000000 | 0.000 | 0.00000 |
| Dexamethasone | 1000000 | 0.000 | 0.00000 |
| 5a-androstan-3b,17b-diol | 1000000 | 0.000 | 0.00000 |
| 5b-androstan-3a,17b-diol | 1000000 | 0.000 | 0.00000 |
| Epiandrosterone | 1000000 | 0.000 | 0.00000 |
| 17a-Hydroxyprogesterone | 1000000 | 0.000 | 0.00000 |
| 11-Desoxycortisol | 1000000 | 0.000 | 0.00000 |
| Prednisone | 1000000 | 0.000 | 0.00000 |
| Estriol | 1000000 | 7.741 | 0.00077 |
| Corticosterone | 1000000 | 0.385 | 0.00004 |
| Androsterone | 1000000 | 0.000 | 0.00000 |
| Prednisolone | 1000000 | 0.000 | 0.00000 |
| 17-Hydroxypregnenolone | 1000000 | 0.000 | 0.00000 |
| Progesterone | 1000000 | 0.000 | 0.00000 |
| 20a-Hydroxy-progesterone | 1000000 | 0.000 | 0.00000 |
| 20b-Hydroxy-progesterone | 1000000 | 0.000 | 0.00000 |
| Beclomethasone | 1000000 | 0.000 | 0.00000 |
| Triamcinolone Acetonide | 1000000 | 0.000 | 0.00000 |
| Fluticasone Propionate | 1000000 | 0.000 | 0.00000 |
| Pregnanetriol | 1000000 | 2.385 | 0.00024 |
| Tetrahydrocortisol | 1000000 | 0.000 | 0.00000 |
| Tetrahydrocortisone | 1000000 | 0.000 | 0.00000 |
| Pregnenolone sulphate | 1000000 | 0.000 | 0.00000 |
| Ethinyl Estradiol | 100000 | 0.845 | 0.00085 |
| Budesonide | 1000000 | 0.000 | 0.00000 |
| Pregnanediol | 1000000 | 1.828 | 0.00018 |
| Desoxycorticosterone | 1000000 | 0.951 | 0.00010 |
| Cortisol | 1000000 | 0.000 | 0.00000 |
| 21-Desoxycortisol | 1000000 | 0.000 | 0.00000 |
| Pregnenolone | 1000000 | 0.000 | 0.00000 |
| Andrenosterone | 1000000 | 0.000 | 0.00000 |
| Aldosterone | 1000000 | 0.000 | 0.00000 |
| Dihydroandrosterone | 1000000 | 0.000 | 0.00000 |
| 11a Hydroxy-Progesterone | 1000000 | 0.000 | 0.00000 |
| Testosterone | 1000000 | 0.000 | 0.00000 |
| Estrone-3-Sulfate | 1000000 | 339.301 | 0.03393 |

| Estradiol Hormone Specificity | | | |
|---|---|---|---|
| Steroid | Amount added (pg/mL) | Measured Concentration (pg/mL) | Relative Response (%) (LLOQ of 1 pg/mL = 0.00010%) |
| Dihydrotestosterone | 1000000 | 0.000 | 0.00000 |
| Androstenediol | 100000 | 2.763 | 0.00276 |
| 5-androsten-3,11,17-trione | 1000000 | 0.000 | 0.00000 |

| | | | |
|---|---|---|---|
| -continued | | | |
| Androstenedione | 1000000 | 0.000 | 0.00000 |
| 17a-Methyltestosterone | 1000000 | 0.000 | 0.00000 |
| Cortisone | 1000000 | 0.000 | 0.00000 |
| Epitestosterone | 1000000 | 0.000 | 0.00000 |
| Dehydroepiandrostenedione | 1000000 | 0.000 | 0.00000 |
| Dexamethasone | 1000000 | 0.000 | 0.00000 |
| 5a-androstan-3b,17b-diol | 1000000 | 0.000 | 0.00000 |
| 5b-androstan-3a,17b-diol | 1000000 | 0.000 | 0.00000 |
| Epiandrosterone | 1000000 | 0.000 | 0.00000 |
| 17a-Hydroxyprogesterone | 1000000 | 0.000 | 0.00000 |
| 11-Desoxycortisol | 1000000 | 1.739 | 0.00017 |
| Prednisone | 1000000 | 0.000 | 0.00000 |
| Estriol | 10000 | 2.937 | 0.02937 |
| Corticosterone | 1000000 | 0.000 | 0.00000 |
| Androsterone | 1000000 | 0.000 | 0.00000 |
| Prednisolone | 1000000 | 0.000 | 0.00000 |
| 17-Hydroxypregnenolone | 1000000 | 4.560 | 0.00046 |
| Progesterone | 1000000 | 0.000 | 0.00000 |
| 20a-Hydroxy-progesterone | 1000000 | 0.000 | 0.00000 |
| 20b-Hydroxy-progesterone | 1000000 | 0.000 | 0.00000 |
| Beclomethasone | 1000000 | 0.000 | 0.00000 |
| Triamcinolone Acetonide | 1000000 | 0.611 | 0.00006 |
| Fluticasone Propionate | 1000000 | 0.000 | 0.00000 |
| Pregnanetriol | 1000000 | 1.434 | 0.00014 |
| Tetrahydrocortisol | 1000000 | 9.511 | 0.00095 |
| Tetrahydrocortisone | 1000000 | 0.000 | 0.00000 |
| Pregnenolone sulphate | 1000000 | 0.000 | 0.00000 |
| Ethinyl Estradiol | 100000 | 0.937 | 0.00094 |
| Budesonide | 1000000 | 0.417 | 0.00004 |
| Pregnanediol | 1000000 | 0.000 | 0.00000 |
| Desoxycorticosterone | 1000000 | 0.000 | 0.00000 |
| Cortisol | 1000000 | 0.000 | 0.00000 |
| 21-Desoxycortisol | 1000000 | 0.000 | 0.00000 |
| Pregnenolone | 1000000 | 0.000 | 0.00000 |
| Andrenosterone | 1000000 | 0.000 | 0.00000 |
| Aldosterone | 1000000 | 0.000 | 0.00000 |
| Dihydroandrosterone | 1000000 | 0.000 | 0.00000 |
| 11a Hydroxy-Progesterone | 1000000 | 0.000 | 0.00000 |
| Testosterone | 1000000 | 0.000 | 0.00000 |
| Estrone-3-Sulfate | 100000 | 0.000 | 0.00000 |

Stability

Stability in human serum was demonstrated at the following conditions for the times shown below.

| Storage Condition | Estrone | Estradiol |
|---|---|---|
| Room Temperature | 6 days | 6 days |
| Refrigerated (4° C.) | 48 hours | 48 hours |
| Frozen (−20° C.) | 33 months | 32 months |
| Freeze Thaw | 3 cycles | 3 cycles |
| Whole Blood | 48 hours | 48 hours |
| Autosampler | 72 hours | 72 hours |

Sensitivity

The lower limit of quantitation was determined to be 1.0 pg/mL for estradiol and 2.5 pg/mL for estrone using a sample size of 1 mL with 80 µL being injected into the 2D-LC-MS/MS system.

Inter-Assay Comparison

A. Radioimmunoassay Compared to 2D LC-MS/MS.

A minimum of 50 routine samples representing the physiological range were analyzed by 2D LC-MS/MS and RIA following extraction/off-line chromatographic separation for estrone and estradiol and LC-MS/MS with derivatization for estradiol.

The inter-assay comparison of estrone RIA to LC-LC-MS/MS yielded an average bias of 5.46% for samples within the analytical range of both assays. Comparison of data throughout the range generated a slope of 0.9005 with a correlation coefficient of 0.8962; thus, estrone assay-to-assay cross-validation was successful (FIG. 29). Inter-assay comparison of estradiol RIA to LC-LC-MS/MS yielded an average bias of 2.22% for samples within the analytical range of both assays. Comparison of data throughout the range generated a slope of 1.1392 with a correlation coefficient of 0.9776; thus, estradiol inter-assay comparison was successful (FIG. 30). Inter-assay comparison of LC-MS/MS with derivatization compared to LC-LC-MS/MS yielded an average bias of −0.51% (combined data for both Tables below) for samples within the analytical range of both assays. Comparison of data throughout the range generated a slope of 0.9844 with a correlation coefficient of 0.9926 (FIG. 31).

| Estrone Inter-assay Comparison of Radioimmunoassay to 2D LC-MS/MS | | | |
|---|---|---|---|
| | Concentration (pg/mL) | | |
| Sample # | RIA | LC-LC-MS/MS | Bias (%) |
| Sample 12 | 53 | 58.387 | 10.16 |
| Sample 14 | 45 | 40.046 | −11.01 |
| Sample 15 | 60 | 49.222 | −17.96 |
| Sample 16 | 12 | 11.171 | −6.91 |
| Sample 17 | 82 | 67.171 | −18.08 |
| Sample 19 | BLQ | 8.561 | NA |
| Sample 20 | 8 | 12.399 | 54.99 |
| Sample 25 | 59 | 52.737 | −10.62 |
| Sample 31 | 8 | 13.281 | 66.01 |
| Sample 33 | 44 | 43.813 | −0.42 |
| Sample 38 | 45 | 45.408 | 0.91 |
| Sample 39 | 6 | 13.919 | 131.98 |
| Sample 42 | 52 | 54.994 | 5.76 |
| Sample 44 | 49 | 51.138 | 4.36 |
| Sample 46 | 22 | 25.341 | 15.19 |
| Sample 47 | 31 | 35.076 | 13.15 |
| Sample 48 | BLQ | 15.587 | NA |
| Sample 51 | 90 | 76.809 | −14.66 |
| Sample 52 | 57 | 57.380 | 0.67 |
| Sample 53 | 27 | 28.932 | 7.16 |
| Sample 54 | 43 | 30.371 | −29.37 |
| Sample 55 | 21 | 21.693 | 3.30 |
| Sample 56 | 42 | 30.132 | −28.26 |
| Sample 57 | 27 | 28.123 | 4.16 |
| Sample 58 | 48 | 53.190 | 10.81 |
| Sample 59 | 68 | 62.183 | −8.55 |
| Sample 60 | 36 | 49.805 | 38.35 |
| Sample 61 | 130 | 151.848 | 16.81 |
| Sample 62 | 76 | 79.513 | 4.62 |
| Sample 63 | 73 | 84.343 | 15.54 |
| Sample 64 | 102 | 106.993 | 4.90 |
| Sample 66 | 33 | 23.136 | −29.89 |
| Sample 67 | 100 | 80.956 | −19.04 |
| Sample 68 | 17 | 17.714 | 4.20 |
| Sample 69 | 62 | 46.039 | −25.74 |
| Sample 70 | 41 | 48.489 | 18.27 |
| Sample 71 | 29 | 36.534 | 25.98 |
| Sample 72 | 57 | 47.071 | −17.42 |
| Sample 73 | 28 | 39.740 | 41.93 |
| Sample 74 | 25 | 30.986 | 23.94 |
| Sample 75 | 51 | 47.044 | −7.76 |
| Sample 76 | 42 | 43.604 | 3.82 |
| Sample 77 | 9 | 11.251 | 25.01 |
| Sample 78 | 37 | 33.795 | −8.66 |
| Sample 79 | 42 | 44.081 | 4.95 |
| Sample 80 | 19 | 21.918 | 15.36 |
| Sample 81 | 88 | 64.153 | −27.10 |
| Sample 82 | 78 | 75.737 | −2.90 |
| Sample 83 | 107 | 90.226 | −15.68 |
| Sample 84 | 57 | 51.286 | −10.02 |
| Average Bias = | | | 5.46 |

Bias (%) = (Total LC-LC-MS/MS result − RIA result)/RIA result, expressed as a percentage
Samples were selected in sequential order following cross-validation of Estradiol LC-MS/MS to LC-LC-MS/MS to coincide with anticipated measurable levels in the Estrone RIA assay.
BLQ = below limit of quantification.

Estradiol Inter-assay Comparison of Radioimmunoassay to 2D LC-MS/MS

| Sample # | Concentration (pg/mL) RIA | LC-LC-MS/MS | Bias (%) |
|---|---|---|---|
| Sample 12 | 14 | 13.512 | −3.49 |
| Sample 14 | 19 | 11.612 | −38.88 |
| Sample 15 | 18 | 9.950 | −44.72 |
| Sample 16 | 18 | 17.069 | −5.17 |
| Sample 17 | 188 | 203.458 | 8.22 |
| Sample 19 | 25 | 21.031 | −15.88 |
| Sample 20 | 10 | 10.688 | 6.88 |
| Sample 25 | 92 | 149.479 | 62.48 |
| Sample 31 | 12 | 8.816 | −26.53 |
| Sample 33 | 28 | 24.187 | −13.62 |
| Sample 38 | 66 | 79.085 | 19.83 |
| Sample 39 | 10 | 8.092 | −19.08 |
| Sample 42 | 78 | 82.430 | 5.68 |
| Sample 44 | 74 | 86.914 | 17.45 |
| Sample 46 | 23 | 22.228 | −3.36 |
| Sample 47 | 28 | 25.616 | −8.51 |
| Sample 48 | 17 | 16.038 | −5.66 |
| Sample 51 | 152 | 181.717 | 19.55 |
| Sample 52 | 84 | 89.387 | 6.41 |
| Sample 53 | 42 | 45.092 | 7.36 |
| Sample 54 | 48 | 50.658 | 5.54 |
| Sample 55 | 17 | 12.738 | −25.07 |
| Sample 56 | 32 | 30.153 | −5.77 |
| Sample 57 | 34 | 33.255 | −2.19 |
| Sample 58 | 27 | 25.110 | −7.00 |
| Sample 59 | 44 | 44.229 | 0.52 |
| Sample 60 | 26 | 27.235 | 4.75 |
| Sample 61 | 223 | 248.650 | 11.50 |
| Sample 62 | 134 | 139.889 | 4.39 |
| Sample 63 | 138 | 144.874 | 4.98 |
| Sample 64 | 216 | 235.982 | 9.25 |
| Sample 66 | 12 | 7.893 | −34.23 |
| Sample 67 | 46 | 41.866 | −8.99 |
| Sample 68 | 21 | 18.206 | −13.30 |
| Sample 69 | 61 | 70.482 | 15.54 |
| Sample 70 | 57 | 65.890 | 15.60 |
| Sample 71 | 27 | 36.189 | 34.03 |
| Sample 72 | 43 | 50.018 | 16.32 |
| Sample 73 | 37 | 40.562 | 9.63 |
| Sample 74 | 72 | 61.767 | −14.21 |
| Sample 75 | 81 | 104.333 | 28.81 |
| Sample 76 | 28 | 28.832 | 2.97 |
| Sample 77 | 42 | 47.134 | 12.22 |
| Sample 78 | 33 | 31.675 | −4.02 |
| Sample 79 | 48 | 55.149 | 14.89 |
| Sample 80 | 15 | 15.629 | 4.19 |
| Sample 81 | 65 | 75.748 | 16.54 |
| Sample 82 | 79 | 89.239 | 12.96 |
| Sample 83 | 35 | 35.169 | 0.48 |
| Sample 84 | 21 | 27.692 | 31.87 |
| Average Bias = | | | 2.22 |

Bias (%) = (Total LC-LC-MS/MS result − RIA result)/RIA result, expressed as a percentage
Samples were selected in sequential order following cross-validation of Estradiol LC-MS/MS to LC-LC-MS/MS to coincide with measurable levels in the Estradiol RIA assay.

Estradiol Inter-assay Comparison of LC-MS/MS to 2D LC-MS/MS

| Sample # | Concentration (pg/mL) LC-MS/MS | LC-LC-MS/MS | Bias (%) |
|---|---|---|---|
| Sample 1 | BLQ | 5.166 | NA |
| Sample 2 | BLQ | 1.754 | NA |
| Sample 3 | BLQ | 6.888 | NA |
| Sample 4 | BLQ | 1.697 | NA |
| Sample 5 | BLQ | 2.488 | NA |
| Sample 6 | ALQ | ALQ | NA |
| Sample 7 | BLQ | 1.911 | NA |
| Sample 8 | BLQ | 8.004 | NA |
| Sample 9 | BLQ | 3.811 | NA |
| Sample 10 | BLQ | 1.115 | NA |
| Sample 11 | BLQ | 3.387 | NA |
| Sample 12 | 14.56 | 13.512 | −7.22 |
| Sample 13 | ALQ | ALQ | NA |
| Sample 14 | 12.06 | 11.612 | −3.73 |
| Sample 15 | 10.04 | 9.950 | −0.86 |
| Sample 16 | 18.56 | 17.069 | −8.01 |
| Sample 17 | 210.69 | 203.458 | −3.43 |
| Sample 18 | BLQ | 3.202 | NA |
| Sample 19 | 21.13 | 21.031 | −0.46 |
| Sample 20 | 11.05 | 10.688 | −3.23 |
| Sample 21 | BLQ | 1.906 | NA |
| Sample 22 | BLQ | BLQ | NA |
| Sample 23 | BLQ | 2.716 | NA |
| Sample 24 | BLQ | BLQ | NA |
| Sample 25 | 143.77 | 149.479 | 3.97 |
| Sample 26 | BLQ | BLQ | NA |
| Sample 27 | BLQ | BLQ | NA |
| Sample 28 | BLQ | BLQ | NA |
| Sample 29 | BLQ | BLQ | NA |
| Sample 30 | BLQ | 6.283 | NA |
| Sample 31 | 10.22 | 8.816 | −13.75 |
| Sample 32 | BLQ | 1.110 | NA |
| Sample 33 | 23.94 | 24.187 | 1.02 |
| Sample 34 | BLQ | 6.641 | NA |
| Sample 35 | BLQ | 8.473 | NA |
| Sample 36 | BLQ | BLQ | NA |
| Sample 37 | BLQ | BLQ | NA |
| Sample 38 | 79.90 | 79.085 | −1.02 |
| Sample 39 | 11.06 | 8.092 | −26.86 |
| Sample 40 | BLQ | BLQ | NA |
| Sample 41 | BLQ | 4.344 | NA |
| Sample 42 | 78.66 | 82.430 | 4.79 |
| Sample 43 | 12.37 | 11.371 | −8.10 |
| Sample 44 | 87.28 | 86.914 | −0.42 |
| Sample 45 | BLQ | 1.043 | NA |
| Sample 46 | 21.21 | 22.228 | 4.80 |
| Sample 47 | 25.18 | 25.616 | 1.74 |
| Sample 48 | 15.81 | 16.038 | 1.43 |
| Sample 49 | BLQ | 4.677 | NA |
| Sample 50 | ALQ | ALQ | NA |
| Average Bias (samples 1–50) = | | | −3.30 |

Bias (%) = (Total LC-LC-MS/MS result − LC-MS/MS result)/LC-MS/MS result, expressed as a percentage
BLQ = Below limit of quantification (10 pg/mL for LC-MS/MS, 1 pg/mL for LC-LC-MS/MS)
ALQ = Above limit of quantification (1000 pg/mL for LC-MS/MS, 500 pg/mL for LC-LC-MS/MS)

Estradiol Cross-Validation of LC-MS/MS to 2D LC-MS/MS Continued

| Sample # | Concentration (pg/mL) LC-MS/MS | LC-LC-MS/MS | Bias (%) |
|---|---|---|---|
| Sample 51 | 187.11 | 181.717 | −2.88 |
| Sample 52 | 91.41 | 89.387 | −2.21 |
| Sample 53 | 47.76 | 45.092 | −5.59 |
| Sample 54 | 53.73 | 50.658 | −5.71 |
| Sample 55 | 14.32 | 12.738 | −11.07 |
| Sample 56 | 26.19 | 30.153 | 15.14 |
| Sample 57 | 34.38 | 33.255 | −3.28 |
| Sample 58 | 27.69 | 25.110 | −9.30 |
| Sample 59 | 41.44 | 44.229 | 6.73 |
| Sample 60 | 27.36 | 27.235 | −0.46 |
| Sample 61 | 260.11 | 248.650 | −4.41 |

-continued

Estradiol Cross-Validation of LC-MS/MS to 2D LC-MS/MS Continued

| Sample # | Concentration (pg/mL) | | Bias (%) |
|---|---|---|---|
| | LC-MS/MS | LC-LC-MS/MS | |
| Sample 62 | 142.53 | 139.889 | −1.85 |
| Sample 63 | 142.95 | 144.874 | 1.34 |
| Sample 64 | 236.23 | 235.982 | −0.11 |
| Sample 65 | ALQ | ALQ | NA |
| Sample 66 | 12.14 | 7.893 | −34.99 |
| Sample 67 | 44.69 | 41.866 | −6.31 |
| Sample 68 | 21.81 | 18.206 | −16.51 |
| Sample 69 | 69.20 | 70.482 | 1.85 |
| Sample 70 | 60.36 | 65.890 | 9.16 |
| Sample 71 | 50.51 | 36.189 | −28.35 |
| Sample 72 | 47.80 | 50.018 | 4.65 |
| Sample 73 | 41.42 | 40.562 | −2.08 |
| Sample 74 | 58.87 | 61.767 | 4.92 |
| Sample 75 | 100.37 | 104.333 | 3.95 |
| Sample 76 | 28.66 | 28.832 | 0.59 |
| Sample 77 | 50.36 | 47.134 | −6.41 |
| Sample 78 | 34.31 | 31.675 | −7.68 |
| Sample 79 | 54.11 | 55.149 | 1.91 |
| Sample 80 | 15.43 | 15.629 | 1.28 |
| Sample 81 | 75.17 | 75.748 | 0.78 |
| Sample 82 | 92.92 | 89.239 | −3.96 |
| Sample 83 | 34.64 | 35.169 | 1.52 |
| Sample 84 | 28.92 | 27.692 | −4.23 |
| Sample 85 | 107.78 | 105.278 | −2.32 |
| Sample 86 | 77.28 | 80.854 | 4.62 |
| Sample 87 | 29.52 | 36.282 | 22.92 |
| Sample 88 | 61.28 | 60.413 | −1.42 |
| Sample 89 | 56.01 | 58.909 | 5.18 |
| Sample 90 | 49.78 | 49.144 | −1.27 |
| Sample 91 | 56.81 | 65.677 | 15.62 |
| Sample 92 | 102.40 | 104.305 | 1.86 |
| Sample 93 | 39.18 | 34.476 | −12.00 |
| Sample 94 | 58.75 | 63.487 | 8.06 |
| Sample 95 | 66.04 | 79.660 | 20.63 |
| Sample 96 | 20.45 | 20.995 | 2.65 |
| Sample 97 | 49.59 | 47.858 | −3.49 |
| Sample 98 | 12.34 | 14.914 | 20.88 |
| Sample 99 | 40.30 | 49.841 | 23.69 |
| Sample 100 | 93.42 | 108.173 | 15.79 |
| Average Bias (samples 51-100) = | | | 0.36 |

Bias (%) = (Total LC-LC-MS/MS result − LC-MS/MS result)/LC-MS/MS result, expressed as a percentage
BLQ = Below limit of quantification (10 pg/mL for LC-MS/MS, 1 pg/mL for LC-LC-MS/MS)
ALQ = Above limit of quantification (1000 pg/mL for LC-MS/MS, 500 pg/mL for LC-LC-MS/MS)

Reference Interval

A. Reference Range Sample Groups and Results

Reference range transfer for estrone, estradiol and total estrogens was evaluated using NCCLS guidance (see references). Transfer of the reference range was established using the samples listed below.

Normal Patient Serum Reference Sample Groups

| | Children[1] | Adult Males | Adult Females | Post-menopausal Females |
|---|---|---|---|---|
| Sample Number | 50 | 25 | 25 | 50 |

[1]Children samples will include 25 boys <10 years old and 25 girls <9 years old.

B. Reference Interval of Patient Test Results

Estrone Reference Ranges

| Reference Population | Reference Range (pg/mL) |
|---|---|
| Adult Female (luteal) | 30-100 pg/mL |
| Adult Female (follicular) | 90-160 pg/mL |
| Adult Male | 10-50 pg/mL |
| Prepubertal Children | <15 pg/mL |
| Post-menopausal Female | <40 pg/mL |

Estradiol Reference Ranges

| Reference Population | Reference Range (pg/mL) |
|---|---|
| Adult Female | 30-100 pg/mL |
| Adult Female (follicular) | 70-300 pg/mL |
| Adult Male | 8-35 pg/mL |
| Prepubertal Children | <15 pg/mL |
| Post-menopausal Female | <15 pg/mL |

C. Reference Range Transfer

Guidance provided by NCCLS allows reference range transfer where no more than 2 out of 20 (10%) of samples fall outside the original reference range. A total of 22 out of 23 normal adult female samples were within range for reference range transfer of estrone, estradiol and total estrogens. Adult female reference ranges are transferable. All normal adult male samples were within range for reference range transfer of estrone and estradiol. A total of 22 out of 23 normal adult male samples were within range for reference range transfer of total estrogens. Adult male reference ranges are transferable. All 50 pre-pubertal reference samples were within range for reference range transfer for estrone, estradiol and total estrogens. Pre-pubertal reference ranges are transferable. A total of 24 out of 25 normal post-menopausal female samples were within range for reference range transfer of estrone and total estrogens. A total of 23 out of 25 normal post-menopausal female samples were within range for reference range transfer of estradiol. Post-menopausal female reference ranges are transferable.

Estrone and Estradiol Adult Reference Range Verification

| Adults | Concentration (pg/mL) | | | Adults | Concentration (pg/mL) | | |
|---|---|---|---|---|---|---|---|
| | Estrone | Estradiol | Total | | Estrone | Estradiol | Total |
| Female 1 | 70.883 | 95.809 | 166.692 | Male 1 | 30.575 | 21.764 | 52.339 |
| Female 2 | 76.600 | 127.096 | 203.696 | Male 2 | 28.002 | 20.025 | 48.027 |
| Female 3* | 13306.414 | 14156.104 | 27462.518 | Male 3 | 32.190 | 22.324 | 54.514 |
| Female 4 | 66.318 | 60.373 | 126.691 | Male 4 | 28.509 | 31.160 | 59.669 |
| Female 5 | 65.789 | 132.145 | 197.934 | Male 5 | 29.666 | 19.525 | 49.191 |
| Female 6 | 95.624 | 109.358 | 204.982 | Male 6 | 40.293 | 18.999 | 59.292 |
| Female 7 | 81.402 | 114.658 | 196.060 | Male 7 | 20.721 | 16.842 | 37.563 |
| Female 8 | 45.846 | 33.105 | 78.951 | Male 8 | 46.467 | 19.506 | 65.973 |

Estrone and Estradiol Adult Reference Range Verification

| Adults | Concentration (pg/mL) | | | Adults | Concentration (pg/mL) | | |
|---|---|---|---|---|---|---|---|
| | Estrone | Estradiol | Total | | Estrone | Estradiol | Total |
| Female 9 | 37.735 | 39.985 | 77.720 | Male 9* | 77.912 | 48.095 | 126.007 |
| Female 10 | 30.071 | 38.714 | 68.785 | Male 10 | 24.086 | 20.251 | 44.337 |
| Female 11 | 58.483 | 65.622 | 124.105 | Male 11 | 30.402 | 14.473 | 44.875 |
| Female 12 | 119.945 | 345.081 | 465.026 | Male 12 | 40.782 | 23.593 | 64.375 |
| Female 13 | 112.298 | 246.219 | 358.517 | Male 13 | 48.644 | 34.843 | 83.487 |
| Female 14 | 103.689 | 51.824 | 155.513 | Male 14 | 29.029 | 19.883 | 48.912 |
| Female 15 | 86.195 | 109.157 | 195.352 | Male 15 | 38.322 | 34.511 | 72.833 |
| Female 16 | 43.546 | 30.348 | 73.894 | Male 16 | 26.460 | 34.060 | 60.520 |
| Female 17 | 83.344 | 96.485 | 179.829 | Male 17 | 38.597 | 28.584 | 67.181 |
| Female 18 | 31.321 | 31.050 | 62.371 | Male 18* | 71.676 | 55.531 | 127.207 |
| Female 19 | 64.664 | 158.151 | 222.815 | Male 19 | 49.944 | 26.688 | 76.632 |
| Female 20 | 48.442 | 30.094 | 78.536 | Male 20 | 37.529 | 24.837 | 62.366 |
| Female 21 | 45.145 | 30.001 | 75.146 | Male 21 | 33.808 | 19.570 | 53.378 |
| Female 22* | 46.019 | 11.005 | 57.024 | Male 22 | 33.282 | 25.675 | 58.957 |
| Female 23 | 26.042 | 35.425 | 61.467 | Male 23 | 18.813 | 14.025 | 32.838 |
| Female 24 | 52.566 | 64.966 | 117.532 | Male 24 | 26.792 | 17.124 | 43.916 |
| Female 25 | 44.511 | 142.452 | 186.963 | Male 25 | 30.602 | 33.692 | 64.294 |

*= Abnormal results using alternate assay, excluded from reference range calculations.
Estrone Female reference range = 30-100 pg/mL (luteal), 90-160 pg/mL (follicular)
Estrone Male reference range = 10-50 pg/mL.
Estradiol Female reference range = 30-100 pg/mL (luteal), 70-300 pg/mL (follicular)
Estrone Male reference range = 8-35 pg/mL
Total Estrogens Female reference range = 60-200 pg/mL (luteal), 160-400 pg/mL (follicular)
Total Estrogens Male reference range = 20-80 pg/mL

Estrone and Estradiol Prepubertal Reference Range Verification

| Children | Concentration (pg/mL) | | | Children | Concentration (pg/mL) | | |
|---|---|---|---|---|---|---|---|
| | Estrone | Estradiol | Total | | Estrone | Estradiol | Total |
| Female 1 | BLQ | BLQ | BLQ | Male 1 | BLQ | BLQ | BLQ |
| Female 2 | BLQ | BLQ | BLQ | Male 2 | BLQ | BLQ | BLQ |
| Female 3 | BLQ | BLQ | BLQ | Male 3 | BLQ | BLQ | BLQ |
| Female 4 | BLQ | BLQ | BLQ | Male 4 | BLQ | BLQ | BLQ |
| Female 5 | BLQ | 1.052 | 1.052 | Male 5 | BLQ | BLQ | BLQ |
| Female 6 | BLQ | BLQ | BLQ | Male 6 | BLQ | BLQ | BLQ |
| Female 7 | BLQ | BLQ | BLQ | Male 7 | BLQ | BLQ | BLQ |
| Female 8 | BLQ | BLQ | BLQ | Male 8 | BLQ | BLQ | BLQ |
| Female 9 | BLQ | BLQ | BLQ | Male 9 | BLQ | BLQ | BLQ |
| Female 10 | BLQ | BLQ | BLQ | Male 10 | BLQ | BLQ | BLQ |
| Female 11 | BLQ | BLQ | BLQ | Male 11 | BLQ | BLQ | BLQ |
| Female 12 | BLQ | BLQ | BLQ | Male 12 | BLQ | BLQ | BLQ |
| Female 13 | BLQ | BLQ | BLQ | Male 13 | BLQ | BLQ | BLQ |
| Female 14 | BLQ | BLQ | BLQ | Male 14 | BLQ | BLQ | BLQ |
| Female 15 | BLQ | 1.718 | 1.718 | Male 15 | BLQ | BLQ | BLQ |
| Female 16 | BLQ | BLQ | BLQ | Male 16 | BLQ | BLQ | BLQ |
| Female 17 | BLQ | BLQ | BLQ | Male 17 | 2.577 | BLQ | 2.577 |
| Female 18 | BLQ | BLQ | BLQ | Male 18 | BLQ | BLQ | BLQ |
| Female 19 | BLQ | BLQ | BLQ | Male 19 | BLQ | BLQ | BLQ |
| Female 20 | BLQ | BLQ | BLQ | Male 20 | BLQ | BLQ | BLQ |
| Female 21 | BLQ | BLQ | BLQ | Male 21 | BLQ | BLQ | BLQ |
| Female 22 | BLQ | BLQ | BLQ | Male 22 | BLQ | BLQ | BLQ |
| Female 23 | BLQ | BLQ | BLQ | Male 23 | BLQ | BLQ | BLQ |
| Female 24 | BLQ | BLQ | BLQ | Male 24 | BLQ | BLQ | BLQ |
| Female 25 | BLQ | BLQ | BLQ | Male 25 | BLQ | BLQ | BLQ |

Estrone Pre-pubertal reference range = <15 pg/mL
Estradiol Pre-pubertal reference range = <15 pg/mL
Total Estrogens Pre-pubertal reference range = <25 pg/mL

Estrone and Estradiol Post-menopausal Reference Range Verification

| Post Menopausal | Concentration (pg/mL) | | |
|---|---|---|---|
| | Estrone | Estradiol | Total Estrogens |
| Post Menopausal Female 1 | 15.512 | 6.174 | 21.686 |
| Post Menopausal Female 2 | 26.081 | 14.535 | 40.616 |
| Post Menopausal Female 3 | 17.392 | 5.680 | 23.072 |
| Post Menopausal Female 4 | 11.037 | 4.297 | 15.334 |
| Post Menopausal Female 5 | 26.321 | 12.717 | 39.038 |
| Post Menopausal Female 6 | 22.282 | 4.653 | 26.935 |
| Post Menopausal Female 7 | 10.769 | 5.123 | 15.892 |
| Post Menopausal Female 8 | 34.193 | 14.398 | 48.591 |
| Post Menopausal Female 9 | 8.257 | 4.016 | 12.273 |
| Post Menopausal Female 10 | 25.306 | 11.681 | 36.987 |
| Post Menopausal Female 11 | 22.873 | 10.268 | 33.141 |
| Post Menopausal Female 12 | 7.838 | 14.060 | 21.898 |
| Post Menopausal Female 13 | 12.848 | 3.788 | 16.636 |
| Post Menopausal Female 14 | 8.348 | 21.916 | 30.264 |
| Post Menopausal Female 15 | 8.502 | 3.173 | 11.675 |
| Post Menopausal Female 16 | 17.502 | 11.371 | 28.873 |
| Post Menopausal Female 17 | 9.837 | 5.903 | 15.740 |
| Post Menopausal Female 18 | 34.756 | 14.946 | 49.702 |
| Post Menopausal Female 19 | 24.933 | 6.502 | 31.435 |
| Post Menopausal Female 20 | 10.280 | 6.123 | 16.403 |
| Post Menopausal Female 21 | 30.275 | 19.200 | 49.475 |
| Post Menopausal Female 22 | 15.434 | 4.680 | 20.114 |
| Post Menopausal Female 23 | 8.889 | 9.670 | 18.559 |
| Post Menopausal Female 24 | 7.437 | 5.139 | 12.576 |
| Post Menopausal Female 25 | 44.117 | 14.607 | 58.724 |

Estrone Post-menopausal female reference range = <40 pg/mL
Estradiol Post-menopausal female reference range = <15 pg/mL
Total Estrogens Post-menopausal female reference range = <50 pg/mL Standard Curve Fitting and Reproducibility The reproducibility of the standard curve was evaluated by comparing the back-calculated concentrations to the theoretical concentration of the standard in five analytical runs using the concentrations listed below. Calibrator Concentrations for estrone and estradiol (pg/mL) were as follows: 1; 2.5; 5; 10; 25; 50; 100; 200; 350; and 500.

The reproducibility of the standard curve was evaluated by comparing the back-calculated concentrations to the actual concentration of the standard in five analytical runs. The curve was fit with a straight line with weighted 1/x fit, as established during method development. Acceptability Criteria: Imprecision of ≦20% at the LLOQ and less than ≦15% at other concentrations. Correlation coefficient (r) greater than 0.98. It was found that estrone calibration curves exhibited mean imprecision <15% for all concentrations between 2.5 pg/mL and 500 pg/mL. Correlation coefficients were greater than 0.98. Estradiol calibration curves exhibited mean imprecision <15% for all concentrations between 1.0 pg/mL and 500 pg/mL. Correlation coefficients were greater than 0.98.

Analytical Reportable Range
A. LLOQ (Lower Limit of Quantification)

The lower limit of quantification for estrone using this assay was 2.5 pg/mL as determined during evaluation of inaccuracy, imprecision and calibration curve reproducibility. The lower limit of quantification for estradiol using this assay was 1.0 pg/mL as determined during evaluation of inaccuracy, imprecision and calibration curve reproducibility.

B. ULOQ (Upper Limit of Quantification)

The upper limit of quantification using this assay was 500 pg/mL for both estrone and estradiol, as determined during evaluation of inaccuracy, imprecision and calibration curve reproducibility.

| | Estrone Standard Curve Fitting and Reproducibility | | | | | | | | | |
|---|---|---|---|---|---|---|---|---|---|---|
| | Std 1 | Std 2 | Std 3 | Std 4 | Std 5 | Std 6 | Std 7 | Std 8 | Std 9 | Std 10 |
| | Actual Concentration (pg/mL) | | | | | | | | | |
| Batch | 1.000 | 2.500 | 5.000 | 10.000 | 25.000 | 50.000 | 100.000 | 200.000 | 350.000 | 500.000 |
| 1 | 1.925 | 2.768 | 5.648 | 9.711 | 23.467 | 46.373 | 94.259 | 185.715 | 349.442 | 469.565 |
| | 1.390 | 2.754 | 4.873 | 11.121 | 23.507 | 47.062 | 92.564 | 191.601 | 366.589 | 557.980 |
| 2 | 0.461 | 2.173 | 4.906 | 9.681 | 24.933 | 52.284 | 97.879 | 208.321 | 373.433 | 466.693 |
| | 1.511 | 2.321 | 5.407 | 10.333 | 24.749 | 52.497 | 103.488 | 200.953 | 355.922 | 489.025 |
| 3 | 0.886 | 2.613 | 4.448 | 10.294 | 25.019 | 50.470 | 97.538 | 203.637 | 352.701 | 495.023 |
| | 1.897 | 2.896 | 4.602 | 9.475 | 24.639 | 50.202 | 99.235 | 209.807 | 340.983 | 501.419 |
| 4 | 0.110 | 2.514 | 5.357 | 9.913 | 24.999 | 50.807 | 100.802 | 202.390 | 354.388 | 473.363 |
| | 1.146 | 2.371 | 5.183 | 9.199 | 24.605 | 48.966 | 101.284 | 204.313 | 354.972 | 509.573 |
| 5 | IE | 2.728 | 5.174 | 9.417 | 23.121 | 46.892 | 98.169 | 188.782 | 344.288 | 500.983 |
| | 1.204 | 2.372 | 5.230 | 10.185 | 24.417 | 54.467 | 102.299 | 203.899 | 363.129 | 499.448 |
| Mean | 1.170 | 2.551 | 5.083 | 9.933 | 24.346 | 50.002 | 98.752 | 199.942 | 355.585 | 496.307 |
| Accuracy (% RE) | 17.00 | 2.04 | 1.66 | −0.67 | −2.62 | 0.00 | −1.25 | −0.03 | 1.60 | −0.74 |
| Precision (% RSD) | 52.09 | 9.28 | 7.33 | 5.71 | 2.91 | 5.37 | 3.49 | 4.15 | 2.79 | 5.29 |
| n | 9 | 10 | 10 | 10 | 10 | 10 | 10 | 10 | 10 | 10 |

IE = Injection error

| Estrone Standard Curve Fitting and Reproducibility Continued | | | |
|---|---|---|---|
| Batch | $K_0$ (Y-intercept) | $K_1$ (slope) | Correlation Coefficient (R) |
| 1 | 0.0071 | 0.0148 | 0.9973 |
| 2 | 0.0227 | 0.0126 | 0.9989 |
| 3 | 0.0168 | 0.0134 | 0.9998 |
| 4 | 0.0210 | 0.0135 | 0.9996 |
| 5 | 0.0153 | 0.0136 | 0.9995 |
| Mean | 0.0166 | 0.0136 | 0.9990 |
| Precision (% RSD) | NA | 5.81 | 0.10 |
| n | 5 | 5 | 5 |

| | Estradiol Standard Curve Fitting and Reproducibility | | | | | | | | | |
|---|---|---|---|---|---|---|---|---|---|---|
| | Std 1 | Std 2 | Std 3 | Std 4 | Std 5 | Std 6 | Std 7 | Std 8 | Std 9 | Std 10 |
| | Actual Concentration (pg/mL) | | | | | | | | | |
| Batch | 1.000 | 2.500 | 5.000 | 10.000 | 25.000 | 50.000 | 100.000 | 200.000 | 350.000 | 500.000 |
| 1 | 0.957 | 2.550 | 5.264 | 10.062 | 24.338 | 48.037 | 96.655 | 208.854 | 349.140 | 495.339 |
| | 0.939 | 2.590 | 4.946 | 10.258 | 26.356 | 48.204 | 100.102 | 202.014 | 362.357 | 488.038 |
| 2 | 0.948 | 2.281 | 5.005 | 10.065 | 26.660 | 51.180 | 100.076 | 203.386 | 361.785 | 493.088 |
| | 0.838 | 2.168 | 5.524 | 10.089 | 25.499 | 51.815 | 110.920 | 228.732 | 329.844 | 467.097 |
| 3 | 0.998 | 2.550 | 5.306 | 10.203 | 23.766 | 51.117 | 100.742 | 206.641 | 341.105 | 516.785 |
| | 0.951 | 2.500 | 5.171 | 9.725 | 24.066 | 50.488 | 98.928 | 195.879 | 349.439 | 490.639 |
| 4 | 1.083 | 2.494 | 5.032 | 9.294 | 22.005 | 44.878 | 95.496 | 190.745 | 348.234 | 477.884 |
| | 1.073 | 2.463 | 5.346 | 9.807 | 25.939 | 51.655 | 105.187 | 208.906 | 365.338 | 514.143 |
| 5 | IE | 2.685 | 4.853 | 9.247 | 25.130 | 47.971 | 97.174 | 196.876 | 349.441 | 500.232 |

Estradiol Standard Curve Fitting and Reproducibility

| | Std 1 | Std 2 | Std 3 | Std 4 | Std 5 | Std 6 | Std 7 | Std 8 | Std 9 | Std 10 |
|---|---|---|---|---|---|---|---|---|---|---|
| | | | | | Actual Concentration (pg/mL) | | | | | |
| Batch | 1.000 | 2.500 | 5.000 | 10.000 | 25.000 | 50.000 | 100.000 | 200.000 | 350.000 | 500.000 |
| | 0.995 | 2.517 | 5.178 | 9.999 | 25.929 | 49.433 | 102.279 | 203.003 | 355.375 | 497.684 |
| Mean | 0.976 | 2.480 | 5.163 | 9.875 | 24.969 | 49.478 | 100.756 | 204.504 | 351.206 | 494.093 |
| Accuracy (% RE) | −2.42 | −0.81 | 3.25 | −1.25 | −0.12 | −1.04 | 0.76 | 2.25 | 0.34 | −1.18 |
| Precision (% RSD) | 7.59 | 6.06 | 3.98 | 3.61 | 5.73 | 4.47 | 4.52 | 5.05 | 3.05 | 3.02 |
| n | 9 | 10 | 10 | 10 | 10 | 10 | 10 | 10 | 10 | 10 |

IE = Injection error

Estradiol Standard Curve Fitting and Reproducibility Continued

| Batch | $K_0$ (Y-intercept) | $K_1$ (slope) | Correlation Coefficient (R) |
|---|---|---|---|
| 1 | 0.0069 | 0.0234 | 0.9997 |
| 2 | 0.0167 | 0.0217 | 0.9980 |
| 3 | 0.0058 | 0.0229 | 0.9997 |
| 4 | 0.0035 | 0.0223 | 0.9991 |
| 5 | 0.0014 | 0.0226 | 0.9999 |
| Mean | 0.0088 | 0.0226 | 0.9990 |
| Precision (% RSD) | NA | 2.83 | 0.08 |
| n | 5 | 5 | 5 |

Example 2

96-Well Equilibrium Dialysis Followed by Isotope Dilution LC-MS/MS for Free Thyroxine Development and validation of free thyroxine (FT4) was developed using a high throughput 96-well based equilibrium dialysis techniques to provide a generational improvement in assay performance over historical radioimmunoassays. Equilibrium dialysis of free thyroxine was chosen over ultrafiltration during method development. Significant variance between ultrafiltration and equilibrium dialysis with RIA detection was observed at 37° C. Further, filtrate yield (and analytical sensitivity) was limited for sample types containing significant lipemic content, resulting in blockage of the filtration membrane. Optimization of dialysis parameters (rotator speed, dialysate buffer composition and dialysis time) was undertaken using pooled normal calibrators, controls of known free thyroxine concentration and spiked dialysis buffer (50% yield of original result when completely dialysed). Dialysis losses were evaluated using spiked dialysis buffer. Referring now to FIG. 31, the measured concentration of free thyroxine versus dialysis time is shown.

Free thyroxine (FT4) was measured by liquid chromatography with tandem mass spectrometry detection (LC-MS/MS) after 96-well plate based equilibrium dialysis and either sample dilution or liquid-liquid extraction (ED-LLE). Thyroxine Ring-$^6C_{13}$ is added as internal standard to post dialysis aliquots. For liquid liquid extraction protocols, free thyroxine was extracted from dialysate and calibrator samples with 71.25:23.75:5 Ethyl Acetate:Hexane: Methanol. The organic extract was transferred to a fresh tube and then evaporated and reconstituted in 50:50 Water:Methanol. For the sample dilution preparative protocols, dialysate duffer without gelatin was prepared and only internal standard solution in methanol was added, prior to LC-MS/MS analysis.

Duplicate sets of FT4 calibrators were analyzed in each batch. All injections were made in singlicate. All samples were injected onto the ARIA TX4 or Transcend TX4 system where the analyte of interest was chromatographed through an analytical column via a gradient separation. An MDS-SCIEX API5000 triple quadrupole mass spectrometer, operating in negative ion electrospray ionization (ESI) mode (Turboionspray) was used for detection.

Quantification of analyte and internal standard was performed in selected reaction monitoring mode (SRM). The back-calculated amount of each analyte in each sample was determined from duplicate calibration curves generated by spiking known amounts of purified thyroxine into dialysis buffer or methanol:water solutions.

Measurement of free thyroxine is used to evaluate hyperthyroidism and hypothyroidism, to differentiate and evaluate disorders involving variance in levels of circulating proteins, such as, familial dysalbuminemic hyperthyroximenia, euthyroid hypothyroxemias, transthyretin excess and variant thyroxine binding globulin. Analysis of free thyroxine by ED-LLE-LC-MS/MS or ED-LC-MS/MS detection was developed to measure levels in serum samples from children, women and men. The lower limit of detection using the default sample aliquot of 200 µL is 0.2 ng/dL (2 pg/mL) for free thyroxine.

Definitions

T4—Thryroxine, ED—Equilibrium Dialysis, LC-MS/MS—Liquid Chromatography tandem mass spectrometry detection, ESI− Electrospray Ionization (Turboionspray), L-Thyroxine, Sigma-Aldrich, (USA) Product # T2376 or USP, (USA) Product #044K1436; Stable Labeled Thyroxine, Tyrosine Ring-$^{13}C_6$, CDN Isotopes, (USA) Product # CLM-6725-O.

Specimen Requirements

Recommended: 0.5 mL serum or plasma. Separate within one hour. Store and ship frozen in a plastic vial.

| Adult: | 0.5 mL serum preferred or plasma |
|---|---|
| Pediatric: | 0.5 mL serum preferred or plasma |
| Minimum: | 0.5 mL serum preferred or plasma |

Blood was drawn into red top vacutainer tube and clotting allowed to occur for 20 minutes at room temperature (or until clot had retracted). The sample was then centrifuged and the serum transferred to a labeled plastic vial, and immediately frozen. Storage is short term storage (2 weeks); frozen ($\leq$−20° C.). Shipping is Frozen ($\leq$−20° C.)—on dry ice.

Equipment & Materials

The following materials were used: Standard manual pipetting devices; Big Shot II Hybridization Oven (Rotator, Boekel Scientific Model No. 230401); 96-Well Equilibrium 10 kD Dialyzer Plates (Harvard Apparatus, Product No. 74-2331); 1.2 ml MBlock Polypropylene 96 Well Collection Plate (SPE Ware, Inc. Product No. SPE0210); Heat Sealing Foil (SPE Ware, Inc. Product No. AB-0589); Mechanical Shaker, Eberbach Inc.; Rotary Evaporator (rotovap), Speed Vac SC 200, Savant; Volumetric Glass Bottles for mobile phases, various sizes; API 5000 Tandem Mass Spectrometer, Sciex, (Toronto, Canada); Turbo V™ Ion source with ESI probe, Sciex, (Toronto, Canada); Aria TX4 HTLC System, Cohesive Technologies, (MA, USA) consisting of 4 each: 1100 Series Quaternary Pump, 1100 Series Binary Pump, 1100 Series Vacuum Degasser; HTS Twin PAL System Autosampler, CTC Analytics AG (Switzerland); BETASIL Phenyl-Hexyl Analytical Column, 50×2.1 mm, 5 µm particle size, Thermo Electron Corporation, (USA) Product No. 73005-052130; Vortex Mixer, VWR or equivalent; Combithermo Heat Sealer, Abgene Inc., Product No. AB-0559; 96-Well Centrifuge 5804R Eppendorf or equivalent; Solvent washed 12×75 mm borosilicate glass tubes with polypropylene snap caps; Analyst Version 1.4 or greater. Applied Biosystems, (CA, USA); Aria OS Version 1.4 or greater, Cohesive Technologies (MA, USA).

Reagents

Water—Type II, Millipore MilliQ or equivalent; Water—Glass Distilled; Acetonitrile HPLC Grade (EM Science, Catalog#AX0142-1); Methanol HPLC Grade (Fisher Scientific, Catalog#A452-4); Hexane HPLC Grade (Fisher Scientific, Catalog #H302-4); Ethyl Acetate OPTIMA Grade (Fisher Scientific, Catalog #E196-4); Ammonium Hydroxide 28.0-30.0% (JT Baker, Catalog#9721-04); Formic Acid 88% (Fisher Scientific, Catalog#A118-500); 1 mg/mL stock L-Thyroxine (Sigma, Catalog#T2376) (Dissolve appropriate amount of L-Thyroxine powder into the appropriate volume of 25% Ammonium Hydroxide in Methanol); Blue Dextran Dye Marker (18/mg/mL) in millipore water. Ammonium Carbonate (100 mM) in millipore water. Extraction solvent for liquid-liquid extraction (71.25% Ethyl Acetate, 23.75% Hexane, and 5% Methanol).

1 mg/mL stock Tyrosine Ring-$^{13}C_6$ (Cambridge Isotope Labs, Catalog#CLM-6725-O) Dissolve appropriate amount of Tyrosine Ring-$^{13}C_6$ powder into the appropriate volume of 25% Ammonium Hydroxide in Methanol).

The following protocol was used to prepare FT4 Dialysis Buffer (with and without gelatin). Mix 800 mL of Millipore Water or equivalent, add 1 mL Sodium DL-Lactate 60% (w/w) (Sigma-Aldrich, Catalog#L1375), 5.265 g Sodium Chloride (EMD Science, Catalog#SX0420-1), 0.224 g Potassium Chloride (EMD Science, Catalog#PX1450-1), 0.180 g Potassium Phosphate (EMD Science, Catalog#PX1565-1), 0.246 g Magnesium Sulfate $7H_2O$ (Sigma-Aldrich, Catalog#M1880), 0.300 g Urea (Sigma-Aldrich, Catalog#U0631). Dissolved 0.275 g of Calcium Chloride (EMD Science, Catalog#SX0130-1) into 5 mL of Millipore Water in a separate glass vial and added to the above solution. Next (Step A) is performed: The buffer solution was heated to 50° C. and while mixing, slowly added 1.0 g Laboratory Grade Gelatin Type A (Fisher, Catalog#G8-500). The buffer solution was then allowed to. Step B: added 5.891 g HEPES Sodium Salt (Sigma-Aldrich, Catalog#H7006). In a separate glass bottle dissolved 7.190 g of HEPES Acid (Sigma-Aldrich, Catalog#H3375) into 200 mL of Millipore Water. Added this to above solution slowly until the pH reached 7.4 and QS to 1000 mL with Millipore Water. The buffer is then aliquoted into glass vials and stored frozen at −20° C. for up to 3 months. To prepare FT4 Dialysis Buffer without gelatin, the buffer is prepared as above except excluding step A.

To prepare internal standard diluent 1, two Liters Millipore Water or equivalent are mixed with 0.200 g Calcium Chloride (EMD Science, Catalog#SX0130-1), 16.37 g Sodium Chloride (EMD Science, Catalog#SX0420-1), 2.0 g Sodium Azide (Sigma-Aldrich, Catalog#S8032), 4.30 g Sodium Phosphate Dibasic (EMD Science, Catalog#SX0715), 0.380 g Sodium Phosphate Monobasic (J. T. Baker, Catalog#3818-0), 26 mL 10% BSA (Sigma-Aldrich, Catalog# A3803). The lot is tested to ensure minimal analyte response from buffer and stored refrigerated at 4° C. for up to 6 months. The internal standard diluent 2 is methanol.

To prepare an internal standard solution for liquid-liquid extraction (100 pg/mL $^{13}C_6$-Thyroxine) added 0.1 mL of 100 ng/ml $^{13}C_6$-Thyroxine to 100 mL internal standard diluent 1, and mixed well. The standard was then aliquoted into 20 mL glass scintillation vials. To prepare an internal standard solution for diluting and inject (100 pg/mL $^{13}C_6$-Thyroxine), added 0.1 mL of 100 ng/ml $^{13}C_6$-Thyroxine to 100 mL methanol.

The FT4 Reconstitution Solution was 50:50 Millipore Water: Methanol. The following mobile phases were used: Eluting Pump A Mobile Phase (90% Water and 10% Methanol); Eluting Pump B Mobile Phase (90% Methanol and 10% Water); Loading Pump A Mobile Phase for post-column addition (90% Methanol and 10% Water with 1 mM Ammonium Carbonate).

Two needle wash solutions were used: Needle Wash Solution 1 (Aqueous 1% Formic Acid), Needle Wash Solution 2 (70:30 Acetonitrile: 1N Ammonium Hydroxide). The needle wash solutions were stored at room temperature for up to 6 months.

Calibration Procedures with Liquid-Liquid Extraction

Duplicate standard curves, as described in this procedure, are included with each analytical batch. An L-Thyroxine Stock Solution (100 ng/mL)-100 ng/ml L-Thyroxine stock, made by serially diluting the 1 mg/mL L-Thyroxine stock in methanol, is used to prepare intermediate stock solutions for preparation of calibrators. Dilute 1.0 mL of L-Throxine Stock (100 ng/mL) to 100 mL with FT4 Dialysis Buffer to yield 1 ng/mL thyroxine solution. This stock is stable when stored at −70° C. Next, dilute 10 mL of the 1 ng/mL solution to 100 mL in FT4 Dialysis Buffer to yield a 100 pg/mL free thyroxine solution. Stable when stored at −70° C. Using these stock solutions, calibration standards of 0.2, 0.5, 1.0, 2.5, 5.0, and 10 ng/dL were made. All standards were prepared in FT4 Dialysis Buffer with or without gelatin if performing liquid-liquid extraction. The calibration standards were then transferred into appropriately labeled glass vials in 1 mL aliquots, capped and stored frozen at −20° C.

Calibration Procedures With Sample Dilution

Duplicate standard curves, as described in this procedure, are included with each analytical batch. An L-Thyroxine Stock Solution (100 ng/mL)-100 ng/ml L-Thyroxine stock, made by serially diluting the 1 mg/mL L-Thyroxine stock in methanol, was used to prepare intermediate stock solutions for preparation of calibrators. To make the intermediate stock solutions, diluted 1.0 mL of L-Throxine Stock (100 ng/mL) to 100 mL with methanol to yield 1 ng/mL thyroxine solution. This stock is stable when stored at −70° C. Next, diluted 10 mL of the 1 ng/mL solution to 100 mL in methanol to yield a 100 pg/mL thyroxine solution. This stock is also stable when stored at −70° C. Using these stock solutions, calibration standards of 0.2, 0.5, 1.0, 2.5, 5.0, and 10 ng/dL were made. All standards were prepared in 1:1 methanol:water. The calibration standards were transferred into appropriately labeled glass vials in 1 mL aliquots, capped and stored frozen at −20° C.

Quality Control

Control pools are prepared in human serum as shown below and introduced into use according to analytically robust procedures

| Quality Control Concentrations | |
|---|---|
| Control Name | Target concentration (ng/dL) Free Thyroxine |
| QC 1 | 1.0 |
| QC 2 | 1.5 |
| QC 3 | 2.5 |
| QC 4 | 8.0 |

The control data was recorded for each run on Levy-Jennings charts. Points were plotted and connected. The control chart is reviewed for shifts or trends. A warning situation may exists if one control falls within the ±2 SD and ±3 SD interval; all test results may be released.

Test Procedure

A. Assay Procedure

Dialysis of samples: Dialysis was performed as follows. Warmed the Big Shot II hybridization oven to reach 37° C. Capped sample side (blue side) of the dialysis plate. Turned the plate over and added 300 µL of FT4 Dialysis Buffer either with or without gelatin using an Eppendorf Plus repeating pipette, or equivalent, with a 10 mL tip to the buffer side (clear side) of the dialysis plate. Added the buffer gently to stop bubble formation. Capped the buffer side. Turned the plate over and uncapped the sample side of the dialysis plate. Pipetted 10 µl of 18 mg/mL blue dextran dye marker solution into each well. Pipette controls and patient samples (0.2 mL) into the wells with an Eppendorf pipette (or equivalent). Added the patient and QC samples gently to stop bubble formation. Recapped the sample side of the dialysis plate, and place the dialysis plate into the oven and turn on the rotator with the speed set at 15 RPM. Let rotate overnight for 16 hours±1 hour.

After the dialysis procedure was complete, thawed and mix the internal standard solution to add to the samples for liquid-liquid extraction. Labeled a solvent washed 12×75 glass tube for each dialysis sample, duplicate tubes for each standard point, and four tubes for the double blanks. After dialysis was complete checked for any trace of blue dextran in the buffer side (clear side) of the plate. Note dany membrane leakage and did not transfer the dialysate from the wells with faulty membranes. Pipetted 200 µL of dialysate from the buffer side (clear side) of the dialysis plate for each sample into the corresponding 12×75 glass tube. Pipetted 200 µL of standard into the appropriate labeled tubes. Pipetted 200 µL of FT4 Dialysis Buffer into the double blanks.

Liquid-liquid Extraction Procedure: Liquid-liquid extraction was done as follows. 50 µL of 100 pg/mL FT4 Internal Standard 1 was added to all tubes, except the double blanks to which 50 µL of water was added. Tubes were mixed 10 times up and down (e.g., on a multi-tube vortexer) and let stand for 10 minutes.

For extraction, 2 mL of extraction solvent was added to all tubes. Tubes were capped and mixed on a multi-tube vortexer, 4 times for 1 minute intervals. The tubes were removed from the shaker and spun down in centrifuge at 3000 rpm for 10 minutes. A separate set of 12×75 solvent (methanol) washed glass tubes was labeled, and after freezing the aqueous layer, the extract was poured into the labeled tubes. The tubes were placed in a Rotovap to allow solvent to evaporate for at least 45 minutes.

Once there was no trace of solvent left in the tubes, the samples were reconstituted with 100 µL reconstitution solution. Tubes were then covered with parafilm and mixed on multivortexer, 4 times for 30 second intervals. Using an Eppendorf pipette, a robotic liquid handler, or equivalent, the reconstituted sample was transferred from the 12×75 tubes into a 96-well plate. A heat-sealing foil was placed over the plate and the plate sealed with a heated plate sealer. The sealed plate was then centrifuged at 3700 rpm (approximately 2000 g) at 10° C. for 10 minutes. 80 µL was used for injection.

Dilute and Inject Procedure: For injection, 50 µL of 100 pg/mL FT4 Internal Standard solution 2 (methanol) was added to all tubes, except the double blanks to which 50 µL of water was added. Tubes were mixed (e.g. 10 times up and down on a multi-tube vortexer) and allowed to stand for 10 minutes. Place a heat-sealing foil over the plate and seal the plate with the heated plate sealer. Centrifuge plate at 3700 rpm (approximately 2000 g) at 10° C. for 10 minutes. Inject 100 µL.

LC-MS/MS Procedures: For LC-MSIMS, the 96-well plate is placed in LC-MS/MS Autosampler and the system filled with LC system reagents. After liquid-liquid extraction or sample dilution, 80 to 100 µL of processed sample was injected into the HTLC system using methanol:water in the mobile phase. The HTLC system comprises two HPLC pumps per channel that can be employed in two functions: (1) Post HPLC-column addition of solvents to improve sensitivity; and (2) HPLC chromatography using a binary gradient and a 5 µm reverse phase analytical column. In this example a phenyl hexyl column was used for chromatography, which had a 5-µm particle size. Such HPLC columns are commercially available (e.g., Thermo Hypersil Phenyl Hexyl, Luna Phenyl Hexyl). In the analytical mode of the HTLC, the sample was first loaded onto the analytical column. A binary gradient of from 40% to 90% methanol at 1 mL per minute over 2 minutes was used, resulting in the separation of thyroxine and internal standard from matrix interferences and other analytes contained in the sample. Ionization efficiency and thus detection limits were enhanced by post-column addition of a 90:10 Methanol:water solution containing 1 mM ammonium carbonate at 200 microliters per minute. The separated sample was then transferred to the MS/MS for quantitation. The LC method is summarized in the table below. Thyroxine and internal standard elute at approximately 2.5 minutes from the start of the method (+ or −0.5 minutes)

| Free Thyroxine LC Method | | | | | | |
|---|---|---|---|---|---|---|
| STEP | Start Time (minutes) | Step Duration (seconds) | Post-column Loading pump Flow Rate (mL/minute) | Eluting Pump* (% B) | Flow Rate (mL/minute) | Eluting Pump Gradient Type |
| 1 | 0.00 | 40 | 0.2 | 40 | 1.0 | Isocratic |
| 2 | 0.67 | 120 | 0.2 | 100 | 1.0 | Gradient |
| 3 | 2.67 | 25 | 0.2 | 100 | 1.0 | Isocratic |
| 4 | 3.08 | 45 | 0.2 | 100 | 1.2 | Isocratic |
| 5 | 3.83 | 30 | 0.2 | 40 | 1.0 | Isocratic |

*Loading Pump Buffer 10:90 Millipore Water:Methanol with 1 mM Ammonium Carbonate
Eluting Pump Buffer A Millipore Water
Eluting Pump Buffer B 10:90 Millipore Water:Methanol Mass Spectrometry: The flow of combined liquid solvents from the HTLC entered the turboionspray (ESI) interface of the MS/MS analyzer. The solvent/charged analyte mixture was first electrosprayed and converted to fine droplets after exiting the electrospray capillary. The residual solvent is removed from the charged analytes through a combination of heating and nitrogen gas flow to eventually yield gas phase analyte ions. The ions passed through the orifice of the instrument and entered the first quadrupole. Quadrupoles 1 and 3 (Q1 and Q3) were the mass filters, allowing selection of ions based on their mass to charge ratio (m/z). Quadrupole 2 (Q2) was the collision cell, where ions were fragmented.

The first quadrupole of the MS/MS (Q1) selected for molecules with the mass to charge ratio of thyroxine (775.5±1.0 m/z or mass units). Ions with these m/z passed to the collision chamber (Q2), while ions with any other m/z collided with the sides of the quadrupole and were fragmented. Ions entering Q2 collided with neutral gas molecules and fragmented. This process is called Collisionally Activated Dissociation (CAD). The CAD gas used in this example was nitrogen resulting in the generation of fragments (product). The fragment ions generated were passed into quadrupole 3 (Q3), where the two fragment ions of thyroxine to be measured (m/z 574.6+−.1.0 m/z & 126.8+−1.0 m/z or mass units) were selected for, while other ions were screened out. The selected fragment ions were measured by the detector. The same process was carried out for the internal standard, which was $^{13}C_6$-Thyroxine. Thus, the selected MS/MS transitions (nominal masses) measured were as follows: Thyroxine m/z 775 to 574 and 127, $^{13}C_6$-Thyroxine m/z 781 to 580 and 127.

Selected MS/MS parameters were as follows: Dwell time: 100 msec for each transition, Unit mass resolution in both resolving quadrupoles (Q1 and Q3) Curtain Gas: 20 CADgas: 6, Temp.: 450.degree. C. Gas1: 80, GS2: 40 CE: −80 for m/z 127 product ions, −45 for m/z 574 and 580 product ions. Electrospray voltage=−4500V.

As ions collide with the detector, they produce a pulse of electrons. The pulse was converted to a digital signal, which was counted to provide an ion count. The acquired data was relayed to the computer, which plotted counts of the ions collected vs. time.

Calculations

Calibration curves are constructed using the software system (Analyst) that controls the mass spectrometer. Calibration curves are generated by assigning the known concentrations to calibrators to generate a response ratio of analyte to internal standard versus concentration of analyte added [FIG. 20-26]. The concentrations of unknown samples are automatically calculated by comparing the response ratio of analyte to internal standard observed in measuring unknown samples to the calibration curve generated above.

Only results within the measurable range (2-100 pg/ml, 0.2-10 ng/dL) are valid.

Assay Performance Characteristics

A quantitative bioanalytical method for the determination of free thyroxine (FT4) in human serum using ED, LLE or sample dilution, and LC-MS/MS detection was developed and validated.

The assay was shown to be specific for the analysis of free thyroxine. Quantitative interference was not observed in the FT4 Dialysis Buffer. The matrix effect for free thyroxine and its internal standard was within acceptable limits for all post-dialysis sample types including pooled serum, plasma containing heparin and EDTA anticoagulants, hemolyzed and lipemic samples. Assay specificity was shown for $^{13}C_6$-Thyroxine internal standard.

The method was assayed and validated using four analytical batches. Replicates of spiked quality control (QC) samples at approximately 1.0, 1.5, 2.5 and 8.0 ng/dL were prepared in pooled serum to determine imprecision for free thyroxine. Replicates of calibrator samples at approximately 0.1, 0.2, 5.0 and 10.0 ng/dL were prepared in FT4 Dialysis Buffer to determine inaccuracy and imprecision for free thyroxine. The intra- and inter-assay inaccuracy (% bias) and imprecision (% CV) for the calibrators and QC (imprecision only) samples were ≦20% at the LLOQ and ≦15% at all other concentrations. The analytical range of the assay was validated between 0.2 ng/dL (LLOQ) and 10.0 ng/dL (ULOQ) for free thyroxine.

Spike and recovery experiments were performed using a post-dialysis serum pool and a FT4 Dialysis Buffer Calibrator containing low levels of thyroxine. The dialysate from the pool and the calibrator were spiked with pure thyroxine standard material. Mean recoveries of between 85% and 115% were observed for 1.0 ng/dL, 2.0 ng/dL and 8.0 ng/dL spikes respectively.

Hormone specificity interference less than the LLOQ response was observed during evaluation of free thyroxine for all analytes tested at relevant circulating levels.

Free thyroxine whole blood stability has been shown for up to 48 hours at room temperature. Free thyroxine calibrator stability has been shown for up to 16 hours at room temperature. Free thyroxine QC sample stability has been shown for up to 24 hours at room temperature. Free thyroxine calibrator and QC stability has been shown for up to 14 days when stored at −20° C. Free thyroxine calibrator and QC stability has been shown for up to three freeze/thaw cycles. Free thyroxine stock solution stability has been shown for up to 10 days frozen at −70° C. Free thyroxine working stock solution stability has been shown for up to 6 days when stored refrigerated at 4° C. $^{13}C_6$-Thyroxine internal standard solution stability has been shown for up to 7 days refrigerated at 4° C. Free thyroxine autosampler stability has been shown for 24 hours at 10° C.

Cross-validation of samples analyzed by Centaur (Free thyroxine) against ED-LLE followed by LC-MS/MS indicates acceptable bias. Comparison using scatter plots (FIG. 27) produces acceptable comparison for Centaur and ED-LLE followed by LC-MS/MS for Free thyroxine. Reference range transfer was successful for free thyroxine in adults and pre-pubertal children ages 2-8 years.

Standard curve fitting and reproducibility was evaluated using spiked standard samples at six concentrations. The standards were used to generate a weighted (1/x) linear regression calibration curve, which covered the range from 0.2 to 10.0 ng/dL for free thyroxine. Average inaccuracies and imprecision ≦20% at the LLOQ and ≦15% throughout the remainder of the range were observed. The correlation coefficients of the curves were greater than 0.98 (Tables 29-30).

Selectivity

Blank Matrix Interference.

Quadruplicate injections of FT4 Dialysis Buffer and 1:1 methanol:water were injected to determine the degree of blank matrix interference for thyroxine. For each assay, matrix analyte responses were less than the mean LLOQ responses.

Anticoagulant Effect on Measurement.

The effect of EDTA and heparin as anticoagulants was tested by drawing healthy volunteers using red top serum collection tubes and vacutainers containing sodium heparin and potassium EDTA anticoagulants. The results of the heparin and EDTA tubes were compared to the results from the serum collection tubes. It was found that variation of sample type and anticoagulant exhibited a bias <±15% for measurement of free thyroxine. Thus, plasma samples collected with heparin and EDTA are acceptable specimen types.

Anticoagulant Effect on Free Thyroxine Measurement

| Sample | Concentration (ng/dL) | | |
|---|---|---|---|
| | Serum | Heparin | EDTA |
| FT4 | 273.094* | 1.536 | 1.570 |
| | 1.746 | 1.754 | 1.669 |
| | 1.745 | 1.413 | 1.553 |
| | 1.651 | 1.521 | 1.527 |
| Mean | 1.714 | 1.556 | 1.580 |
| Mean Matrix Effect (%) | NA | −9.22 | −7.83 |
| n | 4 | 4 | 4 |

*Dialysis error, excluded from calculations;
NA = Not Applicable.

Effect of Lipemia and Hemolysis in the Matrix.

The effect of lipemia and hemolysis on the quantitative result was determined by spiking pooled patient serum with either a lipid solution or lysed red blood cells at a concentration of 5% by volume. The samples were run in quadruplicate and the results were compared to the results of the pool before contamination. A bias ≦±15% following addition of lipemic or hemolyzed material was observed for free thyroxine. Thus, lipemic and hemolyzed samples may be processed using this assay.

Effect of Lipemia and Hemolysis on Free Thyroxine Measurement

| Sample | Concentration (ng/dL) | | |
|---|---|---|---|
| | Serum | Lipemic | Hemolyzed |
| FT4 | 1.417 | 1.463 | 2.157* |
| | 1.403 | 1.385 | 1.684 |
| | 1.696 | 3.021* | 1.621 |
| | 1.285 | 1.547 | 1.602 |
| Mean | 1.450 | 1.465 | 1.636 |
| Mean Matrix Effect (%) | NA | 1.02 | 12.79 |
| n | 4 | 4 | 4 |

*= Data point outside 3SD from mean, excluded from calculations.
NA = Not Applicable.

Internal Standard Interference.

Internal standard ($^{13}C_6$-Thyroxine) working solution was spiked into FT4 Dialysis Buffer and tested in quadruplicate to evaluate the presence of unlabeled analyte. Internal standard ($^{13}C_6$-Thyroxine) interference response ≦LLOQ response was observed. Thus, $^{13}C_6$-Thyroxine interference was considered acceptable.

Matrix Effect.

Matrix effect was calculated at low, mid, and high level concentrations. Matrix effect for internal standard was measured at a single concentration. A minimum of 4 samples per QC level were analyzed for FT4 to determine matrix effect on quantitative result. Matrix effects were less than 15% for free thyroxine and $^{13}C_6$-Thyroxine Internal Standard when comparing water and dialysate from pooled samples.

Free Thyroxine Matrix Effect

| | Sample Matrix | | | | | |
|---|---|---|---|---|---|---|
| | Millipore Water | | | Post-Dialysis Pooled Serum | | |
| Post-Column Infusion Level | Analyte Peak Height (cps) | IS Peak Height (cps) | Ratio | Analyte Peak Height (cps) | IS Baseline Height (cps) | Ratio |
| Low Infusion | 24299.421 | 16100.000 | 1.509 | 26033.955 | 17600.000 | 1.479 |
| | 24027.876 | 15400.000 | 1.560 | 25844.532 | 16800.000 | 1.538 |
| | 25823.905 | 15900.000 | 1.624 | 25012.124 | 17100.000 | 1.463 |
| | 24917.386 | 15900.000 | 1.567 | 24618.647 | 15900.000 | 1.548 |
| MARR per Conc. | NA | NA | 1.565 | NA | NA | 1.507 |
| % Change | NA | NA | NA | NA | NA | −3.71 |
| Mid Infusion | 173144.290 | 24400.000 | 7.096 | 164420.482 | 21200.000 | 7.756 |
| | 181732.088 | 23100.000 | 7.867 | 164337.907 | 20800.000 | 7.901 |
| | 175921.645 | 23900.000 | 7.361 | 155907.875 | 20200.000 | 7.718 |
| | 178237.273 | 23400.000 | 7.617 | 156578.143 | 20000.000 | 7.829 |
| MARR per Conc. | NA | NA | 7.485 | NA | NA | 7.801 |
| % Change | NA | NA | NA | NA | NA | 4.22 |
| High Infusion | 303787.094 | 23000.000 | 13.208 | 264941.287 | 19500.000 | 13.587 |
| | 312136.060 | 21600.000 | 14.451 | 266588.958 | 19000.000 | 14.031 |
| | 329631.304 | 24400.000 | 13.509 | 272643.856 | 19100.000 | 14.275 |
| | 311677.872 | 22300.000 | 13.977 | 269085.967 | 19300.000 | 13.942 |
| MARR per Conc. | NA | NA | 13.786 | NA | NA | 13.959 |
| % Change | NA | NA | NA | NA | NA | 1.25 |

Matrix effect = [(Mean Analyte to Internal standard ratio in pooled serum)/Mean Analyte to Internal standard ratio in water)] − 1, expressed as a percentage Inaccuracy and Imprecision A. Intra-Assay and Inter-Assay Imprecision.

Intra-assay imprecision was calculated with replicate samples of spiked FT4 Buffer solutions (data from 4 runs) and replicate samples at different concentrations in post-dialysis pooled human serum (data from 4 runs). Inter-assay imprecision was calculated using data from each of the assay runs (n≧18). Free thyroxine exhibited intra and inter-assay imprecision ≦20% at the LLOQ, which was established to be 0.2 ng/dL, and ≦15% throughout the remainder of the linear range (0.2 to 10.0 ng/dL) in both post-dialysis pooled serum and FT4 Dialysis Buffer.

B. Intra-Assay and Inter-Assay Inaccuracy.

Intra-assay inaccuracy was calculated in 4 assay runs with replicates at 4 different concentrations in FT4 dialysis buffer spiked with known amounts of analyte. Inter-assay inaccuracy was calculated using data from each of 4 assay runs (n≧18). Free thyroxine exhibited intra and inter-assay inaccuracy ≦±20% at the LLOQ, which was established to be 0.2 ng/dL, and ≦±15% throughout the remainder of the linear range (0.2 to 10.0 ng/dL) in FT4 Dialysis Buffer.

A. Intra-Assay Precision

The intra-assay precision of the analytical method was calculated for four assays using patient pools (QC 1, QC 2, QC 3, and QC 4). The following tables show the data for these pools, as well as, the data from quality controls made from spiked FT4 Dialysis Buffer at four concentrations (0.1 ng/dL, 0.2 ng/dL, 5.0 ng/dL, and 10.0 ng/dL).

| Free Thyroxine Intra-assay Precision | | | | | | | | |
|---|---|---|---|---|---|---|---|---|
| Batch | Intra-day % CV | | | | | | | |
| Number | QC1 | QC2 | QC3 | QC4 | 0.1 | 0.2 | 5 | 10 |
| 1 | 9.61 | 4.75 | 3.89 | 3.79 | 153.4 | 4.98 | 6.20 | 5.53 |
| 2 | 12.16 | 9.55 | 5.53 | 4.41 | 39.65 | 5.12 | 5.24 | 2.19 |
| 3 | 4.96 | 2.31 | 5.44 | 6.42 | 22.20 | 4.37 | 4.05 | 5.47 |
| 4 | 3.92 | 3.51 | 4.29 | 5.89 | 117.7 | 2.48 | 0.53 | 3.90 |

B. Reproducibility

The inter-assay precision was calculated from the overall data from the precision assays for each of the QC samples. As shown in the table below, the method has acceptable inter-assay precision.

| Free Thyroxine Inter-Assay Precision | | | | | | | |
|---|---|---|---|---|---|---|---|
| | QC 1 | QC 2 | QC 3 | QC 4 | 0.1 | 0.2 | 5.0 | 10.0 |
| Average | 1.12 | 1.52 | 2.51 | 7.67 | 0.19 | 0.20 | 4.88 | 10.18 |
| % CV | 9.86 | 8.41 | 6.79 | 6.34 | 144.44 | 4.61 | 5.66 | 4.67 |
| N | 23 | 22 | 21 | 24 | 20 | 19 | 20 | 20 |

0.1 ng/dL standard failed inter-assay precision requirements, therefore 0.2 ng/dL standard determined to be the LLOQ.

Accuracy

The inter-assay accuracy was determined by calculating the percent bias for samples of known concentrations. FT4 Dialysis Buffer was spiked to 0.1 ng/dL, 0.2 ng/dL, 5.0 ng/dL, and 10.0 ng/dL and then assayed a total of at least 18 times in 4 different runs.

| Free Thyroxine Accuracy Data | | | | |
|---|---|---|---|---|
| | Concentration | | | |
| | 0.1 ng/dL | 0.2 ng/dL | 5.0 ng/dL | 10.0 ng/dL |
| Expected Result | 0.1 | 0.2 | 5.0 | 10.0 |
| Average Result | 0.102 | 0.198 | 4.884 | 10.184 |
| % Bias | 2.22 | −1.18 | −2.31 | 1.84 |

0.1 ng/dL standard failed Inter-Assay precision, therefore 0.2 ng/dL standard determined to be the LLOQ.

Spike and Recovery

Spike and Recovery Preparation

A post dialysis low level QC sample and a FT4 dialysis buffer calibrator were spiked with thyroxine. Recovery was performed by comparing the measured results of samples spiked with 1.0, 2.0, and 8.0 ng/dL of standard material against expected values. Samples were analyzed in quadruplicate. Free thyroxine assay exhibited recoveries >85% and <115%.

| Thyroxine Spike and Recovery | | | | |
|---|---|---|---|---|
| | Concentration Added (ng/dL) | | | |
| | 0.000 | 1.000 | 2.000 | 8.000 |
| | Concentration Measured (ng/dL) | | | |
| FT4 Calibrator | 0.949 | 1.885 | 2.760 | 8.691 |
| | 1.034 | 1.887 | 2.746 | 7.761 |
| | 0.972 | 1.873 | 2.900 | 8.867 |
| | 1.030 | 1.855 | 2.844 | 8.666 |
| Mean | 0.996 | 1.875 | 2.813 | 8.496 |
| Expected Conc. | NA | 1.996 | 2.996 | 8.996 |
| Recovery (%) | NA | 93.9 | 93.9 | 94.4 |
| n | 4 | 4 | 4 | 4 |
| Post-Dialysis Pooled Serum | 1.072 | 2.043 | 2.657 | 8.600 |
| | 1.084 | 1.963 | 2.905 | 8.285 |
| | 1.088 | 1.991 | 2.898 | 8.515 |
| | 1.097 | 1.992 | 2.761 | 8.124 |
| Mean | 1.085 | 1.997 | 2.805 | 8.381 |
| Expected Conc. | NA | 2.085 | 3.085 | 9.085 |
| Recovery (%) | NA | 95.8 | 90.9 | 92.2 |
| n | 4 | 4 | 4 | 4 |

NA = Not Applicable

Selectivity

Selectivity was tested by spiking 1 ng of the analytes listed below into 1 mL (equivalent to 100 ng/dL) of FT4 dialysis buffer before extraction and injection. Acceptability Criteria: Response less than the LLOQ at the appropriate retention time in excess of physiologically significant amounts of potential interfering substance.

The circulating concentrations of the cross reactants above are all at physiological concentrations less than 3 ng/dL. This concentration would give a response equal to 0.03 ng/dL of FT4 at most in the case of RT3. This is well below the level of detection for free thyroxine. Free thyroxine analysis is not affected by the presence of circulating hormones or drugs at physiological concentrations in the testing performed. Interfering substances are removed through sample purification, chromatography and selected reaction monitoring.

| Free Thyroxine Hormone Specificity | | | |
|---|---|---|---|
| Steroid | Amount added (ng/dL) | Measured Concentration (ng/dL) | Mean Relative Response (%) |
| Cross Reactant_T3 | 100 | 0.377 | 0.40 |
| Cross Reactant_T3 | 100 | 0.336 | |
| Cross Reactant_T3 | 100 | 0.519 | |
| Cross Reactant_T3 | 100 | 0.365 | |
| Cross Reactant_RT3 | 100 | 1.123 | 1.07 |
| Cross Reactant_RT3 | 100 | 1.032 | |
| Cross Reactant_RT3 | 100 | 1.082 | |
| Cross Reactant_RT3 | 100 | 1.025 | |
| Cross Reactant_3,5-DIT | 100 | 0.162 | 0.09 |
| Cross Reactant_3,5-DIT | 100 | 0.043 | |
| Cross Reactant_3,5-DIT | 100 | 0.062 | |
| Cross Reactant_3,5-DIT | 100 | 0.108 | |
| Cross Reactant_3-IT | 100 | 0.104 | 0.17 |
| Cross Reactant_3-IT | 100 | 0.183 | |
| Cross Reactant_3-IT | 100 | 0.176 | |
| Cross Reactant_3-IT | 100 | 0.208 | |

T3 = 3,5,3'-Triiodo-L-Thyronine;
RT3 = 3,3',5'-Triiodo-L-Thyronine;
3,5-DIT = 3,5-Diiodo-L-Thyronine;
3-IT = 3-Iodo-L-Thyronine.

Stability

Stability was demonstrated at the following conditions for the listed times.

| Storage Condition | Free thyroxine |
|---|---|
| Room Temperature | 1 day |
| Frozen (−20° C.) | 14 days |
| Freeze Thaw | 3 cycles |
| Whole Blood | 48 hours |
| Autosampler | 24 hours |
| Refrigerated (4° C.) | 7 days |

Inter-Assay Comparison
A. Bayer Centaur Immunoassay Compared to ED-LLE-LC-MS/MS.

A minimum of 25 routine samples representing the physiological range, were analyzed by ED-LLE-LC-MS/MS and Bayer Centaur for assay-to-assay comparison (see FIG. 27).

| Free Thyroxine Cross-Validation of Centaur to ED-LLE-LC-MS/MS | | | |
|---|---|---|---|
| | Concentration (ng/dL) | | |
| Sample # | Centaur | ED LC-MS/MS | Bias (%) |
| Sample 1 | 1.16 | 2.231 | 92.33 |
| Sample 2 | 1.29 | 1.781 | 38.06 |
| Sample 3 | 1.31 | 2.072 | 58.17 |
| Sample 4 | 0.99 | 1.265 | 27.78 |
| Sample 5 | 1.37 | 2.128 | 55.33 |
| Sample 6 | 1.58 | 2.274 | 43.92 |
| Sample 7 | 0.95 | 1.325 | 39.47 |
| Sample 8 | 1.12 | 1.272 | 13.57 |
| Sample 9 | 0.90 | 1.191 | 32.33 |
| Sample 10 | 1.03 | 1.305 | 26.70 |
| Sample 11 | 0.95 | 1.212 | 27.58 |
| Sample 12 | 1.63 | 2.399 | 47.18 |
| Sample 13 | 1.03 | 1.417 | 37.57 |
| Sample 14 | 1.11 | 1.545 | 39.19 |
| Sample 15 | 0.81 | 1.035 | 27.78 |
| Sample 16 | 1.15 | 1.647 | 43.22 |
| Sample 17 | 0.98 | 1.288 | 31.43 |
| Sample 18 | 1.36 | 2.145 | 57.72 |
| Sample 19 | 1.38 | 1.817 | 31.67 |
| Sample 20 | 1.43 | 2.591 | 81.19 |
| Sample 21 | 1.14 | 1.927 | 69.04 |
| Sample 22 | 1.00 | 1.159 | 15.90 |
| Sample 23 | 1.98 | 3.066 | 54.85 |
| Sample 24 | 0.38 | 0.297 | −21.84 |
| Sample 25 | 0.88 | 1.052 | 19.55 |
| Average bias (%) | | | 39.59 |

Bias (%) = (ED-LLE-LC-MS/MS result − Centaur result)/Centaur result, expressed as a percentage.

Inter-Assay Comparison of Centaur to LC-MS/MS:

Cross-validation of free thyroxine Centaur analysis to ED-LLE-LC-MS/MS yielded an average bias of 39.59% for samples within the analytical range. Comparison of data throughout the range generated a slope of 1.8145 with a correlation coefficient of 0.8923 (FIG. 27).

Reference Interval

A. Reference Range Sample Groups

Reference range transfer for free thyroxine was evaluated using NCCLS guidance (see references). Transfer of the reference range was established using the samples listed below.

| Normal Patient Serum Reference Sample Groups | | | |
|---|---|---|---|
| | Children[1] | Adult Males | Adult Females |
| Sample Number | 50 | 25 | 25 |

[1]Children samples will include 25 boys <10 years old and 25 girls <9 years old.

B. Reference Interval of Patient Test Results

| Reference Intervals Range (ng/dL) | |
|---|---|
| Premature Infants: | |
| 26-30 Weeks, 3-4 Days | 0.4-2.8 |
| Full-Term Infants: | |
| 3 Days: | 2.0-4.9 |
| 1-11 Months | 0.9-2.6 |
| Prepubertal Children: | 0.8-2.2 |
| Pubertal Children and Adults: | 0.8-2.3 |

C. Reference Range Transfer

Guidance provided by NCCLS allows reference range transfer where 2 out of 20 (10%) of samples fall outside the original reference range.

It was found that all normal adult female samples were within range for reference range transfer of FT4. Adult female reference ranges are transferable. All normal adult male samples were within range for reference range transfer of FT4. Adult male reference ranges are transferable. There was one pre-pubertal reference sample that was outside the normal reference range, and another sample that was potentially out of range. Both samples initially produced high results and upon repeat one sample was still high outside of normal range, while the other was within normal range. The reference sample that repeated within range was not run a third time, which would be in accordance with sample repeat requirements, due to the fact that the pre-pubertal reference range passes with or without this sample being in the normal reference range. A total of 48 out of 50 pre-pubertal reference samples were within range for reference range transfer of FT4. Pre-pubertal reference ranges are transferable. Thus, the free thyroxine reference range transfer acceptance criteria were met.

Free Thyroxine Adult Reference Range Verification

| Adults | Concentration (ng/dL) FT4 Result | Adults | Concentration (ng/dL) FT4 Result |
|---|---|---|---|
| Female 1 | 1.039 | Male 1 | 1.474 |
| Female 2 | 1.074 | Male 2 | 1.566 |
| Female 3 | 1.311 | Male 3 | 1.631 |
| Female 4 | 1.383 | Male 4 | 1.210 |
| Female 5 | 0.977 | Male 5 | 1.520 |
| Female 6 | 1.120 | Male 6 | 1.226 |
| Female 7 | 1.501 | Male 7 | 1.417 |
| Female 8 | 1.010 | Male 8 | 1.432 |
| Female 9 | 1.236 | Male 9 | 1.538 |
| Female 10 | 1.277 | Male 10 | 1.430 |
| Female 11 | 1.263 | Male 11 | 1.292 |
| Female 12 | 1.317 | Male 12 | 1.153 |
| Female 13 | 1.452 | Male 13 | 1.268 |
| Female 14 | 0.983 | Male 14 | 1.107 |
| Female 15 | 1.432 | Male 15 | 1.528 |
| Female 16 | 1.270 | Male 16 | 1.479 |
| Female 17 | 1.005 | Male 17 | 1.338 |
| Female 18 | 1.071 | Male 18 | 1.411 |
| Female 19 | 1.132 | Male 19 | 1.470 |
| Female 20 | 1.414 | Male 20 | 1.597 |
| Female 21 | 1.405 | Male 21 | 1.660 |
| Female 22 | 1.355 | Male 22 | 1.312 |
| Female 23 | 1.767 | Male 23 | 1.150 |
| Female 24 | 1.086 | Male 24 | 1.188 |
| Female 25 | 1.566 | Male 25 | 1.780 |

Male and Female samples are from an in house draw and are considered to be a healthy reference population.
Free thyroxine adult reference range is 0.8 to 2.3 ng/dL.

Free Thyroxine Pre-pubertal Reference Range Verification

| Children | Concentration (ng/dL) FT4 Result | Children | Concentration (ng/dL) FT4 Result |
|---|---|---|---|
| Female 1 | 1.848 | Male 1 | 1.845 |
| Female 2 | 1.543 | Male 2 | 1.740 |
| Female 3 | 1.561 | Male 3 | 1.569 |
| Female 4 | 1.604 | Male 4 | 1.753 |
| Female 5 | 1.974 | Male 5 | 1.849 |
| Female 6 | 1.826 | Male 6 | 2.090 |
| Female 7 | 1.485 | Male 7 | 1.624 |
| Female 8 | 1.846 | Male 8 | 1.704 |
| Female 9 | 1.528 | Male 9 | 2.047 |
| Female 10 | 1.612 | Male 10 | 2.754 RPT = 2.474 |
| Female 11 | 1.800 | Male 11 | 1.765 |
| Female 12 | 1.585 | Male 12 | 2.54 RPT = 1.799 |
| Female 13 | 1.812 | Male 13 | 2.167 |
| Female 14 | 1.801 | Male 14 | 1.304 |
| Female 15 | 1.471 | Male 15 | 1.656 |
| Female 16 | 1.853 | Male 16 | 1.860 |
| Female 17 | 1.617 | Male 17 | 1.063 |
| Female 18 | 1.443 | Male 18 | 1.536 |
| Female 19 | 1.619 | Male 19 | 1.494 |
| Female 20 | 1.553 | Male 20 | 1.875 |
| Female 21 | 1.827 | Male 21 | 1.629 |
| Female 22 | 1.956 | Male 22 | 1.966 |
| Female 23 | 1.549 | Male 23 | 1.583 |
| Female 24 | 1.820 | Male 24 | 1.508 |
| Female 25 | 1.886 | Male 25 | 1.902 |

Pre-pubertal children samples were previously tested in Allergy screens and assumed as normal. Children ranging from ages 2-8 years for both males and females were selected. Free thyroxine pre-pubertal reference range is 0.8 to 2.2 ng/dL RPT is the repeat value for the sample after being run a second time for verification of initial high result.

Standard Curve Fitting and Reproducibility

The reproducibility of the standard curve was evaluated by comparing the back-calculated concentrations to the theoretical concentration of the standard in 5 analytical runs. The calibrator concentrations for free thyroxine (ng/dL) were as follows: 0.1, 0.2, 0.5, 1.0, 2.5, 5.0, and 10.0.

The reproducibility of the standard curve was evaluated, using standards 2-7, by comparing the back-calculated concentrations to the actual concentration of the standard in five analytical runs. The curve was fit with a straight line with weighted 1/x fit, as established during method development. Free thyroxine calibration curves exhibited mean imprecision <15% for all concentrations between 0.2 ng/dL and 10.0 ng/dL. Correlation coefficients were greater than 0.98.

Analytical Reportable Range

A. LLOQ (Lower Limit of Quantification)

The lower limit of quantification for free thyroxine using this assay was 0.2 ng/dL as determined during evaluation of inaccuracy, imprecision and calibration curve reproducibility.

B. ULOQ (Upper Limit of Quantification) The upper limit of quantification using this assay was 10.0 ng/dL for free thyroxine, as determined during evaluation of inaccuracy, imprecision and calibration curve reproducibility.

Dye Marker Analysis

A. Dye Marker Correlation

Blue dextran was used as a visual dye marker to indicate membrane leakage during dialysis. Various concentrations of blue dextran (18 mg/mL, 9 mg/mL, and 4.5 mg/mL in water) were added to the sample side of the dialysis plate, and the results were compared to the same samples that were run with no dye added to see if the dye had any effect on dialysis of FT4 All concentrations of blue dextran tested correlated to the results obtained when no dye was used. The highest concentration of blue dextran tested, 18.0 mg/mL, will be used as an indicator of membrane leakage during the dialysis step. This concentration of blue dextran was easily noted when membrane leakage occurred.

Free Thyroxine Standard Curve Fitting and Reproducibility

| | Std 2 | Std 3 | Std 4 | Std 5 | Std 6 | Std 7 |
|---|---|---|---|---|---|---|
| | \multicolumn{6}{c}{Actual Concentration (ng/dL)} | | | | | |
| Batch | 0.200 | 0.500 | 1.000 | 2.500 | 5.000 | 10.000 |
| 1 | 0.231 | 0.489 | 0.960 | 2.511 | 4.824 | 10.642 |
|   | 0.190 | 0.480 | 0.989 | 2.536 | 5.023 | 9.524 |
| 2 | 0.181 | 0.518 | 0.976 | 2.501 | 4.728 | 10.478 |
|   | 0.190 | 0.516 | 1.106 | 2.623 | 4.881 | 9.701 |
| 3 | 0.484* | 0.525 | 0.999 | 2.451 | 4.556 | 10.816 |
|   | 0.227 | 0.473 | 0.938 | 2.432 | 5.070 | 9.713 |
| 4 | 0.188 | 0.509 | 1.030 | 2.565 | 4.936 | 10.796 |
|   | 2.113* | 0.498 | 0.980 | 2.580 | 5.007 | 9.111 |
| 5 | 0.207 | 0.508 | 0.992 | 2.531 | 5.061 | 9.878 |
|   | 0.184 | 0.549 | 0.923 | 2.412 | 5.228 | 9.927 |

-continued

Free Thyroxine Standard Curve Fitting and Reproducibility

| Batch | Std 2 | Std 3 | Std 4 | Std 5 | Std 6 | Std 7 |
|---|---|---|---|---|---|---|
| | | | Actual Concentration (ng/dL) | | | |
| | 0.200 | 0.500 | 1.000 | 2.500 | 5.000 | 10.000 |
| Mean | 0.200 | 0.507 | 0.989 | 2.514 | 4.931 | 10.059 |
| Accuracy (% RE) | −0.12 | 1.30 | −1.07 | 0.57 | −1.37 | 0.59 |
| Precision (% RSD) | 9.83 | 4.46 | 5.17 | 2.68 | 3.91 | 5.85 |
| n | 8 | 10 | 10 | 10 | 10 | 10 |

*Outliers excluded due to preparative error

Free Thyroxine Standard Curve Fitting and Reproducibility Continued

| Batch | $K_0$ (Y-intercept) | $K_1$ (slope) | Correlation Coefficient |
|---|---|---|---|
| 1 | 0.0489 | 0.2840 | 0.9987 |
| 2 | 0.0457 | 0.2980 | 0.9988 |
| 3 | 0.0344 | 0.3070 | 0.9978 |
| 4 | 0.0268 | 0.3110 | 0.9974 |
| 5 | 0.0408 | 0.2880 | 0.9995 |
| Mean | 0.0393 | 0.2976 | 0.9984 |
| Precision (% RSD) | NA | 3.92 | 0.08 |
| n | 5 | 5 | 5 |

NA = Not Applicable.
Data calculated using Standards 2-7.

Free Thyroxine Dye Marker Correlation

| Blue Dextran Concentration | Concentration (ng/dL) | | | | | |
|---|---|---|---|---|---|---|
| | QC1 | QC2 | QC3 | QC4 | Patient 3 | |
| 0 mg/mL Dye | 1.23 | 1.90 | 2.49 | 7.00 | 0.93 | |
| 0 mg/mL Dye | 1.09 | 1.75 | 2.71 | 7.06 | N/A | |
| Average Concentration | 1.16 | 1.83 | 2.60 | 7.03 | 0.93 | |
| 4.5 mg/mL Dye | 1.11 | 1.87 | 2.53 | 7.71 | 0.94 | Average |
| 4.5 mg/mL Dye | 1.14 | 1.59 | 2.69 | 7.53 | 0.88 | Bias (%) |
| Average Concentration | 1.13 | 1.73 | 2.61 | 7.62 | 0.91 | −0.20 |
| Bias (%) | −3.02 | −5.23 | 0.33 | 8.45 | −1.51 | |
| 9.0 mg/mL Dye | 1.14 | 1.70 | 2.69 | 7.09 | 0.94 | Average |
| 9.0 mg/mL Dye | 1.06 | 1.70 | 2.74 | 6.55 | 0.99 | Bias (%) |
| Average Concentration | 1.10 | 1.70 | 2.72 | 6.82 | 0.97 | −1.28 |
| Bias (%) | −5.39 | −6.90 | 4.48 | −2.96 | 4.37 | |
| 18.0 mg/mL Dye | 1.14 | 1.90 | 2.79 | 6.95 | 0.99 | Average |
| 18.0 mg/mL Dye | 1.16 | 1.58 | 2.85 | 7.45 | 1.02 | Bias (%) |
| Average Concentration | 1.15 | 1.74 | 2.82 | 7.20 | 1.00 | 2.79 |
| Bias (%) | −0.95 | −4.52 | 8.42 | 2.50 | 8.48 | |

N/A = Not Applicable; only 1 duplicate run.
Bias (%) = (Average concentration dye added − Average concentration no dye added)/Average concentration no dye added, expressed as a percentage.

Example 3

For dialysis of samples to remove free thyroxine or other free hormones from hormones that are bound to proteins in the sample, a 200 microliter (μL) sample and 10 μL of an 18 mg/mL dextran blue are added to one side of a 5 or 10 kilodalton molecular weight cut-off cellulose dialysis membrane in a 96-well equilibrium dialysis plate and capped. Then, 300 microliters of a dialyzing buffer (described in Example 2) is added to the other side of the plate and the wells are capped. The plate is placed vertically within a temperature controlled (37° C.) rotating oven and rotated at 15 cycles per minute for 16 hours. The 96-well plate may then be removed from the rotating oven and the dialysate buffer side is uncapped. A sample of 200 μL may be removed for processing by either liquid extraction using the isotope dilution LC-MS/MS method.

In some cases, a liquid extraction step is performed after the dialysis to remove residual salts and/or other additives which are used in the dialysis solution and/or remain from the sample, but that may interfere with the MS/MS analysis. The dialysate is extracted with 71.25:23.75:5 ethyl acetate:hexane:methanol. Alternatively, the dialysate is diluted with a solution of 1:1 methanol:water containing stable labeled internal standard and directly injected onto the LC-MS/MS system for analysis.

Example 4

2D-LC-MS/MS Analysis for 25-Hydroxyvitamin D2 and 25-Hydroxyvitamin D3

25-Hydroxyvitamin D3 (Native) and 25-Hydroxyvitamin D2 (Supplemented) analysis was validated to 1 ng/mL using 200-μL of sample. Optimum analytical specificity and sensitivity was generated using 2D LC using gradient separations in both LC dimensions, heart-cutting and chromato-focusing prior to MS/MS detection.

Abbreviations for Examples

ALQ: Above limit of quantification; BLQ: Below limit of quantification; CAP: College of American Pathologists; CLIA: Clinical Laboratory Improvement Act; CPS: Counts per scan; CV: Coefficient of variance; ED: Equilibrium Dialysis; EDTA: Ethylenediamminotetraacetic acid; FT4: Free Thyroxine; IE: Injection Error; IS: Internal Standard; LC: Liquid Chromatography; LLE: Liquid-Liquid Extraction; LLOQ: Lower Limit of Quantitation; MARR: Mean average response ratio; MS/MS: Tandem MS/MS detection; N: Number of replicates; NA: Not Applicable; QC: Quality Control; R: Correlation Coefficient; RIA: Radioimmunoassay; SD: Standard Deviation; ULOQ: Upper Limit of Quantitation All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

That which is claimed:

1. A method for determining the presence or amount of estradiol in a biological sample from a patient comprising:
   (a) providing a biological sample to be assayed comprising a range of about 1.0 pg to 500 pg estradiol;
   (b) extracting the estradiol from the biological sample by liquid-liquid extraction;
   (c) purifying the extracted estradiol using two-dimensional HPLC;
   (d) heating the sample under conditions such that dehydration of estradiol in the sample occurs;

(e) generating one or more fragment ions of the precursor ion; and (f) detecting the presence of estradiol precursor and/or product ions by tandem mass spectrometry and relating the detected ions to the presence or amount of the estradiol in the sample to render a clinical diagnosis.

2. The method of claim 1, wherein the estradiol precursor ion has a mass/charge ratio (m/z) of about 255.2 and the fragment ions comprise ions having a mass/charge ratio (m/z) of about 159.0 and 133.0.

3. The method of claim 1, wherein the sample further comprises estrone.

4. The method of claim 3, wherein the range of estrone detected is from about 2.5 pg/mL to about 500 pg/mL.

5. The method of claim 3, wherein the estrone precursor ion has a mass/charge ratio (m/z) of about 273 and the fragment ions comprise ions having a mass/charge ratio (m/z) of about 159.0 and 133.0.

6. The method of claim 1, wherein the sample is heated in the MS/MS interface.

7. The method of claim 1, wherein the quantitation is such that the matrix effects from other components in the biological sample are less than 15%.

8. The method of claim 1, wherein the method distinguishes one of the following components of the biological sample comprises at least one of dihydrotestosterone, androstenediol, 5-androsten-3, 11,17-trione, androstenedione, 17a-methyltestosterone, cortisone, epitestosterone, dehydroepiandrosternedione, dexamethasone, 5a-androstan-3b, 17b-diol, 5b-androstan-3a, 17b-diol, epiandrosterone, 17a-hydroxyprogesterone, 11-desoxycortisol, prednisone, estriol, corticosterone, androsterone, prednisolone, 17-hydroxypergnenolone, progesterone, 20a-hydroxy-progesterone, 20b-hydroxy-progesterone, beclomethasone, triamcinolone acetonide, fluticasone propionate, pregnanetriol, tetrahydrocortisol, tetrahydrocortisone, pregnenolone sulphate, ethinyl estradiol, budesonide, pregnanediol, desoxycorticosterone, cortisol, 21-desoxycortisol, pregnenolone, andrenosterone, aldosterone, dihydroandrosterone, 11a-hydroxy-progesterone, testosterone and estrone-3-sulfate.

* * * * *